US012291740B2

(12) United States Patent
Chun et al.

(10) Patent No.: US 12,291,740 B2
(45) Date of Patent: *May 6, 2025

(54) DETECTION OF TARGET NUCLEIC ACID SEQUENCES USING DIFFERENT DETECTION TEMPERATURES

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/124,977

(22) PCT Filed: Dec. 9, 2014

(86) PCT No.: PCT/KR2014/012074
§ 371 (c)(1),
(2) Date: Sep. 9, 2016

(87) PCT Pub. No.: WO2015/147412
PCT Pub. Date: Oct. 1, 2015

(65) Prior Publication Data
US 2017/0247750 A1 Aug. 31, 2017

Related U.S. Application Data

(60) Provisional application No. 61/979,545, filed on Apr. 15, 2014.

(30) Foreign Application Priority Data

Mar. 28, 2014 (KR) .................. 10-2014-0037310
May 9, 2014 (WO) ................. PCT/KR2014/004173
Jul. 23, 2014 (WO) ................. PCT/KR2014/006714

(51) Int. Cl.
| C12Q 1/686 | (2018.01) |
| C12Q 1/6816 | (2018.01) |
| C12Q 1/6827 | (2018.01) |
| C12Q 1/6858 | (2018.01) |
| G01N 25/04 | (2006.01) |
| C07H 21/00 | (2006.01) |

(52) U.S. Cl.
CPC ......... *C12Q 1/6816* (2013.01); *C12Q 1/6827* (2013.01); *C12Q 1/6858* (2013.01); *G01N 25/04* (2013.01)

(58) Field of Classification Search
None
See application file for complete search history.

(56) References Cited

U.S. PATENT DOCUMENTS

| 5,538,848 | A | 7/1996 | Livak et al. | |
| 6,444,661 | B1* | 9/2002 | Barton ............... | C07F 15/008 514/185 |
| 9,284,607 | B2 | 3/2016 | Fu | |
| 9,540,681 | B2 | 1/2017 | Chun et al. | |
| 10,752,938 | B2* | 8/2020 | Chun ................... | C12Q 1/6858 |
| 11,859,243 | B2* | 1/2024 | Chun ................... | G16B 40/10 |
| 2002/0065609 | A1* | 5/2002 | Ashby ................. | C12Q 1/6809 702/20 |
| 2005/0053950 | A1 | 3/2005 | Ubani et al. | |
| 2007/0031829 | A1* | 2/2007 | Yasuno ............... | C12Q 1/6886 435/6.12 |
| 2007/0042400 | A1* | 2/2007 | Choi .................... | C12N 15/10 435/6.12 |
| 2007/0042419 | A1* | 2/2007 | Barany ............... | C12Q 1/6813 435/6.12 |
| 2011/0244460 | A1* | 10/2011 | Hirai et al. ......... | C12Q 1/6848 435/6.11 |
| 2012/0014977 | A1* | 1/2012 | Furihata ............. | C07K 14/4748 424/185.1 |
| 2012/0116686 | A1 | 5/2012 | Palais | |
| 2012/0253689 | A1* | 10/2012 | Rogan ................. | G16B 30/00 702/20 |
| 2014/0057263 | A1* | 2/2014 | Engel ................... | C12Q 1/6876 536/24.3 |
| 2014/0057264 | A1* | 2/2014 | Chun ................... | C12Q 1/6853 435/6.11 |

(Continued)

FOREIGN PATENT DOCUMENTS

| JP | 2004533801 A | 11/2004 |
| JP | 2012513215 A | 6/2012 |

(Continued)

OTHER PUBLICATIONS

"Oligonucleotide definition," Merriam-Webster.com; accessed Aug. 23, 2017. (Year: 2017).*
Forster et al., "A human gut bacterial genome and culture collection for improved metagenomic analyses", Nature Biotechnology, vol. 37, Feb. 2019, pp. 186-192. (Year: 2019).*
Teixeira and Cooper, "Using hominin introgression to trace modern human dispersals", PNAS, Jul. 30, 2019, vol. 116, No. 31, 15327-15332. (Year: 2019).*
Forster et al., "A human gut bacterial genome and culture collection for improved metagenomic analyses", Nature Biotechnology, vol. 37, Feb. 2019, 186-192. (Year: 2019).*
Zhu et al., "A Novel Coronavirus from Patients with Pneumonia in China, 2019", The New England Journal of Medicine, vol. 382, Jan. 2020, pp. 727-733. (Year: 2020).*
Kim et al., "The Architecture of SARS-CoV-2 Transcriptome", Cell, vol. 181, May 14, 2020, pp. 914-921. (Year: 2020).*
"List of sequenced bacterial genomes", Wikipedia.com; accessed Jan. 24, 2014. (Year: 2014).*

(Continued)

*Primary Examiner* — Bradley L. Sisson
(74) *Attorney, Agent, or Firm* — Sughrue Mion, PLLC

(57) ABSTRACT

The present invention relates to detection of target nucleic acid sequences using different detection temperatures. The present invention employing different detection temperatures enables to detect a plurality of target nucleic acid sequences in conventional real-time manners even with a single type of label in a single reaction vessel. The conventional technologies detect a plurality of target nucleic acid sequences by a melting analysis after target amplification. Unlikely, the present invention does not require a melting analysis after target amplification, such that the time for analysis is greatly reduced.

10 Claims, 18 Drawing Sheets
Specification includes a Sequence Listing.

(56) References Cited

U.S. PATENT DOCUMENTS

| | | | |
|---|---|---|---|
| 2017/0027750 A1 | 2/2017 | Wiley | |
| 2017/0362646 A1 | 12/2017 | Chun et al. | |
| 2018/0057868 A1* | 3/2018 | Walder | C12Q 1/6869 |

FOREIGN PATENT DOCUMENTS

| | | | |
|---|---|---|---|
| JP | 2013540449 A | 7/2013 |
| JP | 2013538041 A | 10/2013 |
| WO | 2006044994 A2 | 4/2006 |
| WO | 2010013017 A1 | 2/2010 |
| WO | 2010017543 A1 | 2/2010 |
| WO | 2010068576 A1 | 6/2010 |
| WO | 2010104768 A1 | 9/2010 |
| WO | 2011019837 A1 | 2/2011 |
| WO | 2012048207 A2 | 4/2012 |
| WO | 2012096523 A2 | 7/2012 |
| WO | 2013115442 A1 | 8/2013 |
| WO | 2013133561 A1 | 9/2013 |
| WO | 2014022827 A1 | 2/2014 |
| WO | 2015147370 A1 | 10/2015 |

OTHER PUBLICATIONS

"Fungi," Wikipedia.com; accessed Jun. 3, 2013. (Year: 2013).*
"How many species of bacteria are there", wisegeek.com; accessed Jan. 21, 2014. (Year: 2014).*
"Viruses", Wikipedia.com, accessed Nov. 24, 2012. (Year: 2012).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
"A Timeline of COVID-19 Variants", Team Verywell Health, Dec. 19, 2023, pp. 1-12. (Year: 2023).*
"The complete sequence of a human Y chromosome", Rhe et al., Nature, vol. 621, Sep. 14, 2023, p. 3444. (Year: 2023).*
Sanchez, J. Aquiles, et al., Two-temperature LATE-PCR endpoint genotyping, BMC Biotechnology 2006, vol. 6, No. 44, pp. 1-14.
Gundry, Cameron N., et al., Amplicon Melting Analysis with Labeled Primers; A Closed-Tube Method for differentiating Homozygotes and Heterozygotes, Clinical Chemistry, 2003, vol. 49, No. 3, pp. 396-406.
Huang, Qiuying, et al., Multiplex Fluorescence Melting Curve Analysis for Mutation Detection with Dual-Labeled, Self-Quenched Probes, PLos ONE, Apr. 2001, vol. 6, Issue 4, pp. 1-9.
Chakravorty, S., et al.; Rapid Detection of Fluoroquinolone-Resistant and Heteroresistant Mycobacterium tuberculosis by Use of Sloppy Molecular Beacons and Dual Melting-Temperature Codes in a Real-Time PCR Assay; Journal of Clinical Microbiology, Mar. 2011, vol. 49, No. 3, pp. 932-940.
Liu, Q., et al.; Triplex real-time PCR melting curve analysis for detecting Mycobacterium tuberculosis mutations associated with resistance to second-line drugs in a single reaction; Journal of Antimicrobial Chemotherapy, 2013, vol. 68, pp. 1097-1103.
Pierce, K., et al.; Rapid detection and identification of hepatitis C virus (HCV) sequences using mismatch-tolerant hyridization probes: A general method for analysis of sequence variation; Reports, 2013, vol. 55, No. 3, pp. 125-132.
Alvandi, E., et al.; Zip nucleic acid: a new reliable method to increase the melting temperature of real-time PCR probes; Journal of Diabetes & Metabolic Disorders, 2014, vol. 13, pp. 1-4.

* cited by examiner

Target is genomic DNA of *Chlamydia trachomatis* (CT) and *Neisseria gonorrhoeae* (NG). NTC represents No Target Control.

FIG. 1B

| Tube | Target[1] | End-RFU[2] | | End-Ratio[3] | Threshold[4] | Result for NG |
|---|---|---|---|---|---|---|
| | | 72°C | 60°C | | | |
| 1 | CT | 1595 | 1839 | 1.2 | | - |
| 2 | NG | 48.7 | 1787 | 36.7 | 1.5 | + |
| 3 | CT + NG | 1454 | 3062 | 2.1 | | + |
| 4 | NTC | 3.41 | 2.33 | 0.7 | | - |

[1] Target is genomic DNA of *Chlamydia trachomatis* (CT) and *Neisseria gonorrhoeae* (NG). NTC represents No Target Control.
[2] End-RFU represents relative fluorescence units at 50th cycle.
[3] End-Ratio represents the ratio of End-RFU at 60°C to End-RFU at 72°C.
[4] Threshold is a threshold value for distinguishing the presence or absence of NG.

| Tube | Target[2] | Threshold[3] | $C_t$ value for NG |
|---|---|---|---|
| 1 | CT | | - |
| 2 | NG | 0.10 | 32.90 |
| 3 | CT + NG | | 33.18 |
| 4 | NTC | | - |

[1] Ratio represents the ratio of RFU at 60°C to RFU at 72°C at each cycle.
[2] Target is genomic DNA of *Chlamydia trachomatis* (CT) and *Neisseria gonorrhoeae* (NG). NTC represents No Target Control.
[3] Threshold is a threshold value for distinguishing the presence or absence of NG.

Target is genomic DNA of *Chlamydia trachomatis* (CT) and *Neisseria gonorrhoeae* (NG). NTC represents No Target Control.

FIG. 1E

| Tube | Target[1] | NG (60°C) | |
|---|---|---|---|
| | | Individual Threshold[2] | $C_t$ value |
| 1 | CT | 2393 | - |
| 2 | NG | 200 | 31.32 |
| 3 | CT + NG | 2181 | 35.83 |
| 4 | NTC | 200 | - |

[1] Target is genomic DNA of *Chlamydia trachomatis* (CT) and *Neisseria gonorrhoeae* (NG). NTC represents No Target Control.

[2] Individual threshold for the signal at 60°C is a threshold value for distinguishing the presence or absence of NG in each tube.

Target is genomic DNA of *Chlamydia trachomatis* (CT) and *Neisseria gonorrhoeae* (NG). NTC represents No Target Control.

FIG. 2B

| Tube | Target[1] | End-RFU[2] | | End-Ratio[3] | Threshold[4] | Result for NG |
|------|-----------|------|------|----------|-----------|--------|
| | | 72°C | 60°C | | | |
| 1 | CT | 2172 | 2413 | 1.1 | 1.2 | - |
| 2 | NG | 1.18 | 1508 | 1278.0 | | + |
| 3 | CT + NG | 2030 | 3572 | 1.8 | | + |
| 4 | NTC | 1.36 | 1.35 | 1.0 | | - |

[1] Target is genomic DNA of *Chlamydia trachomatis* (CT) and *Neisseria gonorrhoeae* (NG). NTC represents No Target Control.
[2] End-RFU represents relative fluorescence units at 50th cycle.
[3] End-Ratio represents the ratio of End-RFU at 60°C to End-RFU at 72°C.
[4] Threshold is a threshold value for distinguishing the presence or absence of NG.

| Tube | Target[2] | Threshold[3] | $C_t$ value for NG |
|---|---|---|---|
| 1 | CT | | - |
| 2 | NG | 0.10 | 37.88 |
| 3 | CT + NG | | 37.20 |
| 4 | NTC | | - |

[1] Ratio represents the ratio of RFU at 60°C to RFU at 72°C at each cycle.
[2] Target is genomic DNA of *Chlamydia trachomatis* (CT) and *Neisseria gonorrhoeae* (NG). NTC represents No Target Control.
[3] Threshold is a threshold value for distinguishing the presence or absence of NG.

Target is genomic DNA of *Chlamydia trachomatis* (CT) and *Neisseria gonorrhoeae* (NG). NTC represents No Target Control.

FIG. 2E

| Tube | Target[1] | NG (60°C) | |
| --- | --- | --- | --- |
| | | Individual Threshold[2] | $C_t$ value |
| 1 | CT | 2606 | - |
| 2 | NG | 200 | 36.21 |
| 3 | CT + NG | 2436 | 37.07 |
| 4 | NTC | 200 | - |

[1] Target is genomic DNA of *Chlamydia trachomatis* (CT) and *Neisseria gonorrhoeae* (NG). NTC represents No Target Control.

[2] Individual threshold for the signal at 60°C is a threshold value for distinguishing the presence or absence of NG in each tube.

Target is genomic DNA of *Chlamydia trachomatis* (CT) and *Neisseria gonorrhoeae* (NG). NTC represents No Target Control.

Target is human genomic DNA of wild, mutant, and hetero-type MTHFR (C677T). NTC represents No Target Control.

FIG. 4B

| Tube | Target[1] | End-RFU[2] | | End-Ratio[3] |
|---|---|---|---|---|
| | | 55°C | 72°C | |
| 1 | Wild-type | 1164 | 1001 | 1.2 |
| 2 | Mutant-type | 953 | 117 | 8.1 |
| 3 | Hetero-type | 1172 | 621 | 1.9 |
| 4 | NTC | 1.56 | 1.58 | 1.0 |

[1] Target is human genomic DNA of wild, mutant, and hetero-type MTHFR (C677T). NTC represents No Target Control.
[2] End-RFU represents relative fluorescence units at 50th cycle.
[3] End-Ratio represents the ratio of End-RFU at 55°C to End-RFU at 72°C.

Target is genomic DNA of *Mycoplasma genitalium* (MG), *Chlamydia trachomatis* (CT), and *Neisseria gonorrhoeae* (NG). NTC represents No Target Control.

Target is genomic DNA of *Mycoplasma genitalium* (MG), *Chlamydia trachomatis* (CT), and *Neisseria gonorrhoeae* (NG). NTC represents No Target Control.

Target is genomic DNA of *Mycoplasma genitalium* (MG), *Chlamydia trachomatis* (CT), and *Neisseria gonorrhoeae* (NG). NTC represents No Target Control.

FIG. 5D

| Tube | Target[1] | End-RFU[2] 95°C | End-RFU[2] 72°C | End-△RFU[3] | Threshold[4] | Result for CT |
|---|---|---|---|---|---|---|
| 1 | NG | 39 | 283 | 244 | | - |
| 2 | CT | 23 | 1687 | 1664 | | + |
| 3 | MG | 1843 | 2083 | 240 | | - |
| 4 | NG+CT | 56 | 1457 | 1401 | 300 | + |
| 5 | NG+MG | 1721 | 1918 | 197 | | - |
| 6 | CT+MG | 1714 | 3457 | 1743 | | + |
| 7 | NG+CT+MG | 1792 | 3535 | 1743 | | + |
| 8 | NTC | 26 | 125 | 99 | | - |

[1] Target is genomic DNA of *Mycoplasma genitalium* (MG), *Chlamydia trachomatis* (CT), and *Neisseria gonorrhoeae* (NG). NTC represents No Target Control.
[2] End-RFU represents relative fluorescence units at 50th cycle.
[3] End-△RFU represents the value obtained by subtracting the RFU at 95°C from that at 72°C
[4] Threshold is a threshold value for distinguishing the presence or absence of CT.

FIG. 5E

| Tube | Target[1] | End-RFU[2] | | End-△RFU[3] | Threshold[4] | Result For NG |
|---|---|---|---|---|---|---|
| | | 72°C | 60°C | | | |
| 1 | NG | 283 | 1711 | 1428 | | + |
| 2 | CT | 1687 | 1937 | 250 | | - |
| 3 | MG | 2083 | 2594 | 511 | | - |
| 4 | NG+CT | 1457 | 3226 | 1769 | 800 | + |
| 5 | NG+MG | 1918 | 4023 | 2105 | | + |
| 6 | CT+MG | 3457 | 4121 | 664 | | - |
| 7 | NG+CT+MG | 3535 | 5896 | 2361 | | + |
| 8 | NTC | 125 | 134 | 9 | | - |

[1] Target is genomic DNA of *Mycoplasma genitalium* (MG), *Chlamydia trachomatis* (CT), and *Neisseria gonorrhoeae* (NG). NTC represents No Target Control.
[2] End-RFU represents relative fluorescence units at 50th cycle.
[3] End-△RFU represents the value obtained by subtracting the RFU at 72°C from that at 60°C
[4] Threshold is a threshold value for distinguishing the presence or absence of NG.

DETECTION OF TARGET NUCLEIC ACID SEQUENCES USING DIFFERENT DETECTION TEMPERATURES

CROSS REFERENCE TO RELATED APPLICATIONS

This application claims the priority of PCT/KR2014/012074, filed on Dec. 9, 2014, which claims priority to PCT/KR2014/006714, filed on Jul. 23, 2014, which claims priority to PCT/KR2014/004173, filed on May 9, 2014, which claims priority to U.S. Provisional Patent Application No. 61/979,545, filed on Apr. 15, 2014, which claims priority to Korean Patent Application No. 10-2014-0037310, filed Mar. 28, 2014, the entire contents of each of which are hereby incorporated in total by reference.

SEQUENCE LISTING

This application incorporates by reference the Sequence Listing contained in an ASCII text file named "361406_00033_SeqList.txt" submitted via EFS-Web. The text file was created on Sep. 2, 2016, and is 5 kb in size.

BACKGROUND OF THE INVENTION

Field of the Invention

The present invention relates to detection of target nucleic acid sequences using different detection temperatures.

Description of the Related Art

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v. 14 Mar. 1996), HyBeacon method (French D J et al., Mol. Cell Probes, 15(6):363-374(2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

The conventional real-time detection technologies described above detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using $T_m$ difference permits to detect a plurality of target nucleic acid sequences even a single type of label. However, the melting analysis has serious shortcomings in that its performance time is longer than real-time technologies and design of probes with different $T_m$ values becomes more difficult upon increasing target sequences.

Accordingly, where novel methods or approaches being not dependent on melting analysis for detecting a plurality of target nucleic acid sequences using a single type of label in a single reaction vessel and a single type of detector are developed, they enable to detect a plurality of target nucleic acid sequences with dramatically enhanced convenience, cost-effectiveness and efficiency. In addition, the combination of the novel methods with other detection methods (e.g., melting analysis) would result in detection of a plurality of target nucleic acid sequences using a single type of label in a single reaction vessel with dramatically enhanced efficiency.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel methods for detecting a plurality of target nucleic acid sequences using a single type of label in a single reaction vessel and a single type of detector. As a result, we have found that signals for target nucleic acid sequences are obtained at adjusted detection temperatures and then detection results are suitably interpreted, thereby enabling to detect a plurality of target nucleic acid sequences using a single type of label in a single reaction vessel and a single type of detector with dramatically enhanced convenience, cost-effectiveness and efficiency.

Accordingly, it is an object of this invention to provide a method and a kit for detecting two target nucleic acid sequences in a sample using different detection temperatures.

It is another object of this invention to provide a method and a kit for SNP genotyping of a nucleic acid sequence in a sample using different detection temperatures.

It is still another object of this invention to provide a method and a kit for detecting at least three target nucleic acid sequences in a sample using different detection temperatures.

It is further object of this invention to provide a method and a kit for detecting two target nucleic acid sequences in a sample using different detection temperatures and melting analysis.

It is still further object of this invention to provide a method and a kit for detecting at least three target nucleic acid sequences in a sample using detection temperature analysis and melting analysis.

It is another object of this invention to provide a computer readable storage medium containing instructions to configure a processor to perform a method for determining the presence of two target nucleic acid sequences in a sample using different detection temperatures.

It is still another object of this invention to provide a device for detecting a target nucleic acid sequence in a sample using different detection temperatures.

It is further object of this invention to provide a computer program to be stored on a computer readable storage medium to configure a processor to perform a method for determining the presence of two target nucleic acid sequences in a sample.

It is still further object of this invention to provide a computer readable storage medium containing instructions to configure a processor to perform a method for determining the presence of at least three target nucleic acid sequences in a sample using different detection temperatures.

Other objects and advantages of the present invention will become apparent from the detailed description to follow taken in conjugation with the appended claims and drawings.

BRIEF DESCRIPTION OF THE DRAWINGS

FIG. 1b represents determination of the presence of the target nucleic acid sequences having a relatively low detection temperature by a ratio between the signal at the relatively high detection temperature and the signal at the relatively low detection temperature.

FIGS. 1d and 1e represent determination of the presence of the target nucleic acid sequences having a relatively low detection temperature by difference between the signal at the relatively high detection temperature and the signal at the relatively low detection temperature, wherein the signal at the relatively high detection temperature is modified to a threshold value and used to obtain the difference.

FIG. 2b represents determination of the presence of the target nucleic acid sequences having a relatively low detection temperature by a ratio between the signal at the relatively high detection temperature and the signal at the relatively low detection temperature.

FIGS. 2d and 2e represent determination of the presence of the target nucleic acid sequences having a relatively low detection temperature by difference between the signal at the relatively high detection temperature and the signal at the relatively low detection temperature, wherein the signal at the relatively high detection temperature is modified to a threshold value and used to obtain the difference.

FIG. 4b represents SNP genotyping by using a ratio between the signal at the relatively high detection temperature and the signal at the relatively low detection temperature.

FIG. 5d represents End-ΔRFUs calculated by using the RFU values of the end points at 95° C. and 72° C. for the determination of the presence of CT genomic DNA.

FIG. 5e represents End-ΔRFUs calculated by using the RFU values of the end points at 72° C. and 60° C. for the determination of the presence of NG genomic DNA.

DETAILED DESCRIPTION OF THIS INVENTION

Figure 1A:
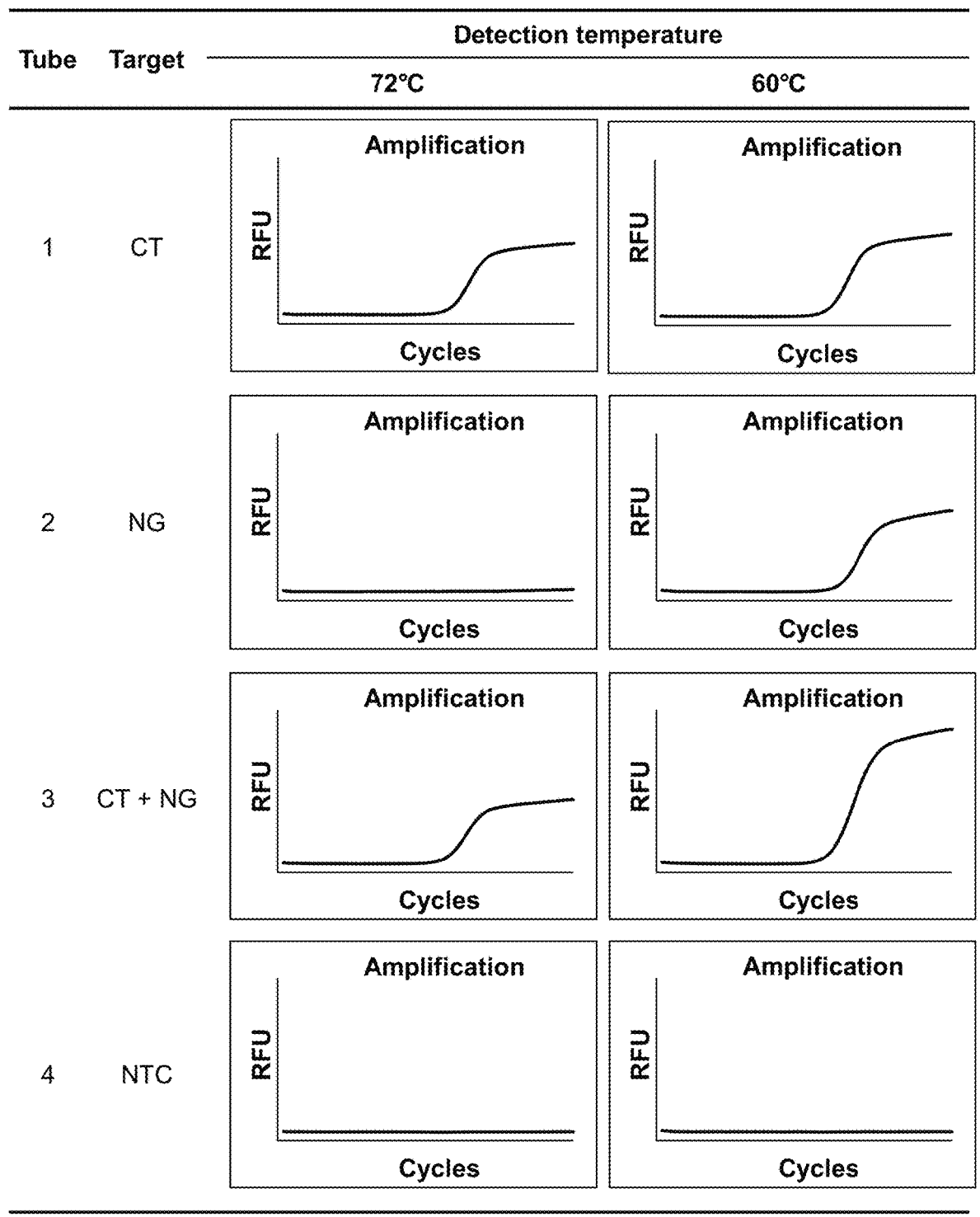
FIG. 1a represents the detection results of the present invention using different detection temperatures to detect a target nucleic acid sequence (genome DNA of *Chlamydia trachomatis*, CT) having a relatively high detection temperature (72° C.), a target nucleic acid sequence (genome DNA of *Neisseria gonorrhoeae*, NG) having a relatively low detection temperature (60° C.) and their combination. The signals for CT and NG were generated by PTOCE real-time PCR method.

The most prominent feature of the present invention is to detect a plurality of target nucleic acid sequences by using a single type of label and a single type of detector in a signal reaction vessel. The present invention employing different detection temperatures enables to detect a plurality of target nucleic acid sequences even with a single type of label in a single reaction vessel. The elements of the present invention are selected in compliance with the feature of the present invention and fabricated into a surprising process for detect target nucleic acid sequences.

Conventional real-time PCR methods require two types of fluorescent labels or melting analysis for detection of two target nucleic acid sequences in a single reaction vessel.

The present invention permits real-time PCR protocols to detect two target nucleic acid sequences by using a single type of fluorescent label in a single reaction vessel. Alternatively, the present invention enables to detect two target nucleic acid sequences by detecting one of two target nucleic acid sequences by real-time PCR and the other by melting analysis.

The present invention employs our findings that detection of signals is adjustable by temperatures in accordance with signal-generating means for target nucleic acid sequences.

For example, where signal-generating means by hybridization of a probe with a target nucleic acid sequence is used for detection of a first target nucleic acid sequence, a temperature at which the probe is hybridized with the first target nucleic acid sequence permits to generate and detect signals indicative of the presence of the first target nucleic acid sequence. In contrast, a temperature at which the probe is not hybridized with the first target nucleic acid sequence permits to generate and detect no signal. In this regard, it would be recognized that there are temperatures at which the signal is generated and temperatures at which the signal is not generated, depending on the signal-generating means.

In such signal-generating means, the temperatures at which the probe is hybridized with the first target nucleic acid sequence can be served as a detection temperature for the first target nucleic acid sequence. The temperatures at which the probe is not hybridized with the first target nucleic acid sequence cannot be served as a detection temperature.

Where probe hybridization is also used for detection of a second target nucleic acid sequence, its detection temperature may be determined in considering the fact that there is a temperature range to generate or not generate signals.

Where the $T_m$ value of the probe used for detection of the second target nucleic acid sequence is lower than that of the probe for detection of the first target nucleic acid sequence, the signal for the first target nucleic acid sequence can be detected at a relatively higher temperature wherein the signal for the second target nucleic acid sequence will not be generated. In other words, there is difference in temperatures to generate and detect signals between the two signal-generating means for the two target nucleic acid sequences.

Where the two target nucleic acid sequences co-exist in a sample, there is a temperature range enabling to generate signal for the first target nucleic acid sequence and not to generate signal for the second target nucleic acid sequence. Meanwhile, at a temperature range lower than the temperature range, signals for the two target nucleic acid sequences are generated.

Considering the two temperature ranges, a detection temperature may be determined for each of the target nucleic acid sequences. A relatively high detection temperature can be selected from the former temperature range, and the relatively high detection temperature is assigned to the first target nucleic acid sequence. A relatively low detection temperature can be selected from the latter temperature range, and the relatively low detection temperature is assigned to the second target nucleic acid.

According to the present invention, the signal at the relatively high detection temperature is measured to determine the presence of the first target nucleic acid sequence. According to the present invention, the detection at the relatively high detection temperature allows a method determining the presence of the first target nucleic acid sequence.

The important technical feature of the present invention is to unveil the signal detected at the relatively low detection temperature for determining the presence of the second target nucleic acid sequence having the relatively low detection temperature, by using both the signal at the relatively high detection temperature and the signal at the relatively low detection temperature.

Alternatively, the present inventors have contemplated that the first target nucleic acid sequence may be detected at the relatively high detection temperature by using different detection temperatures and the second target nucleic acid sequence may be detected by melting analysis as another signal generation approach. A signal-generating means used for melting analysis may provide a signal at a certain temperature during the real-time detection process. Therefore, even when one of two target nucleic acid sequences is detected by melting analysis, the two target nucleic acid sequences are required to have different detection temperatures from each other.

The present invention can be embodied to various aspects as follows:
(a) Detection of two target nucleic acid sequences in a sample using different detection temperatures;
(b) SNP genotyping of a nucleic acid sequence in a sample using different detection temperatures;
(c) Detection of at least three target nucleic acid sequences in a sample using different detection temperatures;
(d) Detection of two target nucleic acid sequences in a sample using different detection temperatures and melting analysis; and
(e) Detection of at least three target nucleic acid sequences in a sample using detection temperature analysis and melting analysis.

I. Detection of Two Target Nucleic Acid Sequences in a Sample Using Different Detection Temperatures In one aspect of this invention, there is provided a method for detecting two target nucleic acid sequences in a sample using different detection temperatures, comprising:
(a) incubating the sample with two signal-generating means for detection of the two target nucleic acid sequences in a single reaction vessel and detecting a generated signal by using a single type of detector; wherein each of the target nucleic acid sequences is detected by a corresponding signal-generating means; wherein one of the two target nucleic acid sequences has a relatively high detection temperature and the other has a relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; wherein signals to be generated by the two signal-generating means are not differentiated by the single type of detector; wherein the detection is performed at both the relatively high detection temperature and the relatively low detection temperature; and (b) determining the presence of the two target nucleic acid sequences by the signals detected in the step (a); wherein (i) the presence of the target nucleic acid sequence having the relatively high detection temperature is determined by the signal detected at the relatively high detection temperature and (ii) the presence of the target nucleic acid sequence having the relatively low detection temperature is determined by a difference between the signal detected at the relatively high detection temperature and the signal detected at the relatively low detection temperature.

According to conventional real-time PCR methods using amplification curves, it is common knowledge in the art that a plurality of target nucleic acid sequences cannot be differentially detected by use of signal-generating means providing undistinguishable identical signals.

The present invention overcomes limitations associated with the common knowledge in the art and leads to unexpected results to detect target nucleic acid sequences in greatly improved manner.

The present invention will be described in more detail as follows:

Step (a): Incubation with Signal-Generating Means and Signal Detection

Firstly, the sample to be analyzed is incubated with two signal-generating means for detection of the two target nucleic acid sequences in a single reaction vessel and then a generated signal is detected by using a single type of detector. Signals to be generated by the two signal-generating means are not differentiated by the single type of detector.

The present invention utilizes signal-generating means for generating signals for target nucleic acid sequences. Each of the target nucleic acid sequences is detected by a corresponding signal-generating means. The term used herein "signal-generating means" refers to any material used in generation of signals indicating the presence of target nucleic acid sequences, for example including oligonucleotides, labels and enzymes. Alternatively, the term used herein "signal-generating means" can be used to refer to any methods using the materials for signal generation.

According to an embodiment of this invention, incubation is preformed in the conditions allowing a signal generation by the signal-generation means. Such conditions include temperatures, salt concentrations and pH of solutions.

Examples of the oligonucleotides serving as signal-generating means include oligonucleotides to be specifically hybridized with target nucleic acid sequences (e.g., probes and primers); where probes or primers hybridized with target nucleic acid sequences are cleaved to release a fragment, the oligonucleotides serving as signal-generating means include capture oligonucleotides to be specifically hybridized with the fragment; where the fragment hybridized with the capture oligonucleotide is extended to form an extended strand, the oligonucleotides serving as signal-generating means include oligonucleotides to be specifically hybridized with the extended strand; the oligonucleotides serving as signal-generating means include oligonucleotides to be specifically hybridized with the capture oligonucleotide; and the oligonucleotides serving as signal-generating means include combinations thereof.

While a signal generation principle is the same, the signal generating means comprising different sequences of oligonucleotides used may be considered different from each other.

The label may be linked to oligonucleotides or may be in the free form. The label may be incorporated into extended products during an extension reaction.

Where the cleavage of oligonucleotides is used in signal generation, examples of the enzyme include 5'-nuclease and 3'-nuclease, particularly nucleic acid polymerase having 5'-nuclease activity, nucleic acid polymerase having 3'-nuclease activity or FEN nuclease.

In the present invention, signals may be generated by using various materials described above in various fashions.

According to an embodiment, at least one of the two signal-generating means is a signal-generating means to generate a signal in a dependent manner on the formation of a duplex.

According to an embodiment, the signal-generating means for each of the target nucleic acid sequences are signal-generating means to generate a signal in a dependent manner on the formation of a duplex.

According to an embodiment, the duplex includes a double stranded target nucleic acid sequence.

The expression used herein "generate a signal in a dependent manner on the formation of a duplex" in conjunction with signal-generating means refers to that signal to be detected is provided being dependent on association or dissociation of two nucleic acid molecules. The expression includes that a signal is provided by a duplex (e.g. a detection oligonucleotide with a label and a nucleic acid sequence) formed being dependent on the presence of a target nucleic acid sequence. In addition, the expression includes that a signal is provided by inhibition of hybridization of a duplex (e.g. a detection oligonucleotide with a label and a nucleic acid sequence) wherein the inhibition is caused by the formation of another duplex.

Particularly, the signal is generated by the formation of a duplex between a target nucleic acid sequence and a detection oligonucleotide specifically hybridized with the target nucleic acid sequence.

The term used herein "detection oligonucleotide" is an oligonucleotide which is involved in generation of signal to be detected. According to an embodiment of the present invention, the detection oligonucleotide includes an oligonucleotide which is involved in an actual signal generation. For example, the hybridization or non-hybridization of a detection oligonucleotide to another oligonucleotide (e.g. a target nucleic acid sequence or an oligonucleotide comprising a nucleotide sequence complementary to the detection oligonucleotide) determines the signal generation.

According to an embodiment of the present invention, the detection oligonucleotide comprises at least one label.

The signal by the formation of a duplex between a target nucleic acid sequence and the detection oligonucleotide may be generated by various methods, including Scorpion method (Whitcombe et al, Nature Biotechnology 17:804-807 (1999)), Sunrise (or Amplifluor) method (Nazarenko et al, Nucleic Acids Research, 25(12):2516-2521 (1997), and U.S. Pat. No. 6,117,635), Lux method (U.S. Pat. No. 7,537,886), Plexor method (Sherrill C B, et al., Journal of the American Chemical Society, 126:4550-45569 (2004)), Molecular Beacon method (Tyagi et al, Nature Biotechnology v. 14 Mar. 1996), HyBeacon method (French D J et al., Mol. Cell Probes, 15(6):363-374(2001)), adjacent hybridization probe method (Bernard, P. S. et al., Anal. Biochem., 273:221(1999)) and LNA method (U.S. Pat. No. 6,977,295).

Particularly, the signal is generated by a duplex formed in a dependent manner on cleavage of a mediation oligonucleotide specifically hybridized with the target nucleic acid sequence.

The term used herein "mediation oligonucleotide" is an oligonucleotide which mediates production of a duplex not containing a target nucleic acid sequence.

According to an embodiment of the present invention, the cleavage of the mediation oligonucleotide per se does not generate signal and a fragment formed by the cleavage is involved in successive reactions for signal generation following hybridization and cleavage of the mediation oligonucleotide.

According to an embodiment, the hybridization or cleavage of the mediation oligonucleotide per se does not generate signal.

According to an embodiment of the present invention, the mediation oligonucleotide includes an oligonucleotide which is hybridized with a target nucleic acid sequence and cleaved to release a fragment, leading to mediate the production of a duplex. Particularly, the fragment mediates a production of a duplex by an extension of the fragment on a capture oligonucleotide.

According to an embodiment of the present invention, the mediation oligonucleotide comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence.

According to an embodiment of the present invention, the cleavage of a mediation oligonucleotide release a fragment and the fragment is specifically hybridized with a capture oligonucleotide and extended on the capture oligonucleotide.

According to an embodiment of the present invention, a mediation oligonucleotide hybridized with target nucleic acid sequences is cleaved to release a fragment and the fragment is specifically hybridized with a capture oligonucleotide and the fragment is extended to form an extended strand, resulting in formation of a extended duplex between the extended stand and the capture oligonucleotide providing a signal indicating the presence of the target nucleic acid sequence.

According to an embodiment of the present invention, where a third oligonucleotide comprising a hybridizing nucleotide sequence complementary to the extended strand is used, the hybridization of the third oligonucleotide and the extended strand forms other type of a duplex providing a signal indicating the presence of the target nucleic acid sequence.

According to an embodiment of the present invention, where a third oligonucleotide comprising a hybridizing nucleotide sequence complementary to the capture oligonucleotide is used, the formation of a duplex between the third oligonucleotide and the capture oligonucleotide is inhibited by the formation of the duplex between the extended strand and the capturing oligonucleotide, leading to provide a signal indicating the presence of the target nucleic acid sequence.

According to an embodiment of the present invention, the fragment, the extended strand, the capture oligonucleotide, the third oligonucleotide or combination of them can work as the detection oligonucleotide.

The signal by the duplex formed in a dependent manner on cleavage of the mediation oligonucleotide may be generated by various methods, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

With referring to terms disclosed in the above references, the corresponding examples of the oligonucleotides are as follows: a mediation oligonucleotide is corresponding to a PTO (Probing and Tagging Oligonucleotide), a capture oligonucleotide to a CTO (Capturing and Templating Oligonucleotide), and a third oligonucleotide to SO (Signaling Oligonucleotide) or HO (Hybridization Oligonucleotide), respectively. SO, HO, CTO, extended strand or their combination can take a role as a detection oligonucleotide.

The signal by the duplex formed in a dependent manner on cleavage of the mediation oligonucleotide includes the signal provided by inhibition of the formation of other duplex by the duplex formed in a dependent manner on cleavage of the mediation oligonucleotide (e.g. PCE-NH).

For example, where the signal by the duplex formed in a dependent manner on cleavage of the mediation oligonucleotide is generated by PTOCE method, the signal-generating means comprises an upstream oligonucleotide and a PTO (Probing and Tagging Oligonucleotide) comprising a hybridizing nucleotide sequence complementary to the target nucleic acid sequence, a CTO (Capturing and Templating Oligonucleotide), suitable label and a template-dependent nucleic acid polymerase having 5' nuclease activity. The PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence. The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The particular example of the signal generation by PTOCE method comprises the steps of:
(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; and (d) performing an extension reaction using the resultant of the step (c) and a template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; wherein the extended duplex provides a target signal by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (e) detecting the extended duplex by measuring the target signal at a predetermined temperature that the extended duplex maintains its double-stranded form, whereby the presence of the extended duplex indicates the presence of the target nucleic acid sequence. In this case, the method further comprises repeating all or some of the steps (a)-(e) with denaturation between repeating cycles.

In the phrase "denaturation between repeating cycles", the term "denaturation" means to separate a double-stranded nucleic acid molecule to a single-stranded nucleic acid molecule.

In the step (a) of PTOCE method, a primer set for amplification of the target nucleic acid sequence may be used instead of the upstream oligonucleotide. In this case, the method further comprises repeating all or some of the steps (a)-(e) with denaturation between repeating cycles.

The PTOCE method can be classified as a process in which the PTO fragment hybridized with the CTO is extended to form an extended strand and the extended strand is then detected. The PTOCE method is characterized that the formation of the extended strand is detected by using the duplex between the extended strand and the CTO.

There is another approach to detect the formation of the extended strand. For example, the formation of the extended strand may be detected by using an oligonucleotide specifically hybridized with the extended strand (e.g., PCE-SH method).

In this method, the signal may be provided from (i) a label linked to the oligonucleotide specifically hybridized with the extended strand, (ii) a label linked to the oligonucleotide specifically hybridized with the extended strand and a label linked to the PTO fragment, (iii) a label linked to the oligonucleotide specifically hybridized with the extended strand and a label incorporated into the extended strand during the extension reaction, or (iv) a label linked to the oligonucleotide specifically hybridized with the extended strand and an intercalating dye. Alternatively, the signal may be provided from (i) a label linked to the extended strand or (ii) an intercalating dye.

Alternatively, the detection of the formation of the extended strand is performed by another method in which inhibition of the hybridization between the CTO and an oligonucleotide being specifically hybridizable with the CTO is detected (e.g. PCE-NH method). Such inhibition is considered to be indicative of the presence of a target nucleic acid sequence. The signal may be provided from (i) a label linked to the oligonucleotide being hybridizable with the CTO, (ii) a label linked to the CTO, (iii) a label linked to the oligonucleotide being hybridizable with the CTO and a label linked to the CTO, or (iv) an intercalating label.

According to an embodiment, the oligonucleotide being specifically hybridizable with the CTO has an overlapping sequence with the PTO fragment.

According to an embodiment, the detection oligonucleotide includes the oligonucleotide being specifically hybridizable with the extended strand (e.g., PCE-SH method) and oligonucleotide being specifically hybridizable with the CTO (e.g. PCE-NH method). According to an embodiment, the detection oligonucleotide includes the extended strand produced during a reaction or CTO.

The PTOCE-based methods commonly involve the formation of the extended strand depending on the presence of a target nucleic acid sequence. The term "PTOCE-based method" is used herein to intend to encompass various methods for providing signals comprising the formation of an extended strand through cleavage and extension of PTO.

The example of signal generation by the PTOCE-based methods comprises the steps of: (a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended to form an extended strand; and (e) detecting the formation of the extended strand by detecting signal generated dependent on the presence of the extended strand. In the step (a), a primer set for amplification of the target nucleic acid sequence may be used instead of the upstream oligonucleotide. In this case, the method further comprises repeating all or some of the steps (a)-(e) with denaturation between repeating cycles.

According to an embodiment, the signal generated by the formation of a duplex includes signals induced by hybridization of the duplex (e.g., hybridization of the duplex per se, or hybridization of a third oligonucleotide) or by inhibition of hybridization of a third oligonucleotide due to the formation of a duplex.

According to an embodiment, the signal-generating means for each of the target nucleic acid sequences are a signal-generating means by formation of a duplex in a dependent manner on cleavage of a mediation oligonucleotide specifically hybridized with the target nucleic acid sequence.

According to an embodiment, at least one of the two signal-generating means is a signal-generating means to generate a signal in a dependent manner on cleavage of a detection oligonucleotide.

Particularly, the signal is generated by hybridization of the detection oligonucleotide with a target nucleic acid sequence and then cleavage of the detection oligonucleotide.

The signal by hybridization of the detection oligonucleotide with a target nucleic acid sequence and then cleavage of the detection oligonucleotide may be generated by various methods, including TaqMan probe method (U.S. Pat. Nos. 5,210,015 and 5,538,848).

Where the signal is generated by TaqMan probe method, the signal-generating means includes a primer set for amplification of a target nucleic acid sequence, TaqMan probe having a suitable label (e.g., interactive dual label) and nucleic acid polymerase having 5'-nuclease activity. The TaqMan probe hybridized with a target nucleic acid sequence is cleaved during target amplification and generates signal indicating the presence of the target nucleic acid sequence.

The particular example generating signal by TaqMan probe method comprises the step of: (a) hybridizing the primer set and TaqMan probe having a suitable label (e.g., interactive dual label) with the target nucleic acid sequence; (b) amplifying the target nucleic acid sequence by using the resultant of the step (a) and nucleic acid polymerase having 5'-nuclease activity, wherein the TaqMan probe is cleaved to release the label; and (c) detecting a signal generation from the released label.

Particularly, the signal is generated by cleavage of the detection oligonucleotide in a dependent manner on cleavage of a mediation oligonucleotide specifically hybridized with the target nucleic acid sequence.

According to an embodiment of the present invention, where a mediation oligonucleotide hybridized with target nucleic acid sequences is cleaved to release a fragment, the fragment is specifically hybridized with a detection oligonucleotide and the fragment induces the cleavage of the detection oligonucleotide.

According to an embodiment of the present invention, where a mediation oligonucleotide hybridized with target nucleic acid sequences is cleaved to release a fragment, the fragment is extended to cleave a detection oligonucleotide comprising a hybridizing nucleotide sequence complementary to the capture oligonucleotide.

The signal by cleavage of the detection oligonucleotide in a dependent manner on cleavage of the mediation oligonucleotide may be generated by various methods, including Invader assay (U.S. Pat. No. 5,691,142), PCEC (PTO Cleavage and Extension-Dependent Cleavage) method (WO 2012/134195) and a method described in U.S. Pat. No. 7,309,573. In particular, the method described in U.S. Pat. No. 7,309,573 may be considered as one of PTOCE-based methods using signal generation by cleavage, and in the method, the formation of the extended strand may be detected by detecting cleavage of an oligonucleotide specifically hybridized with the CTO by the formation of the extended strand. Invader assay forms a fragment by cleavage of a mediation oligonucleotide and induces successive cleavage reactions with no extension of the fragment.

According to an embodiment of the present invention, where the signal is generated in a dependent manner on cleavage of a detection oligonucleotide, the cleavage of the detection oligonucleotide induces signal changes or releases a labeled fragment to be detected.

Where a signal-generating means generates a signal simultaneously by cleavage of a detection oligonucleotide and by the formation of a duplex, the signal-generating means may be considered as a signal generating means providing signal by cleavage, so long as it is used to generate signal by cleavage.

According to an embodiment, the signal generation being dependent manner on cleavage of the detection oligonucleotide is used for the target nucleic acid sequence having the relatively high detection temperature. Where the signal is generated by cleavage of the detection oligonucleotide, a released label by the cleavage may be detected at any temperatures. Therefore, the signal generated by cleavage of the detection oligonucleotide may not be employed for the target nucleic acid sequence having the relatively low detection temperature requiring restricted detection temperatures.

According to an embodiment, the signal generation being dependent on cleavage of the detection oligonucleotide is used for solely one target nucleic acid sequence. Where the signal generation being dependent on cleavage of the detection oligonucleotide is used for both of the two target nucleic acid sequences, the two target nucleic acid sequences may not be differentially detected depending on detection temperatures.

According to the embodiment of this invention, the signal-generating means for the target nucleic acid sequence having the relatively high detection temperature is a signal-generating means by cleavage of a detection oligonucleotide, and the signal-generating means for the target nucleic acid sequence having the relatively low detection temperature is a signal-generating means by the formation of a duplex.

According to the embodiment of this invention, the signal-generating means for the target nucleic acid sequence having the relatively high detection temperature is a signal-generating means by cleavage of a detection oligonucleotide, and the signal-generating means for the target nucleic acid sequence having the relatively low detection temperature is a signal-generating means by formation of a duplex in a dependent manner on cleavage of a mediation oligonucleotide specifically hybridized with the target nucleic acid sequence.

According to an embodiment, the detection oligonucleotide comprises at least one label.

According to an embodiment of the present invention, the detection oligonucleotide may be composed of at least one oligonucleotide. According to an embodiment of the present invention, where the detection oligonucleotide is composed of a plurality of oligonucleotides, it may have a label in various manners. For instance, one oligonucleotide among a plurality of oligonucleotides may have at least one label, a plurality of oligonucleotides all may have at least one label, or one portion of oligonucleotides may have at least one label and the other portion may not have a label.

The signals generated by the two signal-generating means are not differentiated by a single type of detector. The term "signals not differentiated by a single type of detector" means that signals are not differentiated from each other by a single type of detector due to their identical or substantially identical signal properties (e.g., optical properties, emission wavelength and electrical signal). For example, where the same label (e.g., FAM) is used for two target nucleic acid sequences and a single type of detector for detection of emission wavelength from FAM is used, signals are not differentially detected.

The term used herein "a single type of signal" means signals providing identical or substantially identical signal properties (e.g., optical properties, emission wavelength and electrical signal). For example, FAM and CAL Fluor 610 provide different types of signals.

The term used herein "a single type of detector" means a detection means for a singly type of signal. In a detector comprising several channels (e.g., photodiodes) for several different types of signals, each channel (e.g., a photodiode) corresponds to "a single type of detector".

According to an embodiment of this invention, the two signal-generating means comprise an identical label and signals from the label are not differentiated by the single type of detector.

The label useful in the present invention includes various labels known in the art. For example, the label useful in the present invention includes a single label, an interactive dual label, an intercalating dye and an incorporating label.

The single label includes, for example, a fluorescent label, a luminescent label, a chemiluminescent label, an electrochemical label and a metal label. According to an embodiment, the single label provides a different signal (e.g., different signal intensities) depending on its presence on a double strand or single strand. According to an embodiment, the single label is a fluorescent label. The preferable types and binding sites of single fluorescent labels used in this invention are disclosed U.S. Pat. Nos. 7,537,886 and 7,348,141, the teachings of which are incorporated herein by reference in their entity. For example, the single fluorescent label includes JOE, FAM, TAMRA, ROX and fluorescein-based label. The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red(615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

In the signaling system comprising the reporter and quencher molecules, the reporter encompasses a donor of FRET and the quencher encompasses the other partner (acceptor) of FRET For example, a fluorescein dye is used as the reporter and a rhodamine dye as the quencher.

The interactive dual label may be linked to one strand of a duplex. Where the strand containing the interactive dual label leaves in a single stranded state, it forms a hairpin or random coil structure to induce quenching between the interactive dual label. Where the strand forms a duplex, the quenching is relieved. Alternatively, where the interactive dual label is linked to nucleotides adjacently positioned on the strand, the quenching between the interactive dual label occurs. Where the strand forms a duplex and then is cleaved, the quenching becomes relieved.

Each of the interactive dual label may be linked to each of two strands of the duplex. The formation of the duplex induces quenching and denaturation of the duplex induces unquenching. Alternatively, where one of the two stands is cleaved, the unquenching may be induced.

Exemplified intercalating dyes useful in this invention include SYBR™ Green I, PO-PRO™-1, BO-PRO™-1, SYTO™ 43, SYTO™ 44, SYTO™ 45, SYTOX™ Blue, POPO™-1, POPO™-3, BOBO™-1, BOBO™-3, LO-PRO™-1, JO-PRO™-1, YO-PRO™ 1, TO-PRO™ 1, SYTO™ 11, SYTO™ 13, SYTO™ 15, SYTO™ 16, SYTO™ 20, SYTO™ 23, TOTO™-3, YOYO™ 3, GelStar™ and thiazole orange. The intercalating dyes intercalate specifically into double-stranded nucleic acid molecules to generate signals.

The incorporating label may be used in a process to generate signals by incorporating a label during primer extension (e.g., Plexor method, Sherrill C B, et al., Journal of the American Chemical Society, 126:4550-45569(2004)). The incorporating label may be also used in a signal generation by a duplex formed in a dependent manner on cleavage of a mediation oligonucleotide hybridized with the target nucleic acid sequence.

The incorporating label may be generally linked to nucleotides. The nucleotide having a non-natural base may be also used.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and M/N (see U.S. Pat. No. 7,422,850).

Where the signal is generated by the PTOCE method, a nucleotide incorporated during the extension reaction may have a first non-natural base and the CTO may have a nucleotide having a second non-natural base with a specific binding affinity to the first non-natural base.

The term used herein "target nucleic acid", "target nucleic acid sequence" or "target sequence" refers to a nucleic acid sequence of interest for detection or quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA, random primers or target-specific primers may be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known or unknown sequences.

The term used herein "sample" refers to any cell, tissue, or fluid from a biological source, or any other medium that can advantageously be evaluated according to this invention, including virus, bacteria, tissue, cell, blood, serum, plasma, lymph, milk, urine, faeces, ocular fluid, saliva, semen, brain extracts, spinal cord fluid (SCF), appendix, spleen and tonsillar tissue extracts, amniotic fluid, ascitic fluid and non-biological samples (e.g., food and water). In addition, the sample includes natural-occurring nucleic acid molecules isolated from biological sources and synthetic nucleic acid molecules.

According to an embodiment of this invention, the step (a) is performed in a signal amplification process concomitantly with a nucleic acid amplification.

In the present invention, the signal generated by signal-generating means may be amplified simultaneously with target amplification. Alternatively, the signal may be amplified with no target amplification.

According to an embodiment of this invention, the signal generation is performed in a process involving signal amplification together with target amplification.

According to an embodiment of this invention, the target amplification is performed in accordance with PCR (polymerase chain reaction). PCR is widely employed for target amplification in the art, including cycles of denaturation of a target sequence, annealing (hybridization) between the target sequence and primers and primer extension (Mullis et al. U.S. Pat. Nos. 4,683,195, 4,683,202 and 4,800,159; Saiki et al., (1985) Science 230, 1350-1354). The signal may be amplified by applying the signal generation methods described above (e.g., TaqMan method and PTOCE-based methods) to the PCR process. According to an embodiment, the present invention provides signals by real-time PCR method. According to an embodiment, the amplification of the target nucleic acid sequence is performed by PCR (polymerase chain reaction), LCR (ligase chain reaction, see Wiedmann M, et al., "Ligase chain reaction (LCR)-overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):16911696(1992), EP 497272), NASBA (nucleic acid sequence-based amplification, see Compton, J. Nature 350(6313):912(1991)), TMA (Transcription-Mediated Amplification, see Hofmann W P et al., J Clin Virol. 32(4):289-93(2005); U.S. Pat. No. 5,888,779).) or RCA (Rolling Circle Amplification, see Hutchison C. A. et al., Proc. Natl Acad. Sci. USA. 102:1733217336(2005)).

The amplification methods described above may amplify target sequences through repeating a series of reactions with or without changing temperatures. The unit of amplification comprising the repetition of a series of reactions is expressed as a "cycle". The unit of cycles may be expressed as the number of the repetition or time being dependent on amplification methods.

For example, the detection of signals may be performed at each cycle of amplification, selected several cycles or end-point of reactions. According to an embodiment, where signals are detected at at least two cycles, the detection of signal in an individual cycle may be performed at all detection temperatures or some selected detection temperatures. According to an embodiment of this invention, the detection is performed at the relatively high detection temperature in odd numbered cycles and at the relatively high detection temperature in even numbered cycles. According to an embodiment of this invention, incubation is preformed in the conditions allowing target amplification well as signal generation by the signal-generation means.

According to an embodiment of this invention, the step (a) is performed in a signal amplification process without a nucleic acid amplification.

Where the signal is generated by methods including cleavage of an oligonucleotide, the signal may be amplified with no target amplification. For example, the step (a) may be performed with amplification of signals but with no amplification of target sequences in accordance with CPT method (Duck P, et al., Biotechniques, 9:142-148 (1990)), Invader assay (U.S. Pat. Nos. 6,358,691 and 6,194,149), PTOCE-based methods (e.g., PCE-SH method, PCE-NH method and PCEC method) or CER method (WO 2011/037306).

The signal amplification methods described above may amplify signals through repeating a series of reactions with or without changing temperatures. The unit of signal amplification comprising the repetition of a series of reactions is expressed as a "cycle". The unit of cycles may be expressed as the number of the repetition or time being dependent on amplification methods.

For example, the generation and detection of signals may be performed at each cycle of amplification, selected several cycles or end-point of reactions.

The amplification of the target nucleic acid sequence is accomplished by target amplification means including a primer set for amplification and nucleic acid polymerase.

According to an embodiment of the present invention, a nucleic acid polymerase having a nuclease activity (e.g. 5' nuclease activity or 3' nuclease activity) may be used. According to an embodiment of the present invention, a nucleic acid polymerase having a no nuclease activity may be used.

The nucleic acid polymerase useful in the present invention is a thermostable DNA polymerase obtained from a variety of bacterial species, including *Thermus aquaticus* (Taq), *Thermus thermophilus* (Tth), *Thermus filiformis, Thermis flavus, Thermococcus literalis, Thermus antranikiani, Thermus caldophilus, Thermus chliarophilus, Thermus flavus, Thermus igniterrae, Thermus lacteus, Thermus oshimai Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosipho africanus, Pyrococcus woesei, Pyrococcus horikoshi, Pyrococcus abyssi Pyrodictium occultum, Aquifex pyrophilus* and *Aquifex aeolieus*. Particularly, the thermostable DNA polymerase is Taq polymerase.

According to an embodiment of the present invention, the amplification of the target nucleic acid sequence is accomplished by an asymmetric PCR. The ratio of primers may be selected in consideration of cleavage or hybridization of downstream oligonucleotides.

During or after the incubation (reaction) of the sample with two signal-generating means to generate signal, the generated signal is detected by using a single type of detector.

One of the two target nucleic acid sequences has a relatively high detection temperature and the other has a relatively low detection temperature determined by the corresponding signal-generating means.

The expression used herein "a target nucleic acid sequence has a detection temperature determined by the corresponding signal-generating means" refers to that a target nucleic acid sequence is detectable at a detection temperature pre-assigned to the target nucleic acid sequence allowing to detect a generated signal from a signal-generating means designed to generate the signal at the detection temperature.

According to an embodiment of the present invention, one detection temperature determined by the corresponding signal-generating is assigned to one target nucleic acid sequence.

The relatively high detection temperature is a temperature capable of generating a signal for the target nucleic acid sequence having the relatively high detection temperature, and the relatively low detection temperature is a temperature capable of generating both of a signal for the target nucleic acid sequence having the relatively low detection temperature and a signal for the target nucleic acid sequence having the relatively high detection temperature.

One of features of the present invention is to determine differentially the presence of the two target nucleic acid sequences by detecting at different detection temperatures signals indicative of the presence of the two target nucleic acid sequences.

According to an embodiment, the detection temperatures for target nucleic acid sequences are predetermined in considering a temperature range to allow signal generation by the signal-generating means.

The present invention uses that there is a certain temperature range to allow signal generation in a dependent manner on signal-generating means.

For example, when a signal-generating means generates a signal upon hybridization (or association) between two nucleic acid molecules and do not generate a signal upon non-hybridization (or dissociation) between them, a signal is generated at temperatures allowing hybridization between two nucleic acid molecules, however, no signal is generated at temperatures failing to hybridize between two nucleic acid molecules. As such, there is a certain temperature range to allow signal generation (i.e., signal detection) and other temperature range not to allow signal generation. The temperature ranges are affected by the $T_m$ value of the hybrid of the two nucleic acid molecules employed in the signal-generation means.

Where the signal generation method using a released fragment with a label after cleavage is employed, the signal may be theoretically detected at any temperature (e.g., 30-99° C.).

A detection temperature is selected from the temperature range to allow signal generation by the signal generation mean.

The term "the detection temperature range" is used herein to particularly describe the temperature range to allow signal generation (i.e., signal detection).

Where there are different detection temperature ranges depending on signal-generating means for the two target nucleic acid sequences, a non-overlapped detection temperature range may be selected as the relatively high detection temperature. A target nucleic acid sequence detected by signal-generating means providing the relatively high detection temperature is determined as the target nucleic acid sequence having the relatively high detection temperature. An overlapped detection temperature range may be selected as the relatively low detection temperature. A target nucleic acid sequence detected by signal-generating means providing the relatively low detection temperature and not providing the relatively high detection temperature is determined as the target nucleic acid sequence having the relatively low detection temperature.

According to an embodiment, the non-overlap region and the overlap region may not be distinguishably differentiated from each other. For example, a signal provided by the target nucleic acid sequence having the relatively low detection temperature may be generated with much lower intensity at the relatively high detection temperature selected for the target nucleic acid sequence having the relatively high detection temperature. In such case, a false signal problem due to a signal provided by the target nucleic acid sequence having the relatively low detection temperature at the relatively high detection temperature may be overcome by suitably selecting a reference value for determining significance of signals detected at the relatively high detection temperature.

According to an embodiment, the detection temperatures may be predetermined in considering non-overlapped detection temperature range and overlapped detection temperature range among the detection temperatures.

According to an embodiment, the detection temperatures assigned to target nucleic acid sequences are different by at least 2° C., 3° C., 4° C., 5° C., 7° C., 8° C., 9° C., 10° C., 11° C., 12° C., 15° C. or 20° C. from each other.

According to the present invention, a temperature for detecting the presence of each of target nucleic acid sequences may be allocated in considering signal-generating means.

According to an embodiment of this invention, one of the two target nucleic acid sequences is assigned with a relatively high detection temperature and the other is assigned with a relatively low detection temperature, and then signal-generating means suitable for the detection temperatures are constructed, followed by performing the step (a).

According to an embodiment, the relatively high detection temperature and the relatively low detection temperature at which the detection is carried out may be predetermined. For example, the relatively high detection temperature and the relatively low detection temperature are predetermined as 72° C. and 60° C., respectively, and then signal-generating means suitable for the detection temperatures are constructed, followed by performing the step (a).

According to an embodiment, signal-generating means for the two target nucleic acid sequences are firstly constructed and then detection temperatures for the two target nucleic acid sequences are allocated, followed by performing the step (a).

According to an embodiment of this invention, when the signal-generating means generates a signal in a dependent manner on the formation of a duplex, the detection temperature is selected based on a $T_m$ value of the duplex.

According to an embodiment of this invention, when the signal-generating means generates a signal in a dependent manner on the formation of a duplex, the detection temperature is controllable by adjusting a $T_m$ value of the duplex.

For example, where the signal is generated by a detection oligonucleotide specifically hybridized with the target nucleic acid sequence (e.g., Lux probe, Molecular Beacon probe, HyBeacon probe and adjacent hybridization probe), the detection of the signal is successfully done at the predetermined temperature by adjusting the $T_m$ value of the oligonucleotide. Where Scorpion primer is used, the detection of the signal is successfully done at the predetermined temperature by adjusting the $T_m$ value of a portion to be hybridized with extended strand.

Where the signal is generated by the duplex formed dependent on the presence of the target nucleic acid sequence, the detection of the signal is successfully done at the predetermined temperature by adjusting the $T_m$ value of the duplex. For example, where the signal is generated by the PTOCE method, the detection of the signal is successfully done at the predetermined temperature by adjusting the $T_m$ value of the extended duplex formed by the extension of the PTO fragment on the CTO.

The PTOCE-based methods have advantages to readily adjust $T_m$ values of the duplex or a third hybrid whose hybridization is affected by the duplex.

According to an embodiment of this invention, when the signal-generating means generates a signal in a dependent manner on cleavage of a detection oligonucleotide, the detection temperature is arbitrarily selected. In other words, any temperature can be selected so long as the signal generated by cleavage of a detection oligonucleotide may be detected. As described above, where the signal is generated being dependent manner on cleavage of the detection oligonucleotide, the label released by the cleavage may be detected at various temperatures.

According to an embodiment, where the signal is generated being dependent manner on cleavage of the detection oligonucleotide, the detection temperature is selected to be a relatively highest detection temperature.

As discussed above, the detection temperature is determined in considering a detection temperature range depending on signal-generating means. Therefore, the signal detection at a certain detection temperature may be described as follows: the detection at the relatively high detection temperature is to detect the target nucleic acid sequence having the relatively high detection temperature, and the detection at the relatively low detection temperature is to detect both the target nucleic acid sequence having the relatively low detection temperature and the target nucleic acid sequence having the relatively high detection temperature.

For instance, where both signals for the target nucleic acid sequence having the relatively low detection temperature and the target nucleic acid sequence having the relatively high detection temperature are generated by the PTOCE method, the signal for the target nucleic acid sequence having the relatively high detection temperature is generated by an extended duplex having a $T_m$ value suitable for the relatively high detection temperature, and the signal for the target nucleic acid sequence having the relatively low detection temperature is generated by an extended duplex having a $T_m$ value suitable for the relatively low detection temperature. When the signal is detected at the relatively high detection temperature, the extended duplex having a $T_m$ value suitable for the relatively low detection temperature is dissociated to be in a single strand and therefore no signal is generated, thereby detecting only the signal for the target nucleic acid sequence having the relatively high detection temperature. When the signal is detected at the relatively low detection temperature, all of the extended duplex having a $T_m$ value suitable for the relatively high detection temperature and the extended duplex having a $T_m$ value suitable for the relatively low detection temperature have their duplex form, thereby detecting both of the signal for the target nucleic acid sequence having the relatively low detection temperature and the signal for the target nucleic acid sequence having the relatively high detection temperature.

In another example, where the signal for the target nucleic acid sequence having the relatively high detection temperature is generated by TaqMan method and the signal for the target nucleic acid sequence having the relatively low detection temperature is generated by the PTOCE method, the signal for the target nucleic acid sequence having the relatively high detection temperature is provided by a released fluorescent label and the signal for the target nucleic acid sequence having the relatively low detection temperature is provided by an extended duplex having a $T_m$ value suitable for the relatively low detection temperature. When the signal is detected at the relatively high detection temperature, the extended duplex having a $T_m$ value suitable for the relatively low detection temperature is dissociated to be in a single strand and therefore no signal is generated, thereby detecting only the signal from the released fluorescent label for the target nucleic acid sequence having the relatively high detection temperature. When the signal is detected at the relatively low detection temperature, not only the signal provided from the extended duplex having a $T_m$ value suitable for the relatively low detection temperature but also the signal from the released fluorescent label are detected, thereby detecting both of the signal for the target nucleic acid sequence having the relatively low detection temperature and the signal for the target nucleic acid sequence having the relatively high detection temperature.

The detector used in the present invention includes any means capable of detecting signals. For example, where fluorescent signals are used, photodiodes suitable in detection of the fluorescent signals may be employed as detectors.

The detection using a single type of detector means that the detection is performed by using a detect capable of single type of signal or using each channel (i.e., photodiode) of a detector carrying several channels (i.e., photodiodes).

According to an embodiment, the generation of signals includes "signal generation or extinguishment" and "signal increase or decrease" from labels.

Step (b): Determining the Presence of Target Nucleic Acid Sequences

Following the detection of the signal, the presence of the two target nucleic acid sequences is determined by the signal detected in the step (a).

The presence of the target nucleic acid sequence having the relatively high detection temperature is determined by the signal detected at the relatively high detection temperature. The presence of the target nucleic acid sequence having the relatively low detection temperature is determined by a difference between the signal detected at the relatively high detection temperature and the signal detected at the relatively low detection temperature.

The signals used for determination of target presence includes that various signal characteristics from the signal detection, e.g., signal intensity [e.g., RFU (relative fluorescence unit) value or in the case of performing amplification, RFU values at a certain cycle, at selected cycles or at end-point], signal change shape (or pattern) or $C_t$ value, or values obtained by mathematically processing the characteristics.

According to an embodiment of this invention, when an amplification curve is obtained by real-time PCR, various signal values (or characteristics) from the amplification curve may be selected used for determination of target presence (intensity, $C_t$ value or amplification curve data).

The characteristics of the signal obtained at the relatively high detection temperature per se may be used to determine the presence of the target nucleic acid sequence having the relatively high detection temperature.

Alternatively, a modified signal provided by mathematically processing the characteristics of the signal may be used to determine the presence of the target nucleic acid sequence having the relatively high detection temperature.

The characteristics of the signals at the relatively high detection temperature per se and the relatively low detection temperature per se may be used to obtain the difference between the signals at relatively high detection temperature and a relatively low detection temperature.

Alternatively, one or both of the signals at the relatively high detection temperature and the relatively low detection temperature may be modified by mathematically processing the characteristics of the signal and used to obtain the difference between the signals at relatively high detection temperature and a relatively low detection temperature.

According to an embodiment, the term "signal" with conjunction with the phrase "signals detected at relatively high detection temperature and a relatively low detection temperature" includes not only the signal obtained at the detection temperature per se but also a modified signal provided by mathematically processing the signal.

According to an embodiment, where the mathematical processing is done, the characteristics of the signal should be characteristics vulnerable to the mathematical processing. In certain embodiment, the mathematical processing includes calculation (e.g., addition, multiplication, subtraction and division) using signals or obtaining other values derived from signals. The signals used for determination of the presence of target nucleic acid sequences in the present invention generally are a significant signal. In other words, the signals are signal to be generated being dependent on the presence of target nucleic acid sequences. In the meantime, where the difference between the signal detected at the relatively high detection temperature and the signal detected at the relatively low detection temperature is calculated, signal without significance such as background signals may be used to calculate the difference. In this regard, it would be understood that the signals used for determination of the presence of target nucleic acid sequences encompass not only signals with significance but also signals without significance so long as they can be used to calculate the difference or involved in a determination process.

According to an embodiment, significance of signals detected may be determined using a threshold value. For example, a threshold value is predetermined from a negative control in considering background signals of detector, sensitivity or label used, and then the significance of signals from samples may be determined.

Where a signal (i.e., a significant signal) is detected at the relatively high detection temperature, it is determined that the target nucleic acid sequence having the relatively high detection temperature is present.

The signal with no significance may be also expressed herein by "absence of signal" or "no detection of signal".

The term used herein "by a signal" with conjunction to determination of the presence of target nucleic acid sequences means that the presence of target nucleic acid sequences is determined by directly or indirectly using or modifying signals generated from the signal-generating means, including using numerical values of signals or their modifications, using the presence/absence of signals and comparing the signal with a threshold. There is no intended distinction between the terms "by a signal" and "by using a signal", and these terms will be used interchangeably.

The term used herein "determination by a signal" with reference to determination of the presence of the target nucleic acid sequence having the relatively high detection temperature may include determining the presence of the target nucleic acid sequence having the relatively high detection temperature with considering significance of the signal detected at the relatively high detection temperature.

In this invention, the presence of the target nucleic acid sequence having the relatively low detection temperature is determined by the signal detected at the relatively high detection temperature and the signal detected at the relatively low detection temperature.

Where a signal is detected at the relatively low detection temperature, said signal per se does not permit to determine the presence of the target nucleic acid sequence having the relatively low detection temperature. The reason for those is that the signal for the target nucleic acid sequence having the relatively high detection temperature may be detected at the relatively low detection temperature.

The feature of the present invention is to employ the signal detected at the relatively high detection temperature for analyzing the signal detected at the relatively low detection temperature.

Interestingly, the present inventors have found that when signals indicating the presence of a single target nucleic acid sequence are detected in a single reaction vessel at predetermined two detection temperatures, there is a signal change in a certain pattern (rule).

For example, a signal change between a signal detected at the relatively high detection temperature and a signal detected at the relatively low detection temperature for a target nucleic acid sequence having the relatively high detection temperature shows a certain pattern (rule). For example, the intensities of the signals may be identical or substantially identical to each other or the intensities of the signals may be different from each other but in a certain range at the two detection temperatures.

The feature of the present invention is to adopt the findings to detection of target nucleic acid sequences.

Because signals for a target nucleic acid sequence in a single reaction vessel are detected with differing only detection temperatures (e.g. no change of amount of the target or no variation of buffer conditions), there is a certain pattern (rule) in a signal change between the two detection temperatures. Based on the certain pattern (rule) in the signal change, the signal detected at the relatively high detection temperature can be used for analyzing the signal detected at the relatively low detection temperature.

According to an embodiment, the present method is performed in a condition that permits a certain pattern (rule) in a signal change for a target nucleic acid sequence between the two detection temperatures.

According to an embodiment, the presence of the target nucleic acid sequence having the relatively low detection temperature is determined in such a manner that the signal detected at the relatively low detection temperature is analyzed by using the signal detected at the relatively high detection temperature in order to verify whether the signal detected at the relatively low detection temperature contains a signal provided by the target nucleic acid sequence having the relatively low detection temperature.

The analysis of the signal detected at the relatively low detection temperature by using the signal detected at the relatively high detection temperature may be conducted by obtaining a difference between the signal detected at the relatively high detection temperature and the signal detected at the relatively low detection temperature and then analyzing it.

According to an embodiment of this invention, the extent (or portion) of signal of the target nucleic acid sequence having the relatively low detection temperature among the signal detected at the relatively low detection temperature may be obtained under the principle by using the signal at the relatively high detection temperature.

According to an embodiment, the presence of the target nucleic acid sequence having the relatively low detection temperature is determined by a difference between the signal detected at the relatively high detection temperature and the signal detected at the relatively low detection temperature.

For example, (i) where only the target nucleic acid sequence having the relatively high detection temperature is present in the sample, signal is detected at both the relatively high detection temperature and the relatively low detection temperature. The signal detected at the relatively high detection temperature is likely to be different from that detected at the relatively low detection temperature. Such difference is very likely to be within a certain range because all conditions except for detection temperatures are common. Where the difference calculated for a sample falls within the certain range, the signal detected at the relatively low detection temperature is due to only the target nucleic acid sequence having the relatively high detection temperature. In other words, the target nucleic acid sequence having the relatively low detection temperature can be determined to be absent in the sample.

(ii) Where both the target nucleic acid sequence having the relatively high detection temperature and the target nucleic acid sequence having the relatively low detection temperature are present in a sample, signals are detected at both the relatively high detection temperature and the relatively low detection temperature. The difference between the signals becomes more distinguishable than the difference in the case (i) because the target nucleic acid sequence having the relatively low detection temperature is present. The presence of the target nucleic acid sequence having the relatively low detection temperature can be determined by using the difference.

(iii) Where only the target nucleic acid sequence having the relatively low detection temperature is present in a sample, signal is detected at the relatively low detection temperature and not at the relatively high detection temperature. No signal detection at the relatively high detection temperature indicates the absence of the target nucleic acid sequence having the relatively high detection temperature, such that the signal detected at the relatively low detection temperature can be recognized to be due to the target nucleic acid sequence having the relatively low detection temperature, whereby the presence of the target nucleic acid sequence having the relatively low detection temperature can be determined.

Alternatively, in the case (iii), the difference may be obtained by using signal without significance (e.g., background signal) detected at the relatively high detection temperature. In this alternative, the difference is very likely to be distinctly different from the difference in the case (i), whereby the presence of the target nucleic acid sequence having the relatively low detection temperature can be determined.

The difference between the signals detected at the detection temperatures may be obtained in accordance with a wide variety of approaches.

The term used herein "difference" with conjunction to "by (or using) the difference between the signals" includes not only a difference to be obtained by mathematically processing signals per se or modified signals but also a difference due to the presence and absence of signals. For example, the difference may be obtained by calculating the ratio or subtraction between the signal detected at the relatively high detection temperature and the signal detected at the relatively low detection temperature. Alternatively, the difference may be given by modifying a signal at a detection temperature and comparing with a signal at other detection temperature.

The difference between the signal detected at the relatively high detection temperature and the signal detected at the relatively low detection temperature may be expressed in various aspects. For example, the difference may be expressed as numerical values, the presence/absence of signal or plot with signal characteristics.

According to an embodiment of this invention, the difference between the signal detected at the relatively high detection temperature and the signal detected at the relatively low detection temperature comprises a difference to be obtained by mathematically processing the signal detected at the relatively high detection temperature and the signal detected at the relatively low detection temperature.

According to an embodiment of this invention, when the signal is not detected at the relatively high detection temperature, the determination of the presence of the target nucleic acid sequence having the relatively low detection temperature is made by the signal detected at the relatively low detection temperature with considering no detection of the signal at the relatively high detection temperature. This embodiment addresses that using a difference due to the presence and absence of signals in the two detection temperatures allows for the determination of the presence of the target nucleic acid sequence having the relatively low detection temperature.

According to an embodiment, a background signal detected at the relatively high detection temperature may be treated as "0" or "1" for calculating the difference.

According to an embodiment, where a minus value is obtained during calculation, it is converted to absolute value and used to obtain the difference According to an embodiment of this invention, the signal for the target nucleic acid sequence having the relatively high detection temperature is a calculation parameter to analyze the signal for the target nucleic acid sequence having the relatively low detection temperature.

The signals for determining the presence of the target nucleic acid sequence having the relatively high detection temperature and the difference between the signal detected at the relatively high detection temperature and the signal detected at the relatively low detection temperature may have different dimensions or units from each other or have same dimensions or units from each other.

The term used herein "determined by a difference" includes determined by occurrence/non-occurrence of a difference, determined by value or range of a difference with a numerical value and determined by a plotting result of the difference. Furthermore, "determined by a difference" includes obtaining a value (e.g. $C_T$) for the target nucleic acid having a relative low detection temperature on the basis of the difference.

The tem used herein "by a difference" with conjunction to determination of the presence of target nucleic acid sequences means that the presence of target nucleic acid sequences is determined by directly or indirectly using or modifying difference between signals, including using numerical values of a difference or its modifications, using the presence/absence of signals and comparing a difference with a threshold. There is no intended distinction between the terms "by a difference" and "by using a difference", and these terms will be used interchangeably.

The mathematical processing of the signals may be carried out by various calculation methods and their modifications.

According to an embodiment of this invention, the mathematical processing of the signals to obtain the difference between the signals is a calculation of a ratio of the signal detected at the relatively low detection temperature to the signal detected at the relatively high detection temperature. According to an embodiment of this to invention, the mathematical processing of the signals to obtain the difference between the signals is a calculation of a ratio of the signal detected at the relatively high detection temperature to the signal detected at the relatively low detection temperature.

The term used herein "ratio" means a relationship between two numbers. By using the ratio, the presence of the target nucleic acid sequence having the relatively low detection temperature may be determined. Where the ratio of the signal detected at the relatively low detection temperature to the signal detected at the relatively high detection temperature is significant, it becomes entitled as an indicator for the presence of the target nucleic acid sequence having the relatively low detection temperature. For instance, where the ratio of the end-point intensity of the signal detected at the relatively low detection temperature to the end-point intensity of the signal detected at the relatively high detection temperature is significant (e.g., increase in the end-point intensity), it indicates the presence of the target nucleic acid sequence having the relatively low detection temperature.

The mathematical processing may be carried out in various fashions.

The mathematical processing may be carried out by use of a machine. For example, the signals may be undergone a mathematical processing by a processor in a detector or real-time PCR device. Alternatively, the signals may be manually undergone a mathematical processing particularly according to a predetermined algorithm.

According to an embodiment of this invention, depending on approaches for obtaining the difference, a threshold may be employed to analyze whether the difference obtained is indicative of the presence of the target nucleic acid sequence having the relatively low detection temperature. For example, a threshold is predetermined with considering the difference obtained from a standard sample containing the target nucleic acid having the relatively high detection temperature and the target nucleic acid having the relatively low detection temperature. A negative control, sensitivity or label used may be further considered for determining the threshold.

According to an embodiment of this invention, depending on approaches for obtaining the difference, the presence of the target nucleic acid sequence having the relatively low detection temperature may be determined by using the difference obtained per se. For example, a signal at the relatively high detection temperature may be multiplied with a threshold and then the difference between the multiplied signal and a signal at the relatively low detection temperature may be obtained. Particularly, the threshold is predetermined with considering the difference obtained from a standard sample containing the target nucleic acid having the relatively high detection temperature and the target nucleic acid having the relatively low detection temperature.

According to an embodiment of this invention, a threshold is determined by user or automatically.

In an embodiment, where the difference between signals at the relatively high detection temperature and the relatively low detection temperature for the target nucleic acid sequence having the relatively high detection temperature becomes greater, it is more likely to reduce detection errors by using the threshold.

In an embodiment, where signals provided by the target nucleic acid sequence having the relatively high detection temperature have a pattern (or rule) showing little or no difference between the two detection temperatures, the signal detected at the relatively high detection temperature may be used without further modifications in either calculation of the difference or determination of the presence of the target nucleic acid sequence having the relatively low detection temperature using the difference.

In certain embodiment, where signals have a pattern (or rule) showing difference within a certain range, the signal at the relatively high detection temperature may be subject to modification reflecting the difference in determination of the presence of the target nucleic acid sequence.

The reference value is a value reflecting a pattern (rule) of a signal change in the difference temperatures.

According to an embodiment of this invention, the reference value is a value reflecting a pattern (or rule) of change in signals at two different detection temperatures for the target nucleic acid sequence having the relatively high detection temperature.

For example, where the signals at the relatively high detection temperature and the relatively low detection temperature for the target nucleic acid sequence having the relatively high detection temperature are identical or substantially identical and the extent of difference in the signals at the two detection temperatures is calculated by subtraction of the signals, the reference value is '0' for signals at the two detection temperatures for the target nucleic acid sequence having the relatively high detection temperature. As another example, where the extent of difference in the signals at the two detection temperatures is calculated by division of the signals, the reference value is '1' for signals at the two detection temperatures for the target nucleic acid sequence having the relatively high detection temperature.

In the meantime, where the signals at the relatively high detection temperature and the relatively low detection temperature for the target nucleic acid sequence having the relatively high detection temperature are different from each other and the extent of difference in the two signals is calculated by subtraction of the signals, the reference value is a positive value or negative value other than '0' for signals at the two detection temperatures for the target nucleic acid sequence having the relatively high detection temperature. As another example, where the extent of difference in the signals at the two detection temperatures is calculated by division of the signals, the reference value is above or below 1 other than '1' for signals at the two detection temperatures for the target nucleic acid sequence having the relatively high detection temperature.

In certain embodiment, where the signals at the relatively high detection temperature and the relatively low detection temperature for the target nucleic acid sequence having the relatively high detection temperature are different from each other, the extent of difference in the two signals falls within a certain range.

In certain embodiment, difference in signals at the relatively high detection temperature and the relatively low detection temperature provided by the target nucleic acid sequence having the relatively high detection temperature may be expressed through a reference value. In certain embodiment, the reference value for the case in which the signals at the relatively high detection temperature and the relatively low detection temperature provided by the target nucleic acid sequence having the relatively high detection temperature are different from each other may be different by more than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 12%, 15%, 20% or 30%, compared with the reference value for the case in which the two signals are the same.

In an embodiment, where the difference between signals at the relatively high detection temperature and the relatively low detection temperature for the target nucleic acid sequence having the relatively high detection temperature becomes greater, it is more advantageous to reduce detection errors in determination of the presence of the target nucleic acid sequence having the relatively low detection temperature by using the reference value for the target nucleic acid sequence having the relatively high detection temperature.

In certain embodiment, the reference value for the target nucleic acid sequence having the relatively high detection temperature may be used in determination of the presence of the target nucleic acid sequence having the relatively low detection temperature, where the reference value for the target nucleic acid sequence having the relatively high detection temperature calculated from the signals at the two detection temperatures is different by more than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 12%, 15%, 20% or 30% compared with the reference value for the case in which the two signals are the same.

According to an embodiment, where the comparison is performed to determine whether a reference value is used, the reference value is calculated by division of the signals. According to an embodiment, the method of calculating the reference value for determining whether the reference value is used may be the same or different from each other the method of calculating the reference value for detecting the target nucleic acid sequence.

According to an embodiment, a reference value is used to determine the presence of the target nucleic acid sequence having the relatively low detection temperature by a difference between the signal detected at the relatively high detection temperature and the signal detected at the relatively low detection temperature. Particularly, a reference value is related to the target nucleic acid sequence having the relatively high detection temperature.

According to an embodiment of this invention, the reference value may be employed to analyze whether the difference obtained is indicative of the presence of the target nucleic acid sequence having the relatively low detection temperature.

According to an embodiment of this invention, the reference value may be employed to obtain the difference between a signal at the relatively high and a signal at the relatively low detection temperature. For example, a signal at the relatively high detection temperature may be multiplied or divided with the reference value of the target nucleic acid sequence having the relatively high detection temperature and then the difference between the multiplied or divided signal and a signal at the relatively low detection temperature may be obtained. Another example, a signal at the relatively low detection temperature may be multiplied or divided with the reference value of the target nucleic acid sequence having the relatively high detection temperature and then the difference between the multiplied or divided signal and a signal at the relatively high detection temperature may be obtained.

According to an embodiment of this invention, a reference value is used for determining a threshold. According to an embodiment of this invention, a reference value is used as a threshold with or without a modification of the value. The terms used herein "threshold" and "reference value" for determining the presence of target nucleic acid sequences by analyzing the difference between signals may have the same value or meaning.

Alternatively, where the reference value is employed to obtain the difference between a signal at the relatively high and a signal at the relatively low detection temperature, a further threshold may be used to determine the significance of the difference, i.e. to determine whether the difference indicates the presence of the target nucleic acid having the relatively low detection temperature.

According to an embodiment, where the target nucleic acid sequence having the relatively high detection temperature is present, the reference value is used to determine the presence of the target nucleic acid sequence having the relatively low detection temperature.

The case in which the target nucleic acid sequence having the relatively high detection temperature is present includes a case in which a significant signal indicative of the presence of the target nucleic acid sequence having the relatively high detection temperature is detected.

According to an embodiment, where the target nucleic acid sequence having the relatively high detection temperature is absent, the reference value is optionally used to determine the presence of the target nucleic acid sequence having the relatively low detection temperature.

The case in which the target nucleic acid sequence having the relatively high detection temperature is absent includes a case in which a signal with similar intensity to a background signal is only detected.

According to an embodiment of this invention, the method uses a reference value, for determining the presence of the target nucleic acid sequence having the relatively low detection temperature, obtained by (i) incubating the target nucleic acid sequence having the relatively high detection temperature with a signal-generating means for detection of the target nucleic acid sequence having the relatively high detection temperature in a reaction vessel other than the reaction vessel in the step (a), (ii) detecting signals at both the relatively high detection temperature and the relatively low detection temperature, and (iii) then obtaining a difference between the signal detected at the relatively high detection temperature and the signal detected at the relatively low detection temperature.

According to an embodiment, the difference between the signal detected at the relatively high detection temperature and the signal detected at the relatively low detection temperature obtained in the above (iii) is a value and the value is used as a reference value with modification or without modification.

According to an embodiment, a reference value may be obtained by calculating the ratio or subtraction between the signal detected at the relatively high detection temperature and the signal detected at the relatively low detection temperature.

According to an embodiment of this invention, the reference value is obtained by calculating the ratio of the signal detected at the relatively low detection temperature to the signal detected at the relatively high detection temperature. According to an embodiment of this invention, the reference value is obtained by calculating the ratio of the signal detected at the relatively high detection temperature to the signal detected at the relatively low detection temperature.

According to an embodiment, calculation methods for difference of signals from a sample and difference for obtaining a reference value may be the same or different from each other. For instance, the former may be carried out by subtraction of the two signals and the latter by division of the two signals. Alternatively, the former and the latter all may be carried out by division of the two signals to obtain a ratio.

According to an embodiment of this invention, signal-generating means for the reference value may be the same as that for the detection of the target nucleic acid sequence.

For a target nucleic acid sequence, the reference values may be obtained in various reaction conditions including the amount of component (e.g. the target nucleic acid sequence, signal-generating means, enzymes, or dNTPs), buffer pH or reaction time. According to an embodiment of this invention, the reference value may be obtained under reaction conditions sufficient to provide a saturated signal at the reaction completion. According to an embodiment of this invention, the difference between the signals obtained in calculating the reference value has a certain range and the reference value is selected within the certain range or with referring to the certain range. According to an embodiment of this invention, the reference value may be selected with maximum or minimum value of the certain range or with referring to maximum or minimum value of the certain range. Particularly, the reference value may be modified in considering standard variation of the reference values obtained in various conditions, acceptable error ranges, specificity or sensitivity.

According to an embodiment of this invention, the reference values may be obtained in identical reaction conditions used for the sample including the components (enzymes or amplification primers if used), buffer pH, reaction process. According to an embodiment of this invention, the reference values may be obtained with a signal amplification process concomitantly with or without a nucleic acid amplification.

According to an embodiment of this invention, where there is a significant difference between the reference value and the difference obtained for determining the presence of the target nucleic acid sequence having the relatively low detection temperature, the target nucleic acid sequence having the relatively low detection temperature is then determined to be present. The reference value may be expressed with the same value type as the difference obtained for determining the presence of the target nucleic acid sequence having the relatively low detection temperature (e.g., ratio of end-point values of signal intensities).

In a particular example, where the ratio of the end-point value of the signal intensity detected at the relatively high detection temperature to the end-point value of the signal intensity detected at the relatively low detection temperature is 1.8 and the reference value is 1.1, it can be determined that there is a significant difference between the reference value and the difference obtained for determining the presence of the target nucleic acid sequence having the relatively low detection temperature. It indicates the presence of the target nucleic acid sequence having the relatively low detection temperature.

According to an embodiment, where the difference for determining the presence of the target nucleic acid sequence having the relatively low detection temperature is same or higher than the reference value, the target nucleic acid sequence having the relatively low detection temperature is then determined to be present.

According to an embodiment, where the difference for determining the presence of the target nucleic acid sequence having the relatively low detection temperature is same or lower than the reference value, the target nucleic acid sequence having the relatively low detection temperature is then determined to be present.

Alternatively, the reference value may be used to calculate the difference between the signal detected at the relatively high detection temperature and the signal detected at the relatively low detection temperature. For example, the difference for determining the presence of the target nucleic acid sequence having the relatively low detection temperature is calculated such a manner that the signal (e.g. RFU) detected at the relatively high detection temperature is multiplied (or divided) by the reference value of the target nucleic acid sequence having the relatively high detection temperature and then the multiplication (or division) result is subtracted with the signal (e.g. RFU) detected at the relatively low detection temperature. Where a difference is higher (or lower) than "0" or a predetermined value, the target nucleic acid sequence having the relatively low detection temperature can be determined to be present.

Another example, the difference for determining the presence of the target nucleic acid sequence having the relatively low detection temperature is calculated such a manner that the signal (e.g. RFU) detected at the relatively low detection temperature is multiplied (or divided) by the reference value of the target nucleic acid sequence having the relatively high detection temperature and then the multiplication (or division) result is subtracted with the signal (e.g. RFU) detected at the relatively high detection temperature. Where a difference is higher (or lower) than "0" or a predetermined value, the target nucleic acid sequence having the relatively low detection temperature can be determined to be present.

According to an embodiment, the predetermined value may take a role as a threshold.

According to an embodiment, the reference value is used to determine the presence of the target nucleic acid sequence having the relatively low detection temperature, when a signal for the target nucleic acid sequence having the relatively high detection temperature is detected or when a difference between the signals at the relatively high detection temperature and the relatively low detection temperature is obtained by mathematical process.

According to an embodiment, where signals are generated in a real-time manner associated with target amplification by PCR, the mathematical processing of the signals comprises calculations of the ratio of a signal intensity detected at the relatively high detection temperature to a signal intensity detected at the relatively low detection temperature at each amplification cycle. The calculation results are plotted against cycles and used for determination of the presence of the target nucleic acid sequence having the relatively low detection temperature.

According to an embodiment, where signals are generated in a real-time manner associated with target amplification by PCR, $C_t$ value is a signal for detection target.

The $C_t$ value of the target nucleic acid sequence having the relatively low detection temperature may be determined using the signals detected at the relatively high detection temperature and at the relatively low detection temperature, which is exemplified as follows: Firstly, a real-time PCR is performed for a sample to be analyzed and the signals detected at the relatively high detection temperature and at the relatively low detection temperature are obtained, followed by obtaining amplification curves of the two detection temperatures.

(a) In the detection at the relatively high detection temperature, where there is no $C_t$ value of the target nucleic acid sequence having the relatively high detection temperature, it can be determined that the target nucleic acid sequence having the relatively high detection temperature is not present. Then, the $C_t$ value of the target nucleic acid sequence having the relatively low detection temperature is calculated from the amplification curve obtained in relatively low detection temperature. Where the target nucleic acid sequence having the relatively low detection temperature is also absent, there is no $C_t$ value of the target nucleic acid sequence having the relatively low detection temperature.

(b) In the detection at the relatively high detection temperature, where there is $C_t$ value of the target nucleic acid sequence having the relatively high detection temperature, a ratio of the RFU value obtained at the relatively low detection temperature to the RFU value obtained at the relatively high detection temperature at the cycle showing the $C_t$ value is then calculated. Ratios of RFU values obtained at cycles following the cycle showing the $C_t$ value are also calculated. (i) Where all ratios of the RFU values are lower than a reference value (e.g. a value obtained using only the target nucleic acid sequence having the relatively high detection temperature as described above), the target nucleic acid sequence having the relatively low detection temperature is determined to be absent. Therefore, there is no $C_t$ value of the target nucleic acid sequence having the relatively low detection temperature. (ii) Where all ratios of the RFU values are higher than the reference value, $C_t$ value calculated from amplification curve obtained at the relatively low detection temperature is determined as $C_t$ value of the target nucleic acid sequence having the relatively low detection temperature. (iii) Where the ratio of the RFU values at the cycle showing the $C_t$ value is lower than the reference value and the ratio of the RFU values after a certain cycle are higher than the reference value, the certain cycle is determined as $C_t$ value of the target nucleic acid sequence having the relatively low detection temperature.

Where ratios calculated are the same as the reference value, the determination may be arbitrarily made. For example, the examples described above describe that the determination is made with considering whether the ratios are less than or no less than reference values. In addition, the determination may be made with considering whether the ratios are no more than or more than reference values.

The $C_t$ value of the target nucleic acid sequence having the relatively low detection temperature may be alternatively calculated as follows: the ratio of the RFU value obtained at the relatively low detection temperature to the RFU value obtained at the relatively high detection temperature is calculated for each cycle; and $C_t$ value is then calculated with consideration of a threshold value.

The $C_t$ value of the target nucleic acid sequence having the relatively low detection temperature may be alternatively calculated as follows: The RFU value obtained at the relatively high detection temperature at each cycle is modified with a reference value of each cycle; the ratio of the RFU value obtained at the relatively low detection temperature to the modified RFU value is calculated for each cycle; and $C_t$ value is then calculated.

According to an embodiment of this invention, using the signal detected at the relatively high detection temperature comprises obtaining a qualifying value for determining the presence of the target nucleic acid sequence having the relatively high detection temperature and said using the difference comprises obtaining a qualifying value for determining the presence of the target nucleic acid sequence having the relatively low detection temperature.

According to an embodiment of this invention, using the difference comprises obtaining a qualifying value for determining the presence of the target nucleic acid sequence having the relatively low detection temperature, and the qualifying value is obtained by (i) mathematically processing the signal detected at the relatively high detection temperature and the signal detected at the relatively low detection temperature or (ii) using the signal detected at the relatively low detection temperature with considering no detection of the signal at the relatively high detection temperature when the signal is not detected at the relatively high detection temperature.

The qualifying values may be further mathematically processed to obtain modified values. The qualifying values are used to determine the presence of the two target nucleic acid sequences in the sample.

According to an embodiment, the single reaction vessel further comprises at least one additional set each of which contains additional two signal-generating means for detection of target nucleic acid sequences other than the two target nucleic acid sequences; wherein the signals generated by each set of two signal-generating means in the vessel are differentiated from each other and the signals are detected by different types of detectors, respectively. For example, where the two signal-generating means in the step (a) are labeled with FAM and the additional two signal-generating means are labeled with Quasar 570, the signals generated by FAM-labeled signal-generating means in the vessel are differentiated from the signals generated by Quasar 570- labeled signal-generating means and therefore two types of detectors are required to detect two different emission lights.

According to an embodiment of this invention, the two target nucleic acid sequences comprises a nucleotide variation and one of the two target nucleic acid sequences comprises one type of the nucleotide variation and the other comprises the other type of the nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

According to an embodiment of this invention, the nucleotide variation detected by the present invention is a SNP (single nucleotide polymorphism).

According to an embodiment of this invention, one of the SNP alleles has a relatively high detection temperature and the other has a relatively low detection temperature determined by the corresponding signal-generating means.

The advantages of the present invention become more prominent for detection of SNP.

Where a detection temperature for the wild type allele is the relatively high detection temperature, a detection temperature for the mutant allele is the relatively low detection temperature and the sample is mutant homozygous, a signal will be not detected at the relatively high detection temperature and a signal will be detected at the relatively high detection temperature. The sample will be determined to contain no wild type allele and contain mutant type allele. Meanwhile, even when a false signal at the relatively high detection temperature is generated for the mutant homozygote sample, calculating result of the difference between the signal detected at the relatively high detection temperature and the signal detected at the relatively low detection temperature for determining the presence of the SNP allele having the relatively low detection temperature permits to verify whether the signal detected at the relatively high detection temperature is a false positive signal or not. The reason is that a heterozygote for SNP comprises the wild type allele and the mutant allele in 1:1 ratio.

II. SNP Genotyping Using Different Detection Temperatures

In another aspect of this invention, there is provided a method for SNP genotyping of a nucleic acid sequence in a sample using different detection temperatures, comprising:
(a) incubating the sample comprising the nucleic acid sequence containing a SNP (single nucleotide polymorphism) site and a signal-generating means for detection of SNP alleles in a single reaction vessel and detecting a generated signal by using a single type of detector; wherein each of the SNP alleles is detected by a corresponding signal-generating means; wherein one of the SNP alleles has a relatively high detection temperature and the other has a relatively low detection temperature determined by the corresponding signal-generating means; wherein the relatively high detection temperature is a temperature capable of generating a signal for the SNP allele having the relatively high detection temperature and the relatively low detection temperature is a temperature capable of generating both of a signal for the SNP allele having the relatively low detection temperature and a signal for the SNP allele having the relatively high detection temperature; wherein signals to be generated by the signal-generating means are not differentiated by the single type of detector; wherein the detection is performed at both the relatively high detection temperature and the relatively low detection temperature; and
(b) determining a SNP genotype by a difference between the signal detected at the relatively high detection temperature and the signal detected at the relatively low detection temperature in the step (a).

Since the present invention follows in principle the first aspect of this invention described above, the common descriptions between them are omitted in order to avoid undue redundancy leading to the complexity of this specification. When referring to descriptions for the first aspect in order to describe this aspect, it should be noted that the step (b) of this aspect is, in part, different from the step (b) of the first aspect. Therefore, it would be understood to those skilled in the art that some descriptions for the first aspect may be directly applied to descriptions for the step (b) of this aspect and other descriptions with modifications may be applied to descriptions for the step (b) of this aspect.

Step (a): Incubation with Signal Generating Means and Signal Detection

Firstly, the sample comprising the nucleic acid sequence containing a SNP (single nucleotide polymorphism) site is incubated with a signal-generating means for detection of SNP alleles in a single reaction vessel and then a generated signal is detected by using a single type of detector. Signals to be generated by the signal-generating means are not differentiated by the single type of detector.

The nucleic acid sequence containing a SNP site may include a chromosome pair of human.

One of the SNP alleles has a relatively high detection temperature and the other has a relatively low detection temperature determined by the corresponding signal-generating means; wherein the relatively high detection temperature is a temperature capable of generating a signal for the SNP allele having the relatively high detection temperature and the relatively low detection temperature is a temperature capable of generating both of a signal for the SNP allele having the relatively low detection temperature and a signal for the SNP allele having the relatively high detection temperature.

According to an embodiment of this invention, the step (a) is performed in a signal amplification process concomitantly with a nucleic acid amplification.

According to an embodiment of this invention, the step (a) is performed in a signal amplification process without a nucleic acid amplification.

Step (b): Determining a SNP Genotype

Following the detection of the signal, SNP genotyping is determined by difference between the signal detected at the relatively high detection temperature and the signal detected at the relatively low detection temperature in the step (a).

The present invention allows for SNP genotyping only by using difference between the signal detected at the relatively high detection temperature and the signal detected at the relatively low detection temperature with no determining for the presence of the SNP allele having the relatively high detection temperature.

According to an embodiment, the difference is obtained by mathematically processing the signal detected at the relatively high detection temperature and the signal detected at the relatively low detection temperature.

According to an embodiment, the difference is obtained by calculating the ratio between the signals detected at the relatively high detection temperature and the signal detected at the relatively low detection temperature.

According to an embodiment, a background signal detected at the relatively high detection temperature is used to calculate the difference.

According to an embodiment, a background signal detected at the relatively high detection temperature may be treated as "0" or "1" for calculating the difference.

According to an embodiment, where a minus value is obtained during calculation, it is converted to absolute value and used to obtain the difference.

According to an embodiment of this invention, the step (b) for determining SNP genotype is performed with no determining the presence of the SNP allele having the relatively high detection temperature. SNP genotyping is performed by using the difference between the signal detected at the relatively high detection temperature and the signal detected at the relatively low detection temperature.

The reason for that no requirement for determining the presence of the SNP allele having the relatively high detection temperature is that there are three SNP genotypes, and a heterozygote for SNP comprises the wild type allele and the mutant allele in 1:1 ratio. By combining the reason with the principle of the present invention, SNP genotyping can be made with no determining the presence of the SNP allele having the relatively high detection temperature.

According to an embodiment of this invention, the homozygote sample containing the SNP allele having a relatively high detection temperature shows a difference (e.g. a ratio) within a certain range, the heterozygote sample shows a difference (e.g. a ratio) within another certain range and the homozygote sample containing the SNP allele having a relatively low detection temperature shows a difference (e.g. a ratio) within the other certain range.

According to an embodiment of this invention, the certain range for each SNP genotype may be related to a reference value for the each SNP genotype.

According to an embodiment of this invention, method uses at least one of the reference values for the homozygote composed of the SNP allele having a relatively high detection temperature, the homozygote composed of the SNP allele having a relatively low detection temperature and the heterozygote for determining a SNP genotype.

According to an embodiment of this invention, method uses all of the three reference values for determining a SNP genotype. According to an embodiment of this invention, method uses at least the two reference values for the homozygote composed of the SNP allele having a relatively high detection temperature and the heterozygote for determining a SNP genotype.

According to an embodiment, the method uses a reference value, for determining the SNP genotyping, obtained by (i) incubating a homozygote composed of the SNP allele having the relatively high detection temperature with a signal-generating means for detection of the SNP allele having the relatively high detection temperature in a reaction vessel other than the reaction vessel in the step (a), (ii) detecting signals at both the relatively high detection temperature and the relatively low detection temperature, and (iii) then obtaining a difference between the signal detected at the relatively high detection temperature and the signal detected at the relatively low detection temperature.

According to an embodiment, the method uses a reference value, for determining the SNP genotyping, obtained by (i) incubating a heterozygote composed of both of the SNP allele having the relatively high detection temperature and the SNP allele having the relatively low detection temperature with the corresponding signal-generating means in a reaction vessel other than the reaction vessel in the step (a), (ii) detecting signals at both the relatively high detection temperature and the relatively low detection temperature, and (iii) then obtaining a difference between the signal detected at the relatively high detection temperature and the signal detected at the relatively low detection temperature.

According to an embodiment, the method uses a reference value, for determining the SNP genotyping, obtained by (i) incubating a homozygote composed of the SNP allele having the relatively low detection temperature with a signal-generating means for detection of the SNP allele having the relatively low detection temperature in a reaction vessel other than the reaction vessel in the step (a), (ii) detecting signals at both the relatively high detection temperature and the relatively low detection temperature, and (iii) then obtaining a difference between the signal detected at the relatively high detection temperature and the signal detected at the relatively low detection temperature.

According to an embodiment, for SNP genotyping a sample, a difference between the signal detected at the relatively high detection temperature and the signal detected at the relatively low detection temperature is calculated and compared to the reference values of each SNP genotype.

According to an embodiment, a reference value may be obtained by calculating the ratio between the signals detected at the relatively high detection temperature and the signal detected at the relatively low detection temperature.

According to an embodiment of this invention, the reference value may be obtained under reaction conditions sufficient to provide a saturated signal at the reaction completion. For example, in order to obtain a reference value for a heterozygote composed of both of the SNP allele having the relatively high detection temperature and the SNP allele having the relatively low detection temperature, the reaction conditions such as the content of each SNP allele are selected such that a saturated signal for each SNP allele is provided at the reaction completion. According to an embodiment of this invention, the difference between the signals obtained in calculating the reference value has a certain range and the reference value is selected within the certain range or with referring to the certain range.

Where a detection temperature for the wild type allele is the relatively high detection temperature, a detection temperature for the mutant allele is the relatively low detection temperature, and the ratio between signals detected at the relatively high detection temperature and the relatively low detection temperature is calculated to obtain a difference, the wild homozygote sample show a ratio within a certain range and the heterozygote sample shows a ratio within another certain range.

For example, the wild homozygote sample shows a ratio of around for 1.0 and the heterozygote sample for SNP shows a ratio of around 2.0.

Where the sample is mutant homozygous, a background signal detected at the relatively high detection temperature may be used for the calculation of the ratio between the signal detected at the relatively high detection temperature and the signal detected at the relatively low detection temperature. In such case, ratio calculated may show a value much higher than 2.0, which indicates that the SNP genotype of the sample is mutant homozygous. Alternatively, the calculated ratio may show a value belong to the certain range of ratio (e.g. around 9.0) shown by the mutant homozygote sample.

Furthermore, even when the false signal at the relatively high detection temperature is generated for the mutant homozygote sample, the ratio will show a value much higher than 2.0, which indicates that the SNP genotype of the sample is mutant homozygous.

Therefore, the present invention for SNP genotype enables to determine the SNP genotype by using only the difference between the signal detected at the relatively high detection temperature and the signal detected at the relatively low detection temperature.

According to an embodiment, the difference provides a qualifying value obtained by mathematically processing the signal detected at the relatively high detection temperature and the signal detected at the relatively low detection temperature.

According to an embodiment, a reference value is obtained with a standard sample containing a wild homozygote, a mutant homozygote or heterozygote and used for analyzing the difference obtained from test samples.

III. Detection of at Least Three Target Nucleic Acid Sequences in a Sample Using Different Detection Temperatures In still another aspect of this invention, there is provided a method for detecting at least three target nucleic acid sequences in a sample using different detection temperatures, comprising:

(a) incubating the sample with at least three signal-generating means for detection of the at least three target nucleic acid sequences in a single reaction vessel and detecting a generated signal by using a single type of detector; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein signals to be generated by the signal-generating means are not differentiated by the single type of detector; wherein the detection is performed at each of the different detection temperatures; and (b) determining the presence of the at least three target nucleic acid sequences by the signals detected in the step (a); wherein when the presence of a target nucleic acid sequence having a certain detection temperature among the at least three target nucleic acid sequences is determined, the presence of the target nucleic acid sequence having the certain detection temperature is determined by a difference between the signal detected at one or more detection temperatures higher than the certain detection temperature and the signal detected at the certain detection temperature; wherein when the certain detection temperature is a relatively highest detection temperature among the detection temperatures, the presence of a target nucleic acid sequence is determined by the signal detected at the certain detection temperature.

Since the present invention follows in principle the first aspect of this invention described above, the common descriptions between them are omitted in order to avoid undue redundancy leading to the complexity of this specification.

Step (a): Incubation with Signal-Generating Means and Signal Detection

Firstly, the sample to be analyzed is incubated with at least three signal-generating means for detection of the at least three target nucleic acid sequences in a single reaction vessel and then a generated signal is detected by using a single type of detector. Signals to be generated by the at least three signal-generating means are not differentiated by the single type of detector.

The number of the target nucleic acid sequences to be detected by the present invention is not limited, including more than 3, 4, 5, 6, 7, 8, 9 and 10 target nucleic acid sequences in the single reaction vessel.

Each of the at least three target nucleic acid sequences is detected by a corresponding signal-generating means. Each of the at least three target nucleic acid sequences has a different detection temperature determined by the corresponding signal-generating means.

According to an embodiment, the detection temperatures assigned to target nucleic acid sequences are different by at least 2° C., 3° C., 4° C., 5° C., 7° C., 8° C., 9° C., 10° C., 11° C., 12° C., 15° C. or 20° C. from one another.

One of the target nucleic acid sequences has a relatively highest detection temperature. A signal-generating means capable of providing a signal at a relatively highest detection temperature is used to detect the target nucleic acid sequence having a relatively highest detection temperature.

A detection temperature is a temperature capable of generating not only a signal for a target nucleic acid sequence having the detection temperature but also a signal for a target nucleic acid sequence having a higher detection temperature than the detection temperature. The detection is performed at each of the different detection temperatures.

According to an embodiment, the step (a) is performed in a signal amplification process concomitantly with a nucleic acid amplification.

According to an embodiment, the step (a) is performed in a signal amplification process without a nucleic acid amplification.

According to an embodiment, at least one of the signal-generating means is a signal-generating means to generate a signal in a dependent manner on the formation of a duplex.

According to an embodiment, the signal-generating means for each of the target nucleic acid sequences are signal-generating means to generate a signal by formation of a duplex.

According to an embodiment, the signal is generated by the formation of a duplex between a target nucleic acid sequence and a detection oligonucleotide specifically hybridized with the target nucleic acid sequence. According to an embodiment, the signal is generated by a duplex formed in a dependent manner on cleavage of a mediation oligonucleotide specifically hybridized with the target nucleic acid sequence.

According to an embodiment of this invention, the signal-generating means for each of the target nucleic acid sequences are signal-generating means by formation of a duplex in a dependent manner on cleavage of a mediation oligonucleotide specifically hybridized with the target nucleic acid sequence.

According to an embodiment, at least one of the signal-generating means is a signal-generating means to generate a signal in a dependent manner on cleavage of a detection oligonucleotide.

According to an embodiment, the signal is generated by hybridization of the detection oligonucleotide with a target nucleic acid sequence and then cleavage of the detection oligonucleotide. According to an embodiment, the signal is generated by cleavage of the detection oligonucleotide in a dependent manner on cleavage of a mediation oligonucleotide specifically hybridized with the target nucleic acid sequence.

According to an embodiment, the signal generation being dependent manner on cleavage of the detection oligonucleotide is used for the target nucleic acid sequence having the relatively highest detection temperature among the at least three target nucleic acid sequences.

According to an embodiment of this invention, the signal-generating means for the target nucleic acid sequence having the relatively highest detection temperature is a signal-generating means by cleavage of a detection oligonucleotide, and the signal-generating means for the other target nucleic acid sequences are a signal-generating means by the formation of a duplex.

According to an embodiment of this invention, the signal-generating means for the target nucleic acid sequence having the relatively highest detection temperature is a signal-generating means by cleavage of a detection oligonucleotide, and the signal-generating means for the other target nucleic acid sequences are a signal-generating means by formation of a duplex in a dependent manner on cleavage of a mediation oligonucleotide specifically hybridized with the target nucleic acid sequence.

According to an embodiment of this invention, the cleavage of a mediation oligonucleotide releases a fragment and the fragment mediates a formation of a duplex or a cleavage of a detection oligonucleotide by an extension of the fragment on a capture oligonucleotide.

According to an embodiment of this invention, the at least three signal-generating means comprise an identical label and signals from the label are not differentiated by the single type of detector.

According to an embodiment of this invention, when the signal-generating means generates a signal in a dependent manner on the formation of a duplex, the detection temperature is selected based on a $T_m$ value of the duplex.

According to an embodiment of this invention, when the signal-generating means generates a signal in a dependent manner on cleavage of a detection oligonucleotide, the detection temperature is arbitrarily selected. According to an embodiment of this invention, the signal-generating means by cleavage of a detection oligonucleotide can provide a relatively highest detection temperature.

According to an embodiment, the detection temperatures for target nucleic acid sequences are predetermined in considering a temperature range to allow signal generation by the signal-generating means.

According to an embodiment, the detection temperature for each target nucleic acid sequence is predetermined in considering a temperature range to allow signal generation by the signal-generating means for detection of each target nucleic acid sequence. The detection temperatures may be predetermined in considering non-overlapped detection temperature range and overlapped detection temperature range among the detection temperatures.

The detection at a certain detection temperature is to detect a signal for a target nucleic acid sequence having the detection temperature but also a signal for a target nucleic acid sequence having a higher detection temperature than the detection temperature. The detection at a relatively highest detection temperature is to detect a signal for a target nucleic acid sequence having the relatively highest detection temperature.

For example, where the target nucleic acid sequences comprise three target sequences and detection temperatures 72° C., 60° C. and 50° C. are assigned to the three target sequences, respectively, the detection at 50° C. includes not only detection of the signal for a target nucleic acid sequence having 50° C. detection temperature but also detection of signals for target nucleic acid sequences having 70° C. and 60° C. detection temperature, respectively.

One of features of the present invention is to determine differentially the presence of the at least three target nucleic acid sequences by detecting at different detection temperatures signals indicative of the presence of the at least three target nucleic acid sequences.

Step (b): Determining the Presence of the at Least Three Target Nucleic Acid Sequences Following the detection of the signal, the presence of the at least three target nucleic acid sequences are determined by the signal detected in the step (a).

According to an embodiment, the presence of the target nucleic acid sequence having a certain detection temperature is determined in such a manner that the signal detected at the certain detection temperature is analyzed by using the signal detected at the detection temperatures higher than the certain detection temperature in order to verify whether the signal detected at the certain detection temperature contains a signal provided by the target nucleic acid sequence having the certain detection temperature or not.

When the presence of a target nucleic acid sequence having a certain detection temperature among the at least three target nucleic acid sequences is to be determined, the presence of the target nucleic acid sequence having the certain detection temperature is determined by a difference between the signal detected at one or more detection temperatures higher than the certain detection temperature and the signal detected at the certain detection temperature. Where the certain detection temperature is a relatively highest detection temperature among the detection temperatures, the presence of a target nucleic acid sequence is determined by the signal detected at the certain detection temperature.

According to an embodiment, the difference comprises a difference to be obtained by mathematically processing the signal detected at one or more detection temperatures higher than the certain detection temperature and a signal detected at the certain detection temperature.

According to an embodiment, when the signal is not detected at the detection temperatures higher than the certain detection temperature, the determination of the presence of the target nucleic acid sequence having the certain detection temperature is made by the signal detected at the certain detection temperature with considering no detection of the signal at the detection temperatures higher than the certain detection temperature. This embodiment addresses that using a difference due to the presence and absence of signals allows for the determination of the presence of the target nucleic acid sequence having the certain detection temperature.

For instance, assuming that target nucleic acid sequences comprise four target sequences, detection temperatures 72° C., 60° C., 50° C. and 40° C. are assigned to the four target sequences, respectively, and signals at detection temperatures 60° C., 50° C. and 40° C. are detected in the step (a). When the presence of a target nucleic acid sequence having 40° C. detection temperature is to be determined, the presence of the target nucleic acid sequence having the certain detection temperature (40° C.) is determined by using a difference between the signal detected at one or more detection temperatures (60° C. and 50° C.) higher than the certain detection temperature (40° C.) and the signal detected at the certain detection temperature. More clearly, a difference between the signal detected at 60° C. and the signal detected at 40° C., a difference between the signal detected at 50° C. and the signal detected at 40° C. or both of the two differences may be used for determination of the presence of a target nucleic acid sequence having 40° C. detection temperature.

The presence of target nucleic acid sequences having the other detection temperatures (i.e., 60° C. and 50° C.) can be determined respectively as disclosed above.

The term "a difference between the signal detected at one or more detection temperatures higher than the certain detection temperature and the signal detected at the certain detection temperature" includes that the difference is obtained between the signals at two detection temperatures. One of the signals is the signal detected at one of the detection temperatures higher than the certain detection temperature and the other is the signal detected at the certain detection temperature. Where the detection temperatures higher than the certain detection temperature are more than two, there may be obtained differences of more than two.

The term "a difference between the signal detected at one or more detection temperatures and the signal detected at the certain detection temperature" includes not only difference between signals detected at two detection temperatures but also difference obtained using the difference between the two detection temperatures and a signal detected at the other detection temperature.

Alternatively, according to an embodiment, the presence of the target nucleic acid sequence having the certain detection temperature (60° C.) is determined by using a difference to be obtained by mathematically processing the signal detected at one or more detection temperatures (72° C.) higher than the certain detection temperature (60° C.) and the signal detected at the certain detection temperature. As the signal is not detected at the higher detection temperature (72° C.), the background signal may be used for calculation the difference.

According to an embodiment, as the signal is not detected at the detection temperature (72° C.) higher than the certain detection temperature (60° C.), the presence of the target nucleic acid sequence having the certain detection temperature (60° C.) is determined by using the signal detected at the certain detection temperature (60° C.) with considering no detection of the signal at the detection temperature (72° C.) higher than the certain detection temperature (60° C.).

If a signal is detected at the highest detection temperature (72° C.), it can be determined that the target nucleic acid sequence having the relatively highest detection temperature is present.

According to an embodiment, when the presence of a target nucleic acid sequence having a certain detection temperature among the at least three target nucleic acid sequences is to be determined, the presence of the target nucleic acid sequence having the certain detection temperature is determined by using a difference between the signal detected at a detection temperature immediately higher than the certain detection temperature and the signal detected at the certain detection temperature.

According to an embodiment, using the difference comprises using a difference to be obtained by mathematically processing the signal detected at a detection temperature immediately higher than the certain detection temperature and a signal detected at the certain detection temperature.

According to an embodiment, when the signal is not detected at the detection temperature immediately higher than the certain detection temperature, using the difference comprises using the signal detected at the certain detection temperature with considering no detection of the signal at the detection temperature immediately higher than the certain detection temperature.

For example, when the presence of a target nucleic acid sequence having 40° C. detection temperature is to be determined, the presence of the target nucleic acid sequence having the certain detection temperature is determined by using a difference between the signal detected at the detection temperature (50° C.) immediately higher than the certain detection temperature (40° C.) and the signal detected at the certain detection temperature.

According to an embodiment, a reference value is required to determine whether signals detected at the 50° C. and 40° C. detection temperatures are indicative of the presence of target nucleic acid sequences having the 50° C. and 40° C. detection temperatures.

According to an embodiment of this invention, depending on approaches for obtaining the difference, a threshold may be employed to analyze whether the difference obtained is indicative of the presence of the target nucleic acid sequence having the certain detection temperature.

According to an embodiment of this invention, depending on approaches for obtaining the difference, the presence of the target nucleic acid sequence having the certain detection temperature may be determined by using the difference obtained per se. For example, a threshold value is pre-reflected in obtaining the difference for embodying such direct utilization of the difference per se.

According to an embodiment of this invention, a reference value is used for determining the presence of target nucleic acid sequences.

In certain embodiment, difference in signals at the certain detection temperature and the detection temperature higher than the certain detection temperature provided by the target nucleic acid sequence having the detection temperature higher than the certain detection temperature may be expressed through a reference value.

In certain embodiment, the reference value for the case in which the signals at the certain detection temperature and the detection temperature higher than the certain detection temperature provided by the target nucleic acid sequence having the detection temperature higher than the certain detection temperature are different from each other may be different by more than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 12%, 15%, 20% or 30%, compared with the reference value for the case in which the two signals are the same.

In certain embodiment, the reference value for the target nucleic acid sequence having the detection temperature higher than the certain detection temperature may be used in determination of the presence of the target nucleic acid sequence having the certain low detection temperature, where the reference value for the target nucleic acid sequence having the detection temperature higher than the certain detection temperature calculated from the signals at two detection temperatures may be different by more than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 12%, 15%, 20% or 30% compared with the reference value for the case in which the two signals are the same.

According to an embodiment, where the comparison is performed to determine whether a reference value is used, the reference value is calculated by division of the signals. According to an embodiment, the method of calculating the reference value for determining whether the reference value is used may be the same or different from each other the method of calculating the reference value for detecting the target nucleic acid sequence.

According to an embodiment, where signals for a plurality of target nucleic acid sequences are detected at the detection temperature higher than the certain detection temperature, a reference value for a plurality of target nucleic acid sequences is used in considering a pattern of signal change at changed detection temperatures for a plurality of target nucleic acid sequences.

According to an embodiment, where the target nucleic acid sequence having the detection temperature higher than the certain detection temperature is present, the reference value is used to determine the presence of the target nucleic acid sequence having the certain detection temperature.

The case in which the target nucleic acid sequence having the detection temperature higher than the certain detection temperature is present includes a case in which a significant signal indicative of the presence of the target nucleic acid sequence having the detection temperature higher than the certain detection temperature is detected at the detection temperature higher than the certain detection temperature.

According to an embodiment, where the target nucleic acid sequence having the detection temperature higher than the certain detection temperature is absent, the reference value is optionally used to determine the presence of the target nucleic acid sequence having the certain detection temperature.

The case in which the target nucleic acid sequence having the detection temperature higher than the certain detection temperature is absent includes a case in which a signal with similar intensity to a background signal is only detected.

The references values may be pre-prepared for all combinations or for some selected combinations of the target nucleic acid sequences. According to an embodiment of this invention, the references value is a difference between signals at detection temperatures obtained from the above combinations.

According to an embodiment of this invention, the reference value may be obtained under reaction conditions sufficient to provide a saturated signal at the reaction completion. For example, in order to obtain a reference value for a combination of two target nucleic acid sequences, the reaction conditions such as the content of each target nucleic acid sequence are selected such that a saturated signal for each target nucleic acid sequence is provided at the reaction completion.

According to an embodiment of this invention, the difference between the signals obtained in calculating the reference value has a certain range and the reference value is selected within the certain range or with referring to the certain range.

The reference values may be used to determine a significance of the difference obtained in the sample, in considering method for obtaining difference and practical detection results. The reference values may be used to obtain the difference in the sample, whereby involved in the determination of the presence of target nucleic acid.

According to an embodiment of this invention, for determining the presence of the target nucleic acid sequence having the certain detection temperature, the method uses at least one reference value among the reference values obtained by (i) incubating all combinations of target nucleic acid sequences having detection temperatures higher than the certain detection temperature with corresponding signal-generating means in a reaction vessel other than the reaction vessel in the step (a), (ii) detecting signals at not only one or more detection temperatures higher than the certain detection temperature but also the certain detection temperature, and (iii) then obtain a difference between the signal detected at the one or more detection temperatures higher than the certain detection temperature and the signal detected at the certain detection temperature.

Where at least three target nucleic acid sequences are intended to detect by the present invention, various reference values may be obtained in considering various combinations of target nucleic acid sequences with various combination of the two detection temperatures selected for signal detection.

According to an embodiment of this invention, the presence of target nucleic acid sequences is determined in order of their detection temperatures from the target nucleic acid sequence having the highest detection temperature to the target nucleic acid sequence having the lowest detection temperature, and reference values are suitably selected depending on methods for determination of target presence and used.

In the above example, for obtaining a reference value for determining the presence of the target nucleic acid sequence having the certain detection temperature (40° C.), all combinations (i.e., target nucleic acid sequence having the 60° C. detection temperature, target nucleic acid sequence having the 50° C. detection temperature, and a combination of target nucleic acid sequences having the 60° C. and 50° C. detection temperatures) of target nucleic acid sequences having detection temperatures (60° C. and 50° C.) higher than the certain detection temperature (40° C.) are incubated with signal-generating means to generate signals; signals are detected at not only one or more detection temperatures (60° C. and 50° C.) higher than the certain detection temperature (40° C.) but also the certain detection temperature (40° C.); and then the signal detected at the one or more detection temperatures higher than the certain detection temperature and the signal detected at the certain detection temperature are used to obtain the difference between the signals. In accordance with the same method, reference values for determining the presence of target nucleic acid sequence having the other detection temperatures (i.e., 60° C. and 50° C.) are obtained.

Alternatively, for determining the presence of the target nucleic acid sequence having the certain detection temperature, the method further uses at least one reference value among the reference values obtained by (i) incubating all combinations of target nucleic acid sequences having detection temperatures higher than the certain detection temperature with corresponding signal-generating means in a reaction vessel other than the reaction vessel in the step (a), (ii) detecting signals at both a detection temperature immediately higher than the certain detection temperature and the certain detection temperature, and (iii) then obtaining a difference between the signal detected at the detection temperature immediately higher than the certain detection temperature and the signal detected at the certain detection temperature to obtain the difference between the signals.

In the above example, for obtaining a reference value for determining the presence of the target nucleic acid sequence having the certain detection temperature (40° C.), all combinations (i.e., target nucleic acid sequence having the 60° C. detection temperature, target nucleic acid sequence having the 50° C. detection temperature, and a combination of target nucleic acid sequences having the 60° C. and 50° C. detection temperatures) of target nucleic acid sequences having detection temperatures (60° C. and 50° C.) higher than the certain detection temperature (40° C.) are incubated with signal-generating means to generate signals; signals are detected at both a detection temperature (50° C.) immediately higher than the certain detection temperature (40° C.) and the certain detection temperature (40° C.); then the signal detected at a detection temperature (50° C.) immediately higher than the certain detection temperature and the signal detected at the certain detection temperature (40° C.) are used to obtain the difference between the signals. In accordance with the same method, reference values for determining the presence of target nucleic acid sequence having the other detection temperatures (i.e., 60° C. and 50° C.) are obtained.

According to an embodiment of this invention, the reference value is obtained be obtained by calculating the ratio or subtraction between the signals detected at one of the detection temperatures higher than the certain detection temperature and the certain detection temperature. According to an embodiment of this invention, the reference value is obtained by calculating the ratio of the signal detected at the certain detection temperature to the signal detected at one of the detection temperatures higher than the certain detection temperature. According to an embodiment of this invention, the reference value is obtained by calculating the ratio of the signal detected at one of the detection temperatures higher than the certain detection temperature to the signal detected at the certain detection temperature.

According to an embodiment, where the threshold is obtained using the reference value for determining the presence of the target nucleic acid sequence having the certain detection temperature, it may be obtained using a certain reference value or some reference values among reference values obtained from various combinations of target nucleic acid sequences. For instance, where one among the target nucleic acid sequence having a detection temperature higher than the certain detection temperature is analyzed to not exist, reference values obtained from a combination of target nucleic acid sequences containing not the one target nucleic acid sequence is employed to determine the threshold.

In an embodiment, where at least three target nucleic acid sequences are detected, for verifying the presence of the target nucleic acid sequence having the certain detection temperature, a standard sample comprising combinations of target nucleic acid sequences except for the target nucleic acid sequence having the certain detection temperature is pre-prepared and then reference values are obtained. In considering the reference values, a threshold is obtained for determining the presence of the target nucleic acid sequence having the certain detection temperature.

According to an embodiment, using the signal detected at the certain detection temperature comprises obtaining a qualifying value for determining the presence of the target nucleic acid sequence having the relatively highest detection temperature and using the difference comprises obtaining a qualifying value for determining the presence of the target nucleic acid sequence having the certain detection temperature.

According to an embodiment of this invention, using the difference comprises obtaining a qualifying value for determining the presence of the target nucleic acid sequence having the certain detection temperature, and the qualifying value is obtained by (i) mathematically processing the signal detected at one or more detection temperatures higher than the certain detection temperature and the signal detected at the certain detection temperature or (ii) using the signal detected at the certain detection temperature with considering no detection of the signal at the one or more detection temperature higher than the certain detection temperature when the signal is not detected at the one or more detection temperature higher than the certain detection temperature.

According to an embodiment of this invention, the step (b) is performed by determining firstly the presence of a target nucleic acid sequence having a relatively highest detection temperature and then sequentially determining the presence of target nucleic acid sequences having relatively lower detection temperatures in a descending order.

According to an embodiment, the single reaction vessel further comprises at least one additional set each of which contains additional at least three signal-generating means for detection of target nucleic acid sequences other than the at least three target nucleic acid sequences; wherein the signals generated by each set of at least three signal-generating means in the vessel are differentiated from each other and the signals are detected by different types of detectors, respectively.

According to an embodiment of this invention, the target nucleic acid sequences comprise a nucleotide variation (particularly SNP).

IV. Detection of Two Target Nucleic Acid Sequences Using Different Detection Temperatures and Melting Analysis In a further aspect of this invention, there is provided a method for detecting two target nucleic acid sequences in a sample using different detection temperatures and melting analysis, comprising:

(a) incubating the sample with two signal-generating means for detection of the two target nucleic acid sequences in a single reaction vessel and detecting a generated signal by using a single type of detector; wherein each of the target nucleic acid sequences is detected by a corresponding signal-generating means; wherein one of the two target nucleic acid sequences has a relatively high detection temperature and the other has a relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; wherein signals to be generated by the two signal-generating means are not differentiated by a single type of detector; wherein the detection is performed at the relatively high detection temperature;

(b) performing a melting analysis of the incubation resultant of the step (a) over a range of temperatures for determining the presence of the target nucleic acid sequence having the relatively low detection temperature; and (c) determining the presence of the target nucleic acid sequence having the relatively high detection temperature by the signal detected in the step (a) and the presence of the target nucleic acid sequence having the relatively low detection temperature by using the result of the melting analysis in the step (b).

Step (a): Incubation with Signal Generating Means and Signal Detection

Firstly, the sample to be analyzed is incubated with two signal-generating means for detection of the two target nucleic acid sequences in a single reaction vessel and then a generated signal is detected by using a single type of detector. Signals to be generated by the two signal-generating means are not differentiated by the single type of detector.

Each of the target nucleic acid sequences is detected by a corresponding signal generating means. One of the two target nucleic acid sequences has a relatively high detection temperature and the other has a relatively low detection temperature determined by the corresponding signal-generating means.

According to an embodiment of the present invention, the target nucleic acid sequence having a relatively high detection temperature is detected by a real-time detection method using a different detection temperature, and the target nucleic acid sequence having a relatively low detection temperature is detected by melting analysis.

The detection in the step (a) is performed at the relatively high detection temperature and not at the relatively low detection temperature.

The signal generating means capable of generating a signal during melting analysis is chosen for the target nucleic acid sequence having the relatively low detection temperature.

According to an embodiment, because the signal-generating means for the melting analysis employs hybridization and denaturation of a duplex, it may generate a signal depending on reaction conditions in the step (a).

According to an embodiment, the signal-generating means for generating a signal for the target nucleic acid sequence having the relatively low detection temperature has to be constructed to generate no signal at the relatively high detection temperature.

In the fourth aspect of this invention, the signal generating means for generating a signal for the target nucleic acid sequence having the relatively low detection temperature may generate or not generate signal depending on reaction conditions in the step (a). Even if a signal for the target nucleic acid sequence having the relatively low detection temperature may generate in a certain reaction condition, the generated signal is not detected as a signal detection is performed at the relatively high detection temperature in the step (a).

Since the signal for the target nucleic acid sequence having the relatively low detection temperature may be generated and detected in the step (b), the signal is not compelled to be generated in the step (a).

According to an embodiment, the signal-generating means for the melting analysis does not include a means generating signal by cleavage of labeled probes or labeled duplex. As the melting analysis employs $T_m$ value of hybrids, the cleavage of hybrids to be detected has to be excluded. Upon cleavage, melting peaks may be not produced or detection sensitivity may be greatly reduced. In addition, signal by cleavage is likely to be a false positive signal in the real-time detection method.

The step (a) is performed under conditions capable of generating at least the signal for the target nucleic acid sequence having the relatively high detection temperature.

According to an embodiment, the step (a) is performed in a signal amplification process concomitantly with a nucleic acid amplification.

According to an embodiment, the step (a) is performed in a signal amplification process without a nucleic acid amplification.

According to an embodiment, at least one of the signal-generating means is a signal-generating means to generate a signal in a dependent manner on the formation of a duplex.

According to an embodiment, the signal-generating means for each of the target nucleic acid sequences are a signal-generating means to generate a signal in a dependent manner on the formation of a duplex.

According to an embodiment, the signal is generated by the formation of a duplex between a target nucleic acid sequence and a detection oligonucleotide specifically hybridized with the target nucleic acid sequence. According to an embodiment, the signal is generated by a duplex formed in a dependent manner on cleavage of a mediation oligonucleotide specifically hybridized with the target nucleic acid sequence.

According to an embodiment, at least one of the signal-generating means is a signal-generating means to generate a signal in a dependent manner on cleavage of a detection oligonucleotide. According to an embodiment, the signal is generated by hybridization of the detection oligonucleotide with a target nucleic acid sequence and then cleavage of the detection oligonucleotide. According to an embodiment, the signal is generated by cleavage of the detection oligonucleotide in a dependent manner on cleavage of a mediation oligonucleotide specifically hybridized with the target nucleic acid sequence.

According to an embodiment, the signal-generating means for each of the target nucleic acid sequences are a signal-generating means by formation of a duplex in a dependent manner on cleavage of a mediation oligonucleotide specifically hybridized with the target nucleic acid sequence According to an embodiment, the signal generation being dependent manner on cleavage of the detection oligonucleotide is used for the target nucleic acid sequence having the relatively high detection temperature.

Particularly, it is very advantageous to use the signal generation being dependent manner on cleavage of the detection oligonucleotide for the target nucleic acid sequence having the relatively high detection temperature for the following reasons: (i) a detection temperature may be selected with a relatively wide temperature range; (ii) a much higher temperature compared with hybridization approaches may be selected; and (iii) it is possible to provide no signal in melting analysis by selecting suitable signal-generating means and reaction conditions (e.g., selection of signal-generating means incapable of providing signals by only hybridization without cleavage or selection of conditions allowing for cleavage of most of detection oligonucleotides).

The signal-generating means to generate a signal in a dependent manner on the formation of a duplex (e.g., Molecular beacon) may also provide signal through cleavage by 5'-nuclease being dependent on reaction conditions. The signal-generating means may be considered as that capable of providing signal by cleavage, so long as it is used to generate signal by cleavage.

According to an embodiment, the signal-generating means for the target nucleic acid sequence having the relatively high detection temperature is a signal-generating means by cleavage of a detection oligonucleotide, and the signal-generating means for the target nucleic acid sequence having the relatively low detection temperature is a signal-generating means by the formation of a duplex.

According to an embodiment, the signal-generating means for the target nucleic acid sequence having the relatively high detection temperature is a signal-generating means by cleavage of a detection oligonucleotide, and the signal-generating means for the target nucleic acid sequence having the relatively low detection temperature generates a signal by a duplex formed in a dependent manner on cleavage of a mediation oligonucleotide specifically hybridized with the target nucleic acid sequence.

According to an embodiment, the two signal-generating means comprises an identical label and signals from the label are not differentiated by the single type of detector.

After the incubation (reaction) of the sample with two signal-generating means to generate signal, the generated signal is detected by using a single type of detector. The detection is performed at the relatively high detection temperature capable of generating a signal for the target nucleic acid sequence having the relatively high detection temperature.

Step (b): Melting Analysis

Afterwards, the melting analysis of the incubation resultant of the step (a) is performed over a range of temperatures for determining the presence of the target nucleic acid sequence having the relatively low detection temperature.

The present specification describes performing the step (b) after the detection in the step (a) only for convenience in description. Given the principle underlying the present invention, it would be understood that the step (b) may be performed before the detection in the step (a). Therefore, the process comprising the step (b) before the detection in the step (a) is also encompassed by the scope of the present invention.

The step (b) may be carried out by various melting analysis processes known to one of skill in the art. The term "melting analysis" used herein is intended to encompass not only a melting analysis in a narrow sense but also a hybridization analysis, unless otherwise indicated. The melting analysis in a narrow sense refers to a method in which the dissociation of duplexes is measured under increasing stringency conditions by adjusting temperatures. The hybridization analysis in a narrow sense refers to a method in which the association of duplexes is measured under decreasing stringency conditions by adjusting temperatures. The term "melting curve" or "melting peak curve" used herein is intended to encompass not only a melting curve or melting peak curve from a melting analysis in a narrow sense but also a hybridization curve or hybridization peak curve from a hybridization analysis, unless otherwise indicated. The melting curve or hybridization curve may be obtained by conventional technologies, for example, as described in U.S. Pat. Nos. 6,174,670 and 5,789,167, Drobyshev et al, *Gene* 188: 45(1997); *Kochinsky and Mirzabekov Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

The melting (hybridization) curve analysis and the melting (hybridization) peak analysis will be described with reference to disclosures of U.S. Pat. No. 8,039,215.

The melting analysis uses "$T_m$" values. The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research*, 6:3543-3547(1979)) and nearest-neighbor method (SantaLucia J. Jr., et al., *Biochemistry*, 35:3555-3562(1996)); Sugimoto N., et al., *Nucleic Acids Res.*, 24:4501-4505(1996)).

According to an embodiment, the step (b) is performed by detecting signals generated with increasing temperatures (melting analysis in a narrow sense). Alternatively, the step (b) is performed by detecting signals generated with decreasing temperatures (hybridization analysis in a narrow sense).

According to an embodiment, the signal-generating means used for the melting analysis includes any means generating signal from a duplex formation over a range of temperatures. Among signal-generating means for real-time detection methods, means generating signal by hybridization of a detection oligonucleotide rather than cleavage reaction is also used for the melting analysis.

According to an embodiment, the step (b) is performed by using a signal-generating means to generate a signal in a dependent manner on the formation of a duplex. Particularly, the step (b) is performed by using a signal generating means generated signal by a duplex formed in a dependent manner on cleavage of a mediation oligonucleotide specifically hybridized with the target nucleic acid sequence.

The signal by the duplex formed in a dependent manner on cleavage of the mediation oligonucleotide may be generated by various methods, including PTOCE-melting method (WO 2012/096523), PCE-SH-melting method (WO 2013/115442) and PCE-NH-melting method (PCT/KR2013/012312). The PTOCE-melting method, PCE-SH-melting method and PCE-NH-melting method correspond to a PTOCE-based method with melting analysis, a PCE-SH-melting method with melting analysis and a PCE-NH-melting method with melting analysis, respectively. Among the PTOCE-based methods, methods to generate no signal by cleavage are employed for the melting analysis in the step (b).

The PTOCE-melting method, PCE-SH-melting method and PCE-NH-melting method are also described in the prior patent documents.

The steps (a)-(b) performed by the PTOCE-melting method comprise the following steps:
(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; (e) melting the extended duplex over a range of temperatures to give a target signal indicative of the presence of the extended duplex; wherein the target signal is provided by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (f) detecting the extended duplex by measuring the target signal; whereby the presence of the extended duplex indicates the presence of the target nucleic acid sequence.

In this case, the PTOCE melting method further comprises repeating the steps all or some of the steps (a)-(f) with denaturation between repeating cycles. In the step (a) of PTOCE-melting method, a primer set for amplification of the target nucleic acid sequence may be used instead of the upstream oligonucleotide. In this case, the method further comprises repeating the steps all or some of the steps (a)-(f) with denaturation between repeating cycles.

The steps (a)-(b) of the present invention performed by the PTOCE-based melting methods comprise the following steps:

(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended to form an extended strand; and (e) performing a melting analysis over a range of temperatures by detecting signal generated dependent on the presence of the extended strand.

Step (c): Determining the Presence of Target Nucleic Acid Sequences

Finally, the presence of the target nucleic acid sequence having the relatively high detection temperature is determined by using the signal detected in the step (a) and the presence of the target nucleic acid sequence having the relatively low detection temperature is determined by using the result of the melting analysis in the step (b).

According to an embodiment of this invention, the target nucleic acid sequences comprise a nucleotide variation (particularly SNP).

The unexpected results of the present invention may be yielded when a signal-generating means to generate signal by cleavage for a real-time detection is combined with a signal-generating means to generate signal by a duplex formed in a dependent manner on cleavage of a mediation oligonucleotide hybridized with the target nucleic acid sequence for the melting analysis. In such case, a signal-generating means involving the formation of duplex and generating signal directly by cleavage should be excluded for the melting analysis.

It is noteworthy that the present invention is performed in a combination of the signal-generating means to generate signal by cleavage (e.g. the TaqMan method) as a real-time process and the PTOCE-based melting method as a melting analysis, providing the most striking results.

According to an embodiment, using the signal detected in the step (a) comprises obtaining a qualifying value for determining the presence of the target nucleic acid sequence having the relatively high detection temperature.

According to an embodiment of this invention, the target nucleic acid sequences comprise a nucleotide variation (particularly SNP).

V. Detection of at Least Three Target Nucleic Acid Sequences Using Different Detection Temperatures and Melting Analysis In still further aspect of this invention, there is provided a method for detecting at least three target nucleic acid sequences in a sample using detection temperature analysis and melting analysis, comprising:

(a) incubating the sample with at least three signal-generating means for detection of the at least three target nucleic acid sequences in a single reaction vessel and detecting a generated signal by using a single type of detector; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein signals to be generated by the signal-generating means are not differentiated by the single type of detector; wherein some of the at least three target nucleic acid sequences are detected by detection temperature analysis and the detection is performed at both the detection temperature of said some of the at least three target nucleic acid sequences and one or more detection temperatures higher than the detection temperatures;

(b) performing a melting analysis of the incubation resultant of the step (a) over a range of temperatures for determining the presence of the other target nucleic acid sequences than said some of the at least three the target nucleic acid sequences; and (c) determining (i) the presence of said some of the target nucleic acid sequences by the signal detected in the step (a); wherein when the presence of a target nucleic acid sequence having a certain detection temperature among said some of the at least three target nucleic acid sequences is determined, the presence of the target nucleic acid sequence having the certain detection temperature is determined by a difference between the signal detected at one or more detection temperatures higher than the certain detection temperature and the signal detected at the certain detection temperature; wherein when the certain detection temperature is a relatively highest detection temperature among the detection temperatures, the presence of the target nucleic acid sequence is determined by the signal detected at the certain detection temperature; and (ii) the presence of the other target nucleic acid sequences than said some of the at least three target nucleic acid sequences is determined by the result of the melting analysis in the step (b).

Since the present invention follows in principle, the first aspect to the fourth aspect of this invention described above, the common descriptions between them are omitted in order to avoid undue redundancy leading to the complexity of this specification.

Step (a): Incubation with Signal-Generating Means and Signal Detection

Firstly, the sample to be analyzed is incubated with at least three signal-generating means for detection of the at least three target nucleic acid sequences in a single reaction vessel and then a generated signal is detected by using a single type of detector. Signals to be generated by the at least three signal generating means are not differentiated by the single type of detector.

One of the target nucleic acid sequences has a relatively highest detection temperature. A signal-generating means capable of providing a signal at a relatively highest detection temperature is used to detect the target nucleic acid sequence having a relatively highest detection temperature.

In the present invention, some of the at least three target nucleic acid sequences are detected by the detection temperature analysis and the other are detected by the melting analysis.

The tem "some" in the expression "some of the at least three target nucleic acid sequences" includes one or more. The tem used herein "detection temperature analysis" refers to a real-time detection method comprising detection at different temperatures to detect a target nucleic acid sequence, unless otherwise indicated.

The signal-generating means for generating a signal for the target nucleic acid sequence to be analyzed by the melting analysis may generate or not generate the signal depending on reaction conditions in the step (a). Since the signal for the target nucleic acid sequence to be analyzed by the melting analysis may be generated and detected in the step (b), the signal is not compelled to be generated in the step (a).

Each of the at least three target nucleic acid sequences has to use a signal-generating means having a different detection temperature from one another.

According to an embodiment, because the signal-generating means for the melting analysis employs hybridization and denaturation of a duplex, it may generate a signal depending on reaction conditions in the step (a).

According to an embodiment, the step (a) is carried out under conditions suitable in generation of at least a signal for a target nucleic acid sequence to be analyzed by the detection temperature analysis.

According to an embodiment, the selection of target nucleic acid sequences to be analyzed by the detection temperature analysis is done in considering detection temperatures. Particularly, a target nucleic acid sequence having the highest detection temperature is firstly selected and then some sequences are selected in a detection temperature order.

According to an embodiment, the step (a) is performed in a signal amplification process concomitantly with a nucleic acid amplification.

According to an embodiment, the step (a) is performed in a signal amplification process without a nucleic acid amplification.

According to an embodiment, at least one of the signal-generating means is a signal-generating means to generate a signal in a dependent manner on the formation of a duplex.

According to an embodiment, the signal-generating means for each of the target nucleic acid sequences are signal-generating means to generate a signal by formation of a duplex.

According to an embodiment, the signal is generated by the formation of a duplex between a target nucleic acid sequence and a detection oligonucleotide specifically hybridized with the target nucleic acid sequence. According to an embodiment, the signal is generated by a duplex formed in a dependent manner on cleavage of a mediation oligonucleotide specifically hybridized with the target nucleic acid sequence.

According to an embodiment of this invention, the signal-generating means for each of the target nucleic acid sequences are signal-generating means by formation of a duplex in a dependent manner on cleavage of a mediation oligonucleotide specifically hybridized with the target nucleic acid sequence.

According to an embodiment, at least one of the signal-generating means is a signal-generating means to generate a signal in a dependent manner on cleavage of a detection oligonucleotide. According to an embodiment, the signal is generated by hybridization of the detection oligonucleotide with a target nucleic acid sequence and then cleavage of the detection oligonucleotide. According to an embodiment, the signal is generated by cleavage of the detection oligonucleotide in a dependent manner on cleavage of a mediation oligonucleotide specifically hybridized with the target nucleic acid sequence.

According to an embodiment, the signal generation being dependent manner on cleavage of the detection oligonucleotide is used only for the target nucleic acid sequence having the relatively highest detection temperature among the at least three target nucleic acid sequences.

According to an embodiment of this invention, the signal-generating means for the target nucleic acid sequence having the relatively highest detection temperature is a signal-generating means by cleavage of a detection oligonucleotide, and the signal-generating means for the other target nucleic acid sequences are a signal-generating means by the formation of a duplex.

According to an embodiment of this invention, the signal-generating means for the target nucleic acid sequence having the relatively highest detection temperature is a signal-generating means by cleavage of a detection oligonucleotide, and the signal-generating means for the other target nucleic acid sequences generate signals by the formation of a duplex in a dependent manner on cleavage of a mediation oligonucleotide specifically hybridized with the target nucleic acid sequence.

For example, the signal for the target nucleic acid sequence having the relatively highest detection temperature is generated by TaqMan method and signals for the other target nucleic acid sequences are generated by the PTOCE method, PCE-SH method or PCE-NH method.

According to an embodiment of this invention, the at least three signal-generating means comprise an identical label and signals from the label are not differentiated by the single type of detector.

The number of the target nucleic acid sequences to be detected by the present invention is not limited, including more than 3, 4, 5, 6, 7, 8, 9 and 10 target nucleic acid sequences in the single reaction vessel.

After the incubation (reaction) of the sample with the at least three signal-generating means to generate signal, the generated signal is detected by using a single type of detector. According to an embodiment, some of the at least three target nucleic acid sequences are detected by the detection temperature analysis and the detection is performed at both the detection temperatures of said some of the at least three target nucleic acid sequences and one or more detection temperatures higher than the detection temperatures.

According to an embodiment, signals are detected at all detection temperatures required for performing the detection temperature analysis.

The generated signal is detected by using a single type of detector. Each of the at least three target nucleic acid sequences has a different detection temperature determined by the corresponding signal-generating means. A detection temperature is a temperature capable of generating not only a signal for a target nucleic acid sequence having the detection temperature but also a signal for a target nucleic acid sequence having a higher detection temperature than the detection temperature.

According to an embodiment, the target nucleic acid sequences to be detected by the detection temperature analysis have detection temperatures higher than those to be detected by the melting analysis.

Step (b): Melting Analysis

The melting analysis of the incubation resultant of the step (a) is performed over a range of temperatures for determining the presence of the other target nucleic acid sequences than said some of the at least three target nucleic acid sequences.

The present specification describes performing the step (b) after the detection in the step (a) only for convenience in description. Given the principle underlying the present invention, it would be understood that the step (b) may be performed before the detection in the step (a). Therefore, the process comprising the step (b) before the detection in the step (a) is also encompassed by the scope of the present invention.

According to an embodiment, the step (b) is performed by using a signal-generating means to generate a signal in a dependent manner on the formation of a duplex. Particularly, the step (b) is performed in accordance with the PTOCE based-melting method.

Step (c): Determining the Presence of Target Nucleic Acid Sequences

Finally, the presence of the at least three target nucleic acid sequences in the sample is determined by using the signal in the step (a) and the result of the melting analysis in the step (b).

The presence of some of the target nucleic acid sequences is determined by using the signal detected in the step (a). When the presence of a target nucleic acid sequence having a certain detection temperature among said some of the at least three target nucleic acid sequences is determined, the presence of the target nucleic acid sequence having the certain detection temperature is determined by using a difference between the signal detected at one or more detection temperatures higher than the certain detection temperature and the signal detected at the certain detection temperature. When the certain detection temperature is a relatively highest detection temperature among the detection temperatures, the presence of the target nucleic acid sequence is determined by using the signal detected at the certain detection temperature;

According to an embodiment, the method further uses a reference value for determining the presence of the target nucleic acid sequence having the certain detection temperature, obtained by (i) incubating all combinations of target nucleic acid sequences having detection temperatures higher than the certain detection temperature with signal-generating means in a reaction vessel other than the reaction vessel in the step (a), (ii) detecting signals at not only one or more detection temperatures higher than the certain detection temperature but also the certain detection temperature, and (iii) then obtaining a difference between the signal detected at the one or more detection temperatures higher than the certain detection temperature and the signal detected at the certain detection temperature.

Alternatively, the method further uses a reference value for determining the presence of the target nucleic acid sequence having the certain detection temperature, obtained by (i) incubating all combinations of target nucleic acid sequences having detection temperatures higher than the certain detection temperature with signal-generating means in a reaction vessel other than the reaction vessel in the step (a), (ii) detecting signals at both the detection temperature immediately higher than the certain detection temperature and the certain detection temperature, and (iii) then obtaining a difference between the signal detected at the detection temperature immediately higher than the certain detection temperature and the signal detected at the certain detection temperature.

According to an embodiment, where signal detection at detection temperatures for target nucleic acid sequences to be detected by the melting analysis is required for obtaining the difference between signals or reference values for target nucleic acid sequences to be detected by the detection temperature analysis, signals may be collected at the detection temperatures for target nucleic acid sequences to be detected by the melting analysis and be used.

The presence of the other target nucleic acid sequences than some of the at least three target nucleic acid sequences to be determined by the detection temperature analysis is determined by the result of the melting analysis in the step (b).

According to an embodiment, the step (d) is performed by determining firstly the presence of a target nucleic acid sequence having a relatively highest detection temperature and then sequentially determining the presence of target nucleic acid sequences having relatively lower detection temperatures in a descending order.

According to an embodiment, the determination of the presence of a target nucleic acid sequence by the melting analysis may be used in determination of the presence of a target nucleic acid sequence by the detection temperature analysis (e.g., for selection of reference values).

Where the at least three target nucleic acid sequences are detected in a real-time manner, a signal generation by cleavage is used only for one target nucleic acid sequence. For the other target nucleic acid sequences, the PTOCE-based methods may be employed to improve efficiency and readiness of analysis.

According to an embodiment of this invention, the target nucleic acid sequences comprise a nucleotide variation (particularly SNP).

VI. Kits for Detection of Target Nucleic Acid Sequences by Using Multiple Detection Temperatures In another aspect of this invention, there is provided a kit for detecting two target nucleic acid sequences in a sample using different detection temperatures, comprising:
  (a) two signal-generating means for detection of the two target nucleic acid sequences; wherein each of the target nucleic acid sequences is detected by a corresponding signal-generating means; wherein one of the two target nucleic acid sequences has a relatively high detection temperature and the other has a relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; wherein signals to be generated by the two signal-generating means are not differentiated by the single type of detector; wherein the detection is performed at both the relatively high detection temperature and the relatively low detection temperature; and
  (b) an instruction that describes the present method of the Aspect I titled as Detection of Two Target Nucleic Acid Sequences in a Sample Using Different Detection Temperatures.

In still another aspect of this invention, there is provided a kit for SNP genotyping of a nucleic acid sequence in a sample using different detection temperatures, comprising:
  (a) a signal-generating means for detection of SNP alleles; wherein each of the SNP alleles is detected by a corresponding signal-generating means; wherein one of the SNP alleles has a relatively high detection temperature and the other has a relatively low detection temperature determined by the corresponding signal-generating means; wherein the relatively high detection temperature is a temperature capable of generating a signal for the SNP allele having the relatively high detection temperature and the relatively low detection temperature is a temperature capable of generating both of, a signal for the SNP allele having the relatively low detection temperature and a signal for the SNP allele having the relatively high detection temperature; wherein signals to be generated by the signal-generating means are not differentiated by the single type of detector; wherein the detection is performed at both the relatively high detection temperature and the relatively low detection temperature; and
  (b) an instruction that describes the present method of the Aspect II titled as SNP Genotyping Using Different Detection Temperatures.

In further aspect of this invention, there is provided a kit for detecting at least three target nucleic acid sequences in a sample using different detection temperatures, comprising:
  (a) at least three signal-generating means for detection of the at least three target nucleic acid sequences; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein signals to be generated by the signal-generating means are not differentiated by the single type of detector; wherein the detection is performed at each of the different detection temperatures; and
  (b) an instruction that describes the present method of the Aspect III titled as Detection of at least Three Target Nucleic Acid Sequences in a Sample Using Different Detection Temperatures.

In still further aspect of this invention, there is provided a kit for detecting two target nucleic acid sequences in a sample using different detection temperatures and melting analysis, comprising:
  (a) two signal-generating means for detection of the two target nucleic acid sequences; wherein each of the target nucleic acid sequences is detected by a corresponding signal-generating means; wherein one of the two target nucleic acid sequences has a relatively high detection temperature and the other has a relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; wherein signals to be generated by the two signal-generating means are not differentiated by a single type of detector; wherein the detection is performed at the relatively high detection temperature; wherein the signal-generating means for the target nucleic acid sequence having the relatively high detection temperature is a signal-generating means by cleavage of a detection oligonucleotide, and the signal-generating means for the target nucleic acid sequence having the relatively low detection temperature is a signal-generating means by the formation of a duplex; and
  (b) an instruction that describes the present method of the Aspect IV titled as Detection of Two Target Nucleic Acid Sequences Using Different Detection Temperatures and Melting Analysis.

In another aspect of this invention, there is provided a kit for detecting at least three target nucleic acid sequences in a sample using detection temperature analysis and melting analysis, comprising:
  (a) at least three signal-generating means for detection of the at least three target nucleic acid sequences; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein signals to be generated by the signal-generating means are not differentiated by the single type of detector; wherein some of the at least three target nucleic acid sequences are detected by detection temperature analysis and the detection is performed at both the detection temperature of said some of the at least three target nucleic acid sequences and one or more detection temperatures higher than the detection temperatures; wherein the signal-generating means for the target nucleic acid sequence having the relatively highest detection temperature is a signal-generating means by cleavage of a detection oligonucleotide, and the signal-generating means for the other target nucleic acid sequences are a signal-generating means by the formation of a duplex; and (b) an instruction that describes the present method of the Aspect V titled as Detection of at least Three Target Nucleic Acid Sequences Using Different Detection Temperatures and Melting Analysis.

Since the kits of this invention are prepared to perform the present methods, the common descriptions between them are omitted in order to avoid undue redundancy leading to the complexity of this specification.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The components of the kit may be present in separate containers, or multiple components may be present in a single container.

The instructions for describing or practicing the methods of the present invention may be recorded on a suitable recording medium. For example, the instructions may be printed on a substrate, such as paper and plastic. In other embodiments, the instructions may be present as an electronic storage data file present on a suitable computer readable storage medium such as CD-ROM and diskette. In yet other embodiments, the actual instructions may not be present in the kit, but means for obtaining the instructions from a remote source, e.g. via the internet, are provided. An example of this embodiment is a kit that includes a web address where the instructions can be viewed and/or from which the instructions can be downloaded.

VII. Storage Medium and Device for Detection of Target Nucleic Acid Sequences by Using Multiple Detection Temperatures Since the storage medium, the device and the computer program of the prevent invention described herebelow are intended to perform the present methods in a computer, the common descriptions between them are omitted in order to avoid undue redundancy leading to the complexity of this specification.

In another aspect of this invention, there is provided a computer readable storage medium containing instructions to configure a processor to perform a method for determining the presence of two target nucleic acid sequences in a sample using different detection temperatures, the method comprising:

(a) receiving both a signal detected at a relatively high detection temperature and a signal detected at a relatively low detection temperature, wherein each of the target nucleic acid sequences is detected by a corresponding signal-generating means; wherein a generated signal is detected by using a single type of detector; wherein one of the two target nucleic acid sequences has the relatively high detection temperature and the other has the relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; and (b) determining the presence of the two target nucleic acid sequences by the signal received; wherein (i) the presence of the target nucleic acid sequence having the relatively high detection temperature is determined by the signal detected at the relatively high detection temperature and (ii) the presence of the target nucleic acid sequence having the relatively low detection temperature is determined by a difference between the signal detected at the relatively high detection temperature and the signal detected at the relatively low detection temperature.

According to an embodiment, where the target nucleic acid sequence having the relatively high detection temperature is present, the reference value of the target nucleic acid sequence having the relatively high detection temperature is used to determine the presence of the target nucleic acid sequence having the relatively low detection temperature.

According to an embodiment of the present invention, the reference value of the target nucleic acid sequence having the relatively high detection temperature is stored in the computer readable storage medium. According to an embodiment of the present invention, the computer readable storage medium contains instructions to input the reference value in performing the method. According to an embodiment of the present invention, the computer readable storage medium further contains instructions to configure a processor to perform a method for obtaining the reference value.

In another aspect of this invention, there is provided a computer program to be stored on a computer readable storage medium to configure a processor to perform a method for determining the presence of two target nucleic acid sequences in a sample, the method comprising:

(a) receiving both a signal detected at a relatively high detection temperature and a signal detected at a relatively low detection temperature, wherein each of the target nucleic acid sequences is detected by a corresponding signal-generating means; wherein a generated signal is detected by using a single type of detector; wherein one of the two target nucleic acid sequences has the relatively high detection temperature and the other has the relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; and (b) determining the presence of the two target nucleic acid sequences by the signal received; wherein (i) the presence of the target nucleic acid sequence having the relatively high detection temperature is determined by the signal detected at the relatively high detection temperature and (ii) the presence of the target nucleic acid sequence having the relatively low detection temperature is determined by a difference between the signal detected at the relatively high detection temperature and the signal detected at the relatively low detection temperature.

In still another aspect of this invention, there is provided a computer program stored on a computer readable storage medium to configure a processor to perform a method described above for detection of two target nucleic acid sequences.

According to an embodiment of the present invention, the computer program contains the reference value of the target nucleic acid sequence having the relatively high detection temperature. According to an embodiment of the present invention, the computer program contains instructions to input the reference value in performing the method. According to an embodiment of the present invention, the computer program further contains instructions to configure a processor to perform a method for obtaining the reference value.

The program instructions are operative, when preformed by the processor, to cause the processor to perform the present method described above. The program instructions may comprise an instruction to receive the first signal and the second signal, and an instruction to determine the presence of the two target nucleic acid sequences by using the signals received.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The data (e.g., intensity, amplification cycle number and detection temperature) associated with the signals may be received through several mechanisms. For example, the data may be acquired by a processor resident in a PCR data acquiring device. The data may be provided to the processor in real time as the data is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system. After the data has been received or acquired, the data analysis process proceeds to give a processed signal obtained from a difference between the signals for determination of the presence of target nucleic acid sequences when the signal is detected at the relatively high detection temperature. The processor processes the received data associated with the signals to give the processed signal reflecting the difference between the signals in the two detection temperatures. For example, the processor processes the received data to obtain a ratio of the signal detected at the relatively low detection temperature to the signal detected at the relatively high detection temperature.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In still another aspect of this invention, there is provided a device for detecting a target nucleic acid sequence in a sample using different detection temperatures, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a single type detector to detect signals to be generated by the signal-generating means.

According to an embodiment, the computer processor permits not only the single type of detector to detect signals generated by the signal-generating means at a relatively high detection temperature and a relatively low detection temperature but also to calculate a difference between the signal detected at the relatively high detection temperature and the signal detected at the relatively low detection temperature. The processor may be prepared in such a manner that a single processor can do two performances: direction of detection at two detection temperatures and calculation of the difference. Alternatively, the processor unit may be prepared in such a manner that two processors do two performances, respectively.

The first essential feature of the device carries the processor to permit the device to detect signals to be generated at the two detection temperatures. According to an embodiment, where the signal is generated along with amplification of the target nucleic acid sequence, the device comprises a processor to permit the device to detect signals to be generated at the two detection temperatures at each amplification cycle.

The second essential feature of the device is to carry the processor to process the signal detected at the two detection temperatures to obtain the difference between the signals. According to an embodiment, the difference between the signals is expressed as numeric values by a mathematical processing.

According to an embodiment, the processor may be embodied by installing software into conventional devices for detection of target nucleic acid sequences (e.g. real-time PCR device). According to an embodiment, the device comprises a processor to permit the device to detect signals at at least two detection temperatures and to mathematically process at least two detection results.

In still further aspect of this invention, there is provided a computer readable storage medium containing instructions to configure a processor to perform a method for determining the presence of at least three target nucleic acid sequences in a sample using different detection temperatures, the method comprising:

(a) receiving signals detected at at least three detection temperatures; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein signals to be generated by the signal-generating means are not differentiated by the single type of detector; wherein the detection is performed at each of the different detection temperatures; and (b) determining the presence of the at least three target nucleic acid sequences by the signal received; wherein when the presence of a target nucleic acid sequence having a certain detection temperature among the at least three target nucleic acid sequences is determined, the presence of the target nucleic acid sequence having the certain detection temperature is determined by a difference between the signal detected at one or more detection temperatures higher than the certain detection temperature and the signal detected at the certain detection temperature; wherein when the certain detection temperature is a relatively highest detection temperature among the detection temperatures, the presence of a target nucleic acid sequence is determined by the signal detected at the certain detection temperature.

According to an embodiment of the present invention, reference values are stored in the computer readable storage medium. According to an embodiment of the present invention, the computer readable storage medium contains instructions to input the reference value in performing the method. According to an embodiment of the present invention, the computer readable storage medium further contains instructions to configure a processor to perform a method for obtaining the reference values.

In still another aspect of this invention, there is provided a computer program stored or to be stored on a computer readable storage medium to configure a processor to perform the method described above for detection of at least three target nucleic acid sequences in a sample using different detection temperatures.

In another aspect of this invention, there is provided a computer readable storage medium containing instructions to configure a processor to perform a method for SNP genotyping of a nucleic acid sequence in a sample using different detection temperatures, the method comprising:

(a) receiving both a signal detected at a relatively high detection temperature and a signal detected at a relatively low detection temperature, wherein each of the SNP alleles is detected by a corresponding signal-generating means; wherein one of the SNP alleles has a relatively high detection temperature and the other has a relatively low detection temperature determined by the corresponding signal-generating means; wherein the relatively high detection temperature is a temperature capable of generating a signal for the SNP allele having the relatively high detection temperature and the relatively low detection temperature is a temperature capable of generating both of a signal for the SNP allele having the relatively low detection temperature and a signal for the SNP allele having the relatively high detection temperature;

(b) determining a SNP genotype by a difference between the signals received.

According to an embodiment of the present invention, reference values for a homozygote composed of the SNP allele having the relatively high detection temperature and/or a heterozygote and/or a homozygote composed of the SNP allele having the relatively low detection temperature are stored in the computer readable storage medium. According to an embodiment of the present invention, the computer readable storage medium contains instructions to input the reference value in performing the method. According to an embodiment of the present invention, the computer readable storage medium further contains instructions to configure a processor to perform a method for obtaining the reference values.

In still another aspect of this invention, there is provided a computer program stored or to be stored on a computer readable storage medium to configure a processor to perform the method described above for SNP genotyping of a nucleic acid sequence in a sample using different detection temperatures.

According to an embodiment of the present invention, the computer program contains reference values for a homozygote composed of the SNP allele having the relatively high detection temperature and/or a heterozygote and/or a homozygote composed of the SNP allele having the relatively low detection temperature. According to an embodiment of the present invention, the computer program contains instructions to input the reference value in performing the method. According to an embodiment of the present invention, the computer program further contains instructions to configure a processor to perform a method for obtaining the reference values.

In another aspect of this invention, there is provided a computer readable storage medium containing instructions to configure a processor to perform a method for detecting two target nucleic acid sequences in a sample using different detection temperatures and melting analysis, the method comprising:

(a) receiving both a signal at the relatively high detection temperature for determining the presence of the target nucleic acid sequence having the relatively high detection temperature and a signal from a melting analysis over a range of temperatures for determining the presence of the target nucleic acid sequence having the relatively low detection temperature; wherein each of the target nucleic acid sequences is detected by a corresponding signal-generating means; wherein one of the two target nucleic acid sequences has a relatively high detection temperature and the other has a relatively low detection temperature determined by the corresponding signal-generating means; wherein the relatively high detection temperature is a temperature capable of generating a signal for the target nucleic acid sequence having the relatively high detection temperature and the relatively low detection temperature is a temperature capable of generating both of a signal for the target nucleic acid sequence having the relatively low detection temperature and a signal for the target nucleic acid sequence having the relatively high detection temperature; wherein the melting analysis over a range of temperatures is performed for determining the presence of the target nucleic acid sequence having the relatively low detection temperature; and (b) determining the presence of the two target nucleic acid sequences by the signals received; wherein the presence of the target nucleic acid sequence having the relatively high detection temperature is determined by the signal at the relatively high detection temperature and the presence of the target nucleic acid sequence having the relatively low detection temperature is determined by the signal from the melting analysis.

In still another aspect of this invention, there is provided a computer program stored or to be stored on a computer readable storage medium to configure a processor to perform the method described above for detecting two target nucleic acid sequences in a sample using different detection temperatures and melting analysis.

In another aspect of this invention, there is provided a computer readable storage medium containing instructions to configure a processor to perform a method for detecting at least three target nucleic acid sequences in a sample using detection temperature analysis and melting analysis, the method comprising:

(a) receiving both (i) a signal at a detection temperature of some of the at least three target nucleic acid sequences and one or more detection temperatures higher than the detection temperatures for determining the presence of some of the at least three the target nucleic acid sequences and (ii) a signal from a melting analysis over a range of temperatures for determining the presence of the other target nucleic acid sequences than said some of the at least three the target nucleic acid sequences; wherein each of the at least three target nucleic acid sequences is detected by a corresponding signal-generating means; wherein each of the at least three target nucleic acid sequences has a different detection temperature determined by the corresponding signal-generating means; wherein a detection temperature is a temperature capable of generating not only a signal for a target nucleic acid sequence having the detection temperature but also a signal for a target nucleic acid sequence having a higher detection temperature than the detection temperature; wherein said some of the at least three target nucleic acid sequences are detected by detection temperature analysis and the detection is performed at both the detection temperature of said some of the at least three target nucleic acid sequences and one or more detection temperatures higher than the detection temperatures; wherein the melting analysis over a range of temperatures is performed for determining the presence of the other target nucleic acid sequences than said some of the at least three the target nucleic acid sequences; and (b) determining (i) the presence of said some of the target nucleic acid sequences by the signal received; wherein when the presence of a target nucleic acid sequence having a certain detection temperature among said some of the at least three target nucleic acid sequences is determined, the presence of the target nucleic acid sequence having the certain detection temperature is determined by a difference between the signal detected at one or more detection temperatures higher than the certain detection temperature and the signal detected at the certain detection temperature; wherein when the certain detection temperature is a relatively highest detection temperature among the detection temperatures, the presence of the target nucleic acid sequence is determined by the signal detected at the certain detection temperature; and (ii) the presence of the other target nucleic acid sequences than said some of the at least three target nucleic acid sequences by the signal from the melting analysis.

In still another aspect of this invention, there is provided a computer program stored or to be stored on a computer readable storage medium to configure a processor to perform the method described above for detecting at least three target nucleic acid sequences in a sample using detection temperature analysis and melting analysis.

The features and advantages of this invention will be summarized as follows:

(a) The present invention employing different detection temperatures enables to detect a plurality of target nucleic acid sequences in conventional real-time manners even with a single type of label in a single reaction vessel. The conventional technologies detect a plurality of target nucleic acid sequences by a melting analysis after target amplification. Unlikely, the present invention does not require a melting analysis after target amplification, such that the time for analysis is greatly reduced.

(b) Interestingly, the present inventors have found that when a signal for a target nucleic acid sequence is generated using a signal-generating means, (i) a signal detection at a certain temperature becomes adjustable depending on the type of signal-generating means, and (ii) in the case of detecting signal at selected two detection temperatures, signals detected at the two different detection temperatures are changed in accordance with a certain pattern. The present inventors adopted the findings to detection of target nucleic acid sequences, thereby accomplishing the present invention.

(c) In the present invention using different detection temperatures, for each of target nucleic acid sequences, the use of a signal-generating means to provide a signal by a duplex formed in a dependent manner on cleavage of a mediation oligonucleotide specifically hybridized with a target nucleic acid sequence (e.g., PTOCE-based methods) can induce the unexpected results. First, methods using the mediation oligonucleotide such as the PTOCE-based methods can readily adjust $T_m$ value of duplex formed to ensure convenient selection of detection temperatures. Second, where a method with providing a signal directly from a probe hybridized with a target nucleic acid sequence is employed together with using polymerase having 5'-nuclease activity for target amplification, the probe is likely to be cleaved by the 5'-nuclease activity which may affect interpretation of signals. Because the methods using the mediation oligonucleotide such as the PTOCE-based methods generally use cleavage of the mediation oligonucleotide by the 5'-nuclease activity, such problem associated with interpretation of a resulting signal is typically not generated. Finally, in the methods using the mediation oligonucleotide such as the PTOCE-based methods, a duplex having a certain $T_m$ value can be formed because the duplex has a sequence irrespective of a target nucleic acid sequence. Unlikely, in methods using probes to be directly hybridized with a target nucleic acid sequence, because at least one strand of a duplex formed comprises a sequence complementary to a target nucleic acid sequence, a duplex having $T_m$ value not intended may be formed when a variation on the target nucleic acid sequence is present.

(d) In an embodiment of this invention to detect a plurality of target nucleic acid sequences by use of different detection temperatures in a real-time manner, the combination of (i) for a target nucleic acid sequence, a signal-generating means to generate a signal in a dependent manner on cleavage of a detection oligonucleotide (e.g., TaqMan method) and (ii) for another target nucleic acid sequence, a signal-generating means to provide a signal by a duplex formed in a dependent manner on cleavage of a mediation oligonucleotide specifically hybridized with the target nucleic acid sequence (e.g., PTOCE-based methods) can induce the unexpected results.

The method using cleavage of the detection oligonucleotide generally uses enzyme having 5' nuclease activity (particularly, Taq polymerase) for cleavage of the detection oligonucleotide. In the conventional methods to generate signal by direct hybridization of detection probes (e.g., Molecular beacon method, hybridization probe method or Hybeacon method), the detection probes are very likely to be cleaved by the enzyme having 5' nuclease activity (particularly, Taq polymerase). The cleavage of the detection probes may cause decease in sensitivity due to consumption of the detection probes (e.g., hybridization probe method) or false positive signal in methods with cleavage-dependent signaling (e.g., Molecular beacon method). Although the labeled primer methods (e.g., Sunrise method or Scorpion method) do not suffer from the cleavage as the probe methods, they have shortcomings in which $T_m$ value of amplicon per se has to be controlled to adjust detection temperatures. In contrast, because the PTOCE-based methods employ cleavage of the mediation oligonucleotide specifically hybridized with the target nucleic acid sequence, they are not affected by enzyme having 5' nuclease activity (particularly, Taq polymerase). In addition, the PTOCE-based methods can readily adjust $T_m$ value of duplex formed to ensure convenient selection of detection temperatures.

(e) In an embodiment of this invention to detect a plurality of target nucleic acid sequences in a single reaction vessel by using a real-time detection for some targets and a melting analysis for other targets, signal-generating means suitable to characteristics of a target nucleic acid sequence to be analyzed may be selected and applied, which enables to detect a plurality of target nucleic acid sequences in a much more efficient manner.

(f) In an embodiment of this invention to detect a plurality of target nucleic acid sequences by using a real-time detection and a melting analysis, a signal-generating means to generate a signal in a dependent manner on cleavage of a detection oligonucleotide (e.g., TaqMan method) for a target nucleic acid sequence detected by a real-time manner permits to detect a plurality of target nucleic acid sequences in greatly enhanced convenience and efficiency. The method using cleavage of a detection oligonucleotide as TaqMan method is undergone cleavage of a detection probe. In a certain reaction condition, it may be possible to cleave most of the detection probes. In that case, there is no duplex capable of generating signal in the melting analysis after the real-time reaction, thereby $T_m$ value for other target nucleic acid sequences to be detected by the melting analysis may be easily selected.

(g) In an embodiment of this invention to detect a plurality of target nucleic acid sequences by using a real-time detection and a melting analysis, the combination of (i) for a target nucleic acid sequence, a signal-generating means to generate a signal in a dependent manner on cleavage of a detection oligonucleotide (e.g., TaqMan method) and (ii) for another target nucleic acid sequence, a signal-generating means to provide a signal by a duplex formed in a dependent manner on cleavage of a mediation oligonucleotide specifically hybridized with the target nucleic acid sequence (e.g., PTOCE-based methods) can induce the unexpected results.

According to conventional technologies by use of hybridization between target nucleic acid sequences and detection oligonucleotides, there are serious problems such as sensitivity decrease (including sensitivity decrease in melting analysis) due to probe cleavage and false signal generation due to cleavage. The present invention is completely free from such problems. The PTOCE-based methods can readily adjust $T_m$ value of duplexes used for detection, such that detection temperatures used for real-time detection and peak $T_m$ value used for melting analysis may be readily selected.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Two Target Detection by PTOCE Real-Time PCR Comprising Signal Detection at Different Temperatures We further examined whether two target nucleic acids can be detected in a single reaction vessel by using a single detection channel and PTOCE real-time PCR comprising signal detection at different temperatures.

Taq DNA polymerase having a 5' nuclease activity was used for the extension of upstream primers and downstream primers, the cleavage of PTO, and the extension of PTO fragment. Genomic DNA of *Neisseria gonorrhoeae* (NG) and genomic DNA of *Chlamydia trachomatis* (CT) were used as target nucleic acid sequences.

PTOCE real-time PCR was used to detect CT and NG. If a target is present, a PTO is cleaved and a PTO fragment is produced. The PTO fragment is annealed to the capturing portion of the CTO, extended on the templating portion of the CTO and forms an extended duplex with CTO (Duplexed CTO). The formation of the extended duplex provides a signal and an amplification curve can be obtained by measuring the signal at the extended duplex-forming temperature.

In this Example, "72° C." was selected as a signal detection temperature for CT and "60° C." was selected as a signal detection temperature for NG with consideration of the signal generating means. The extended duplex produced depending on the presence of CT or NG has a controllable Tm value adjusted by its sequence and length. In this Example, the sequence and length of the extended duplex for CT is designed to provide a signal as it forms the duplex at 72° C. Meanwhile, the sequence and length of the extended duplex for NG is designed to provide a signal as it forms the duplex at 60° C., but not to provide a signal as it is dissociated not to forms the duplex at 72° C. In the detection temperature of 72° C., the signal for CT will be generated and detected. In the detection temperature of 60° C., the signal for NG will be generated and detected as well as the signal for CT.

The PTO and CTO are blocked with a carbon spacer at their 3'-ends to prohibit their extension. The CTO is labeled with a quencher molecule (BHQ-2) and a fluorescent reporter molecule (CAL Fluor Red 610) in its templating portion (SEQ ID NOs: 4 and 8).

Four reaction tubes were prepared containing CT, NG, a mixture of CT and NG and no target control respectively.

The sequences of upstream primer, downstream primer, PTO, and CTO used in this Example are:

```
NG-F
                                       (SEQ ID NO: 1)
5'-TACGCCTGCTACTTTCACGCTIIIIIGTAATCAGATG-3'

NG-R
                                       (SEQ ID NO: 2)
5'-CAATGGATCGGTATCACTCGCIIIIICGAGCAAGAAC-3'

NG-PTO
                                       (SEQ ID NO: 3)
5'-GTACGCGATACGGGCCCCTCATTGGCGTGTTTCG[C3
spacer]-3'

NG-CTO
                                       (SEQ ID NO: 4)
5'-[BHQ-2]TTTTTTTTTTTTTTTTTTG[T(CAL Fluor
Red 610)]ACTGCCCGTATCGCGTAC[C3 spacer]-3'

CT-F
                                       (SEQ ID NO: 5)
5'-GAGTTTTAAAATGGGAAATTCTGGTIIIIITTTGTATAAC-3'

CT-R
                                       (SEQ ID NO: 6)
5'-CCAATTGTAATAGAAGCATTGGTTGIIIIITTATTGGAGA-3'

CT-PTO
                                       (SEQ ID NO: 7)
5'-GATTACGCGACCGCATCAGAAGCTGTCATTTTGGCTGCG[C3
spacer]-3'

CT-CTO
                                       (SEQ ID NO: 8)
5'-[BHQ-2]GCGCTGGATACCCTGGACGA[T(CAL Fluor Red
610)]ATGTGCGGTCGCGTAATC[C3 spacer]-3'
```

(I: Deoxyinosine)
(Underlined letters indicate the 5'-tagging portion of PTO)

The real-time PCR was conducted in the final volume of 20 µl containing a target nucleic acid (10 pg of NG genomic DNA, 10 pg of CT genomic DNA or a mixture of 10 pg of NG genomic DNA and 10 pg of CT genomic DNA), 5 pmole of upstream primer (SEQ ID NO: 1) and 5 pmole of downstream primer (SEQ ID NO: 2) for NG target amplification, 3 pmole of PTO (SEQ ID NO: 3), 1 pmole of CTO (SEQ ID NO: 4), pmole of upstream primer (SEQ ID NO: 5) and 5 pmole of downstream primer (SEQ ID NO: 6) for CT target amplification, 3 pmole of PTO (SEQ ID NO: 7), 1 pmole of CTO (SEQ ID NO: 8), and 10 µl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C. and 72° C. of each cycle.

As shown in FIG. 1A, signals were detected at 72° C. in the presence of CT (Tubes 1 and 3). In the sole presence of NG, a signal was detected at 60° C. but not at 72° C. (Tube 2). No signal was detected in the absence of the target nucleic acids (Tube 4). The results of FIG. 1A show that the signal for CT having the relatively high detection temperature is generated, but the signal for NG having the relatively low detection temperature not generated at the relatively high detection temperature, 72° C. Therefore, it would be appreciated that the signal detection at the relatively high detection temperature allowed determining at least the presence of CT having the relatively high detection temperature.

Also, in Tube 2, using the difference due to the absence of a signal at the relatively high detection temperature and the presence of a signal at the relatively low detection temperature allowed determining the presence of NG having the relatively low detection temperature.

The difference between the signals detected at the relatively high detection temperature and the relatively low detection temperature was calculated by various approaches in order to examine whether the presence of NG having the relatively low detection temperature can be detected even in the presence or absence of the signal from CT having the relative high detection temperature (FIG. 1B~1E).

The FIG. 1B shows the ratio of the RFU values of the end points at 72° C. and 60° C. (All RFU values were derived and exported from "Baseline subtracted curve fit" analysis data in instrumental software). The ratio in the sole presence of CT (Tube 1) was 1.2 but, that in the presence of both CT and NG (Tube 3) was 2.1. Also, the ratio in the sole presence of NG (Tube 2) and in absence of any target nucleic acid (Tube 4) was 36.7 and 0.7, respectively. A threshold, 1.5, was applied to determine the presence or absence of NG. In accordance with the threshold, the presence of NG was confirmed in Tubes 2 and 3, and there is no NG in Tubes 1 and 4. The threshold was determined with considering the end-ratio from the tube containing only CT. As Tube 2, where CT having the relatively high detection temperature can be determined to be absent, the threshold for signal at the relatively low detection temperature may be independently set instead of applying 1.5.

Figure 1C:
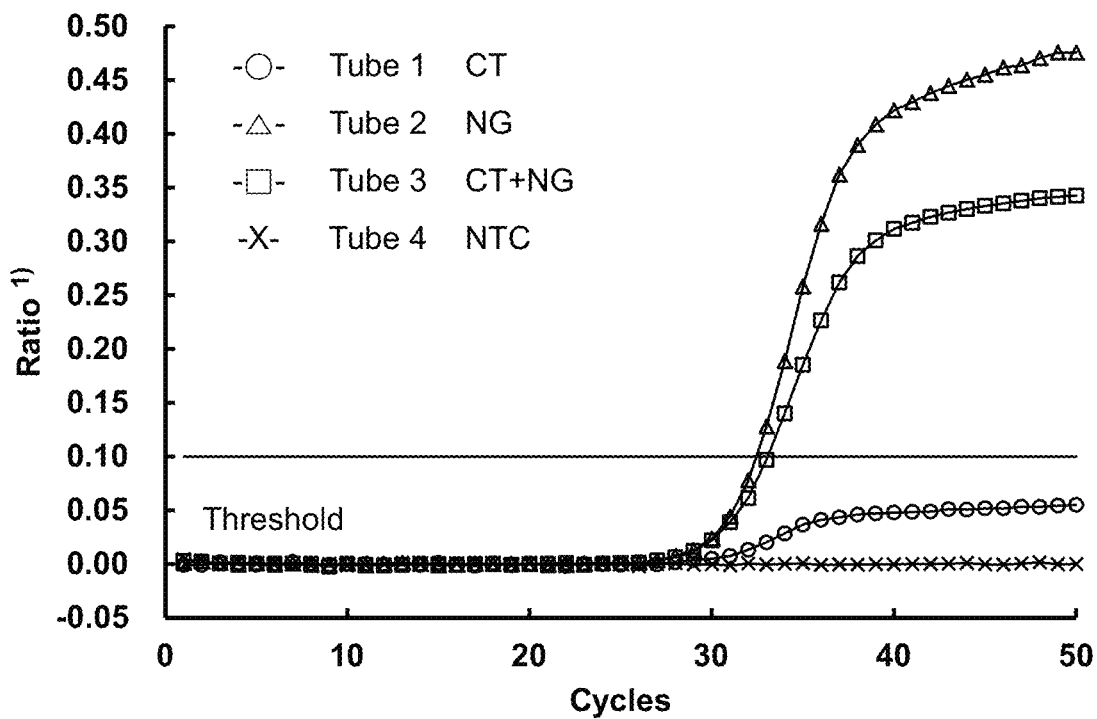
FIG. 1c represents determination of the presence of the target nucleic acid sequences having a relatively low detection temperature by plotting the ratios between the signal at the relatively high detection temperature and the signal at the relatively low detection temperature.

Another approach using the signals at 72° C. and 60° C. is to calculate the ratio of the fluorescence signals at 72° C. and 60° C. in each of cycles and plot the ratio against the cycle (All RFU values processed for the plotting were derived and exported from "No baseline subtraction" analysis data in instrumental software). Threshold, 0.1, was applied to determine the presence or absence of NG. The threshold was determined with considering the ratio plot from the tube containing only CT. As shown in FIG. 1C, the presence of NG was ascertained in Tubes 2 and 3 and its $C_t$ value were 32.90 and 33.18, respectively. There is no $C_t$ value obtained in Tubes 1 and 4. Instead of calculating the ratios, the fluorescent intensity at 60° C. may be subtracted from that at 72° C. in each of cycles and plot the results against the cycle for the target detection.

Application of individual thresholds for the analysis of the signals obtained at 60° C. in each tube is other method to detect the presence of NG having the relatively low detection temperature by using the signal indicating the presence of CT at the relatively high detection temperature. In the case that the signal is detected at 72° C., the individual threshold for the signal at 60° C. from tubes were calculated by multiplying each End-RFU value at 72° C. by a threshold (1.5). The threshold (1.5) was determined with considering the end-ratio from the tube containing only CT (refer to FIG. 1B). In the case that the signal is not detected at 72° C., the individual threshold for the signal at 60° C. from tubes was chosen and used with consideration of the background signal, sensitivity, and signal variation or error range of device, according to the general setting of a threshold. In this Example, "200" was determined as an individual threshold for the signal at 60° C.

Figure 1D:
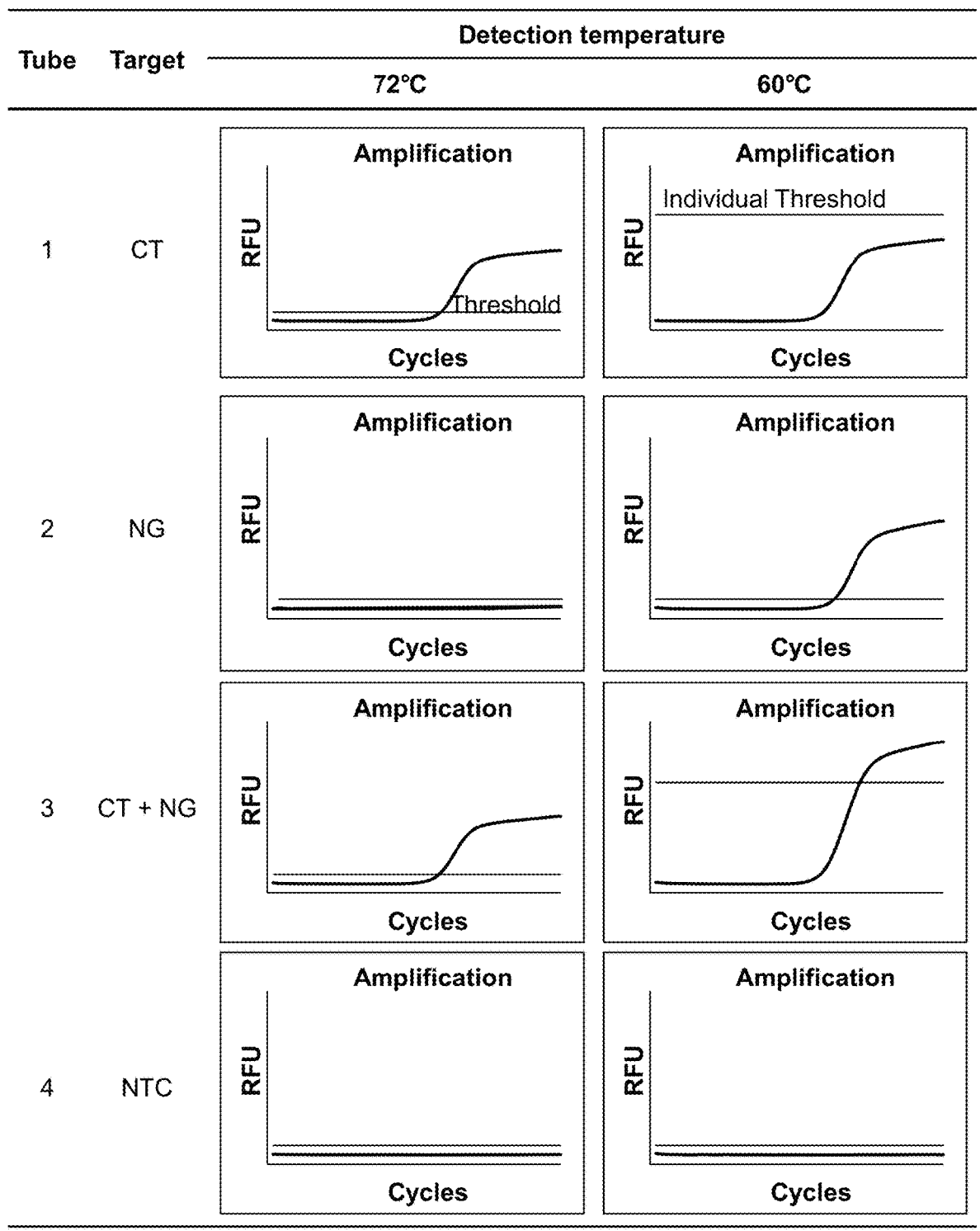

As shown in FIG. 1D and FIG. 1E, according to the individual threshold at 60° C., the presence of NG was confirmed in Tube 2 and Tube 3 and furthermore, its $C_t$ value were obtained as 31.32 and 35.83, respectively. No $C_t$ value for NG was available in Tubes 1 and 4.

These results indicate that in the PTOCE real-time method comprising signal detection at two temperatures, (i) the signal detection at the relatively high detection temperature allows detecting the target nucleic acid sequence having the relatively high detection temperature and (ii) the signals obtained at the relatively high detection temperature and the relatively low detection temperature can be used to detect the target nucleic acid sequence having the relatively low detection temperature.

Therefore, two target nucleic acids can be detected in a single reaction vessel by using a single detection channel and PTOCE real-time PCR comprising signal detection at different temperatures.

Example 2: Two Target Detection by TaqMan/PTOCE Real-Time PCR Comprising Signal Detection at Different Temperatures We examined whether two target nucleic acids can be detected in a single reaction vessel by using a single detection channel and TaqMan/PTOCE real-time PCR comprising signal detection at different temperatures.

Taq DNA polymerase having a 5' nuclease activity was used for the extension of upstream primers and downstream primers, the cleavage of TaqMan probe, the cleavage of PTO, and the extension of PTO fragment. Genomic DNA of *Neisseria gonorrhoeae* (NG) and genomic DNA of *Chlamydia trachomatis* (CT) were used as target nucleic acid sequences.

TaqMan real-time PCR was employed to detect CT. If CT is present, a TaqMan probe is cleaved and a labeled fragment is released. An amplification curve can be obtained by measuring a signal from the labeled fragment. PTOCE real-time PCR was used to detect NG.

In this Example, "72° C." was selected as a signal detection temperature for CT and "60° C." was selected as a signal detection temperature for NG with consideration of the signal generating means. The extended duplex produced depending on the presence of NG has a controllable Tm value adjusted by its sequence and length. In this Example, the sequence and length of the extended duplex is designed to provide a signal as it forms the duplex at 60° C., but not to provide a signal as it is dissociated not to forms the duplex at 72° C. In the detection temperature of 72° C., the signal for CT will be generated and detected. In the detection temperature of 60° C., the signal for NG will be generated and detected as well as the signal for CT.

TaqMan probe is labeled with a fluorescent reporter molecule (CAL Fluor Red 610) at its 5'-end and a quencher molecule at its 3'-end (BHQ-2) (SEQ ID NO: 9). The PTO and CTO are blocked with a carbon spacer at their 3'-ends to prohibit their extension. The CTO is labeled with a quencher molecule (BHQ-2) and a fluorescent reporter molecule (CAL Fluor Red 610) in its templating portion (SEQ ID NO: 4).

Four reaction tubes were prepared containing CT, NG, a mixture of CT and NG and no target control respectively.

The sequences of upstream primer, downstream primer, PTO, CTO, and TaqMan probe used in this Example are:

NG-F
(SEQ ID NO: 1)
5'-TACGCCTGCTACTTTCACGCTIIIIIGTAATCAGATG-3'

NG-R
(SEQ ID NO: 2)
5'-CAATGGATCGGTATCACTCGCIIIIICGAGCAAGAAC-3'

NG-PTO
(SEQ ID NO: 3)
5'-<u>GTACGCGATACGGG</u>CCCCTCATTGGCGTGTTTCG[C3 spacer]-3'

NG-CTO
(SEQ ID NO: 4)
5'-[BHQ-2]TTTTTTTTTTTTTTTTTTG[T(CAL Fluor Red 610)]ACTGCCCGTATCGCGTAC[C3 spacer]-3'

CT-F
(SEQ ID NO: 5)
5'-GAGTTTTAAAATGGGAAATTCTGGTIIIIITTTGTATAAC-3'

CT-R
(SEQ ID NO: 6)
5'-CCAATTGTAATAGAAGCATTGGTTGIIIIITTATTGGAGA-3'

CT-P
(SEQ ID NO: 9)
5'-[CAL Fluor Red 610]CATCAGAAGCTGTCATTTTGGCTGCG[BHQ-2]-3'

(I: Deoxyinosine)
(Underlined letters indicate the 5'-tagging portion of PTO)

The real-time PCR was conducted in the final volume of 20 µl containing a target nucleic acid (10 pg of NG genomic DNA, 10 pg of CT genomic DNA or a mixture of 10 pg of NG genomic DNA and 10 pg of CT genomic DNA), 10 pmole of upstream primer (SEQ ID NO: 1) and 10 pmole of downstream primer (SEQ ID NO: 2) for NG target amplification, 5 pmole of PTO (SEQ ID NO: 3), 1 pmole of CTO (SEQ ID NO: 4), pmole of upstream primer (SEQ ID NO: 5) and 12 pmole of downstream primer (SEQ ID NO: 6) for CT target amplification, 1 pmole of TaqMan probe (SEQ ID NO: 9), and 10 µl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C. and 72° C. of each cycle.

Figure 2A:
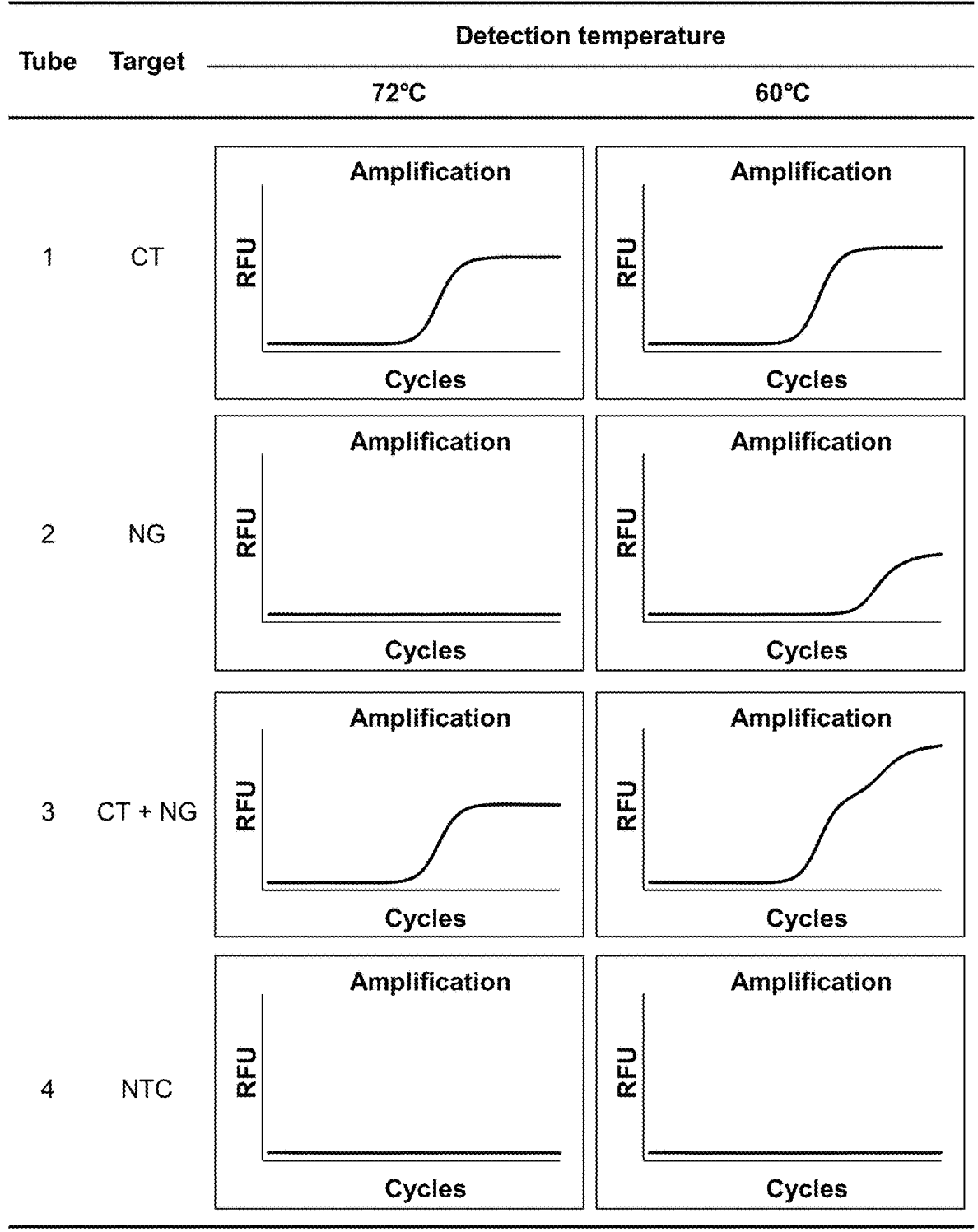
FIG. 2a represents the detection results of the present invention using different detection temperatures to detect a target nucleic acid sequence (genome DNA of *Chlamydia trachomatis*, CT) having a relatively high detection temperature (72° C.), a target nucleic acid sequence (genome DNA of *Neisseria gonorrhoeae*, NG) having a relatively low detection temperature (60° C.) and their combination. The signal for CT was generated by TaqMan real-time PCR method, and the signal for NG was generated by PTOCE real-time PCR method.

As shown in FIG. 2A, signals were detected at 72° C. in the presence of CT (Tubes 1 and 3). In the sole presence of NG, a signal was detected at 60° C. but not at 72° C. (Tube 2). No signal was detected in the absence of the target nucleic acids (Tube 4). The results of FIG. 2A show that the signal for CT having the relatively high detection temperature is generated, but the signal for NG having the relatively low detection temperature not generated at the relatively high detection temperature, 72° C. Therefore, it would be appreciated that the signal detection at the relatively high detection temperature allowed determining at least the presence of CT having the relatively high detection temperature. Also, in the Tube 2, using the difference due to the absence of a signal at the relatively high detection temperature and the presence of a signal at the relatively low detection temperature allowed determining the presence of NG having the relatively low detection temperature.

The difference between the signals detected at the relatively high detection temperature and the relatively low detection temperature was calculated by various approaches in order to examine whether the presence of NG having the relatively low detection temperature can be detected even in the presence or absence of the signal from CT having the relative high detection temperature (FIG. 2B~2E).

The FIG. 2B shows the ratio of the RFU values of the end points at 72° C. and 60° C. (All RFU values were derived and exported from "Baseline subtracted curve fit" analysis data in instrumental software). The ratio in the sole presence of CT (Tube 1) was 1.1 but, that in the presence of both CT and NG (Tube 3) was 1.8. Also, the ratio in the sole presence of NG (Tube 2) and in absence of any target nucleic acid (Tube 4) was 1278.0 and 1.0, respectively. A threshold, 1.2, was applied to determine the presence or absence of NG. In accordance with the threshold, the presence of NG was confirmed in Tubes 2 and 3, and there is no NG in Tubes 1 and 4. The threshold was determined with considering the end-ratio from the tube containing only CT. Alternatively, as Tube 2, where CT having the relatively high detection temperature can be determined to be absent, the threshold for signal at the relatively low detection temperature may be independently set instead of applying 1.2.

Figure 2C:
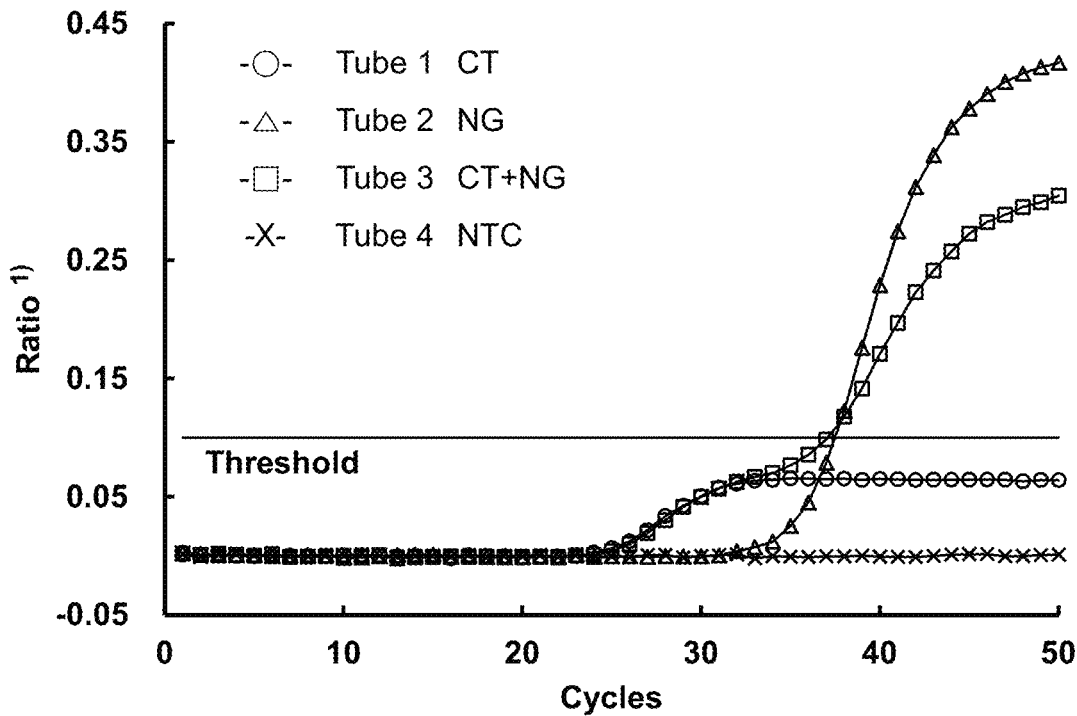
FIG. 2c represents determination of the presence of the target nucleic acid sequences having a relatively low detection temperature by plotting the ratios between the signal at the relatively high detection temperature and the signal at the relatively low detection temperature.

Another approach using the signals at 72° C. and 60° C. is to calculate the ratio of the fluorescence signals at 72° C. and 60° C. in each of cycles and plot the ratio against the cycle (All RFU values processed for the plotting were derived and exported from "No baseline subtraction" analysis data in instrumental software). Threshold, 0.1, was applied to determine the presence or absence of NG. The threshold was determined with considering the ratio plot from the tube containing only CT. As shown in FIG. 2C, the presence of NG was ascertained in Tubes 2 and 3 and its $C_t$ value were 37.88 and 37.20, respectively. There is no $C_t$ value obtained in Tubes 1 and 4. Instead of calculating the ratios, the fluorescent intensity at 60° C. may be subtracted from that at 72° C. in each of cycles and plot the results against the cycle for the target detection.

Application of individual thresholds for the analysis of the signals obtained at 60° C. in each tube is other method to detect the presence of NG having the relatively low detection temperature by using the signal at the relatively high detection temperature. In the case that the signal indicating the presence of CT is detected at 72° C., the individual threshold for the signal at 60° C. from tubes were calculated by multiplying each End-RFU value at 72° C. by a threshold (1.2). The threshold (1.2) was determined with considering the end-ratio from the tube containing only CT (refer to FIG. 2B). In the case that the signal is not detected at 72° C., the individual threshold for the signal at 60° C. from tubes was chosen and used with consideration of the background signal, sensitivity, and signal variation or error range of device, according to the general setting of a threshold. In this Example, "200" was determined as an individual threshold for the signal at 60° C.

Figure 2D:
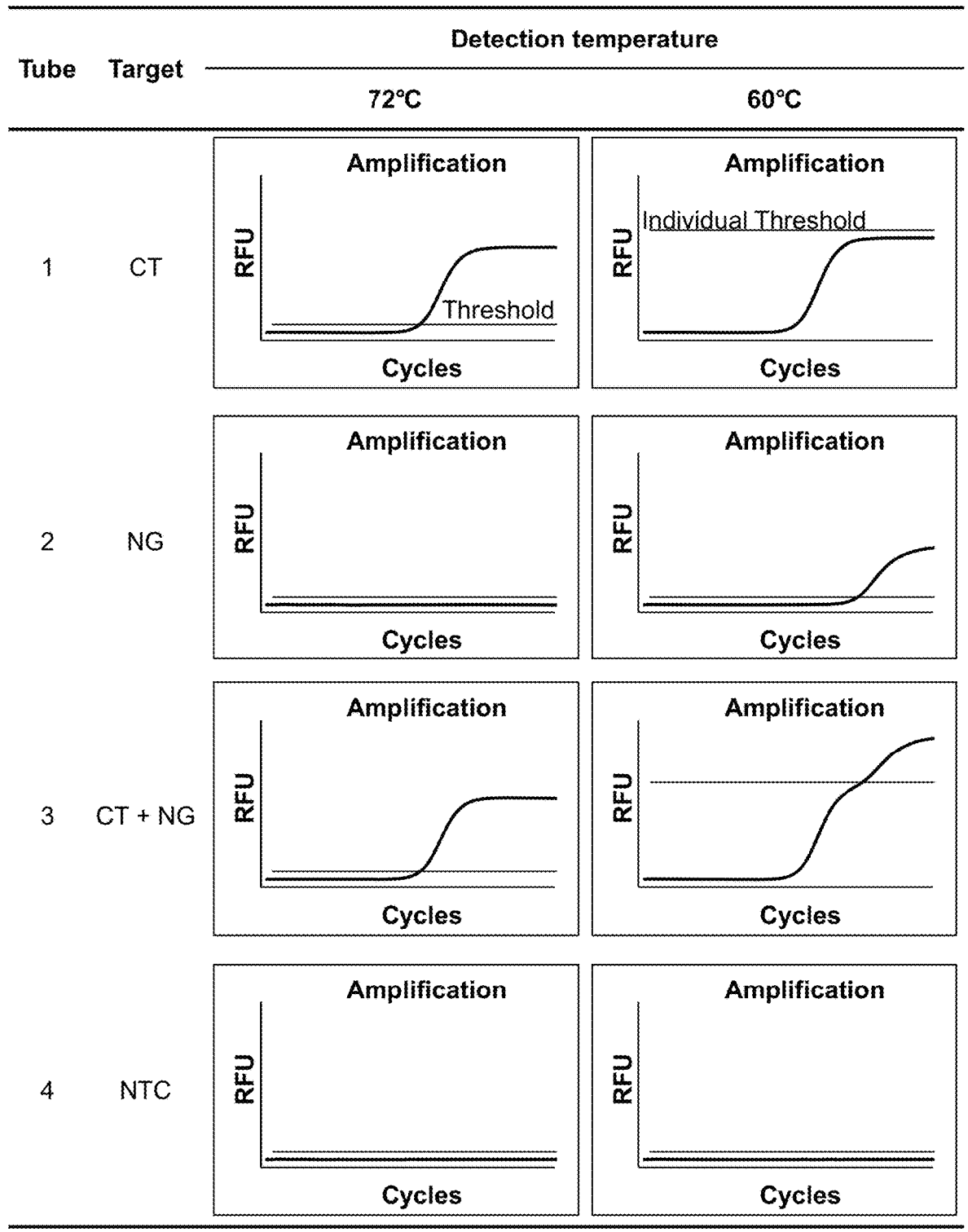

As shown in FIG. 2D and FIG. 2E, according to the individual threshold at 60° C., the presence of NG was confirmed in Tube 2 and Tube 3 and, furthermore, its $C_t$ value were obtained as 36.21 and 37.07, respectively. No $C_t$ value for NG was available in Tubes 1 and 4.

These results indicate that in the TaqMan/PTOCE real-time method comprising signal detection at two temperatures, (i) the signal detection at the relatively high detection temperature allows detecting the target nucleic acid sequence having the relatively high detection temperature and (ii) the signals obtained at the relatively high detection temperature and the relatively low detection temperature can be used to detect the target nucleic acid sequence having the relatively low detection temperature.

Therefore, two target nucleic acids can be detected in a single reaction vessel by using a single detection channel and TaqMan/PTOCE real-time PCR comprising signal detection at different temperatures.

Example 3: Two Target Detection by Real-Time PCR and Melting Analysis

We examined whether two target nucleic acids can be detected in a single reaction vessel by using a single detection channel and combination of real-time PCR and melting analysis.

Taq DNA polymerase having a 5' nuclease activity was used for the extension of upstream primers and downstream primers, the cleavage of TaqMan probe, the cleavage of PTO, and the extension of PTO fragment. Genomic DNA of *Neisseria gonorrhoeae* (NG) and genomic DNA of *Chlamydia trachomatis* (CT) were used as target nucleic acid sequences.

TaqMan real-time PCR was employed to detect CT and PTOCE melting analysis was used to detect NG. If CT is present, a TaqMan probe is cleaved and a labeled fragment is released. If NG is present, a PTO is cleaved and a PTO fragment is produced. The PTO fragment is annealed to the capturing portion of the CTO, extended on the templating portion of the CTO and forms an extended duplex with the CTO (Duplexed CTO).

In order to detect only the florescent signal generated by cleavage of TaqMan probe during real-time PCR process, the fluorescent signal detection is performed, at the temperature where the extended duplex is dissociated not to form the duplex and the signal from the extended duplex formed by PTOCE is not generated. In the melting process, a signal is measured to obtain a melting peak indicating the presence of the extended duplex formed depending on the presence of NG.

TaqMan probe is labeled with a fluorescent reporter molecule (CAL Fluor Red 610) at its 5'-end and a quencher molecule at its 3'-end (BHQ-2) (SEQ ID NO: 9). The PTO and CTO are blocked with a carbon spacer at their 3'-ends to prohibit their extension. The CTO is labeled with a quencher molecule (BHQ-2) and a fluorescent reporter molecule (CAL Fluor Red 610) in its templating portion (SEQ ID NO: 4).

The sequences of upstream primer, downstream primer, PTO, CTO, and TaqMan probe used in this Example are:

```
NG-F
                                           (SEQ ID NO: 1)
5'-TACGCCTGCTACTTTCACGCTIIIIIGTAATCAGATG-3'

NG-R
                                           (SEQ ID NO: 2)
5'-CAATGGATCGGTATCACTCGCIIIIICGAGCAAGAAC-3'

NG-PTO
                                           (SEQ ID NO: 3)
5'-GTACGCGATACGGGCCCCTCATTGGCGTGTTTCG[C3
spacer]-3'

NG-CTO
                                           (SEQ ID NO: 4)
5'-[BHQ-2]TTTTTTTTTTTTTTTTTTTG[T(CAL Fluor
Red 610)]ACTGCCCGTATCGCGTAC[C3 spacer]-3'

CT-F
                                           (SEQ ID NO: 5)
5'-GAGTTTTAAAATGGGAAATTCTGGTIIIIITTTGTATAAC-3'

CT-R
                                           (SEQ ID NO: 6)
5'-CCAATTGTAATAGAAGCATTGGTTGIIIIITTATTGGAGA-3'
```

```
CT-P
                                            (SEQ ID NO: 9)
5'-[CAL Fluor Red 610]CATCAGAAGCTGTCATTTTGGCTGCG
[BHQ-2]-3'
```

(I: Deoxyinosine)
(Underlined letters indicate the 5'-tagging portion of PTO)

The real-time PCR was conducted in the final volume of 20 µl containing a target nucleic acid (10 pg of NG genomic DNA, 10 pg of CT genomic DNA or a mixture of 10 pg of NG genomic DNA and 10 pg of CT genomic DNA), 10 pmole of upstream primer (SEQ ID NO: 1) and 10 pmole of downstream primer (SEQ ID NO: 2) for NG target amplification, 5 pmole of PTO (SEQ ID NO: 3), 1 pmole of CTO (SEQ ID NO: 4), pmole of upstream primer (SEQ ID NO: 5) and 12 pmole of downstream primer (SEQ ID NO: 6) for CT target amplification, 1 pmole of TaqMan probe (SEQ ID NO: 9), and 10 µl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 72° C. of each cycle. After the reaction, the tube was placed for 5 min at 55° C. Melting curve analysis was performed by measuring a florescent signal during the temperature rise from 55° C. to 95° C. in an interval of 0.5° C.

Figure 3:
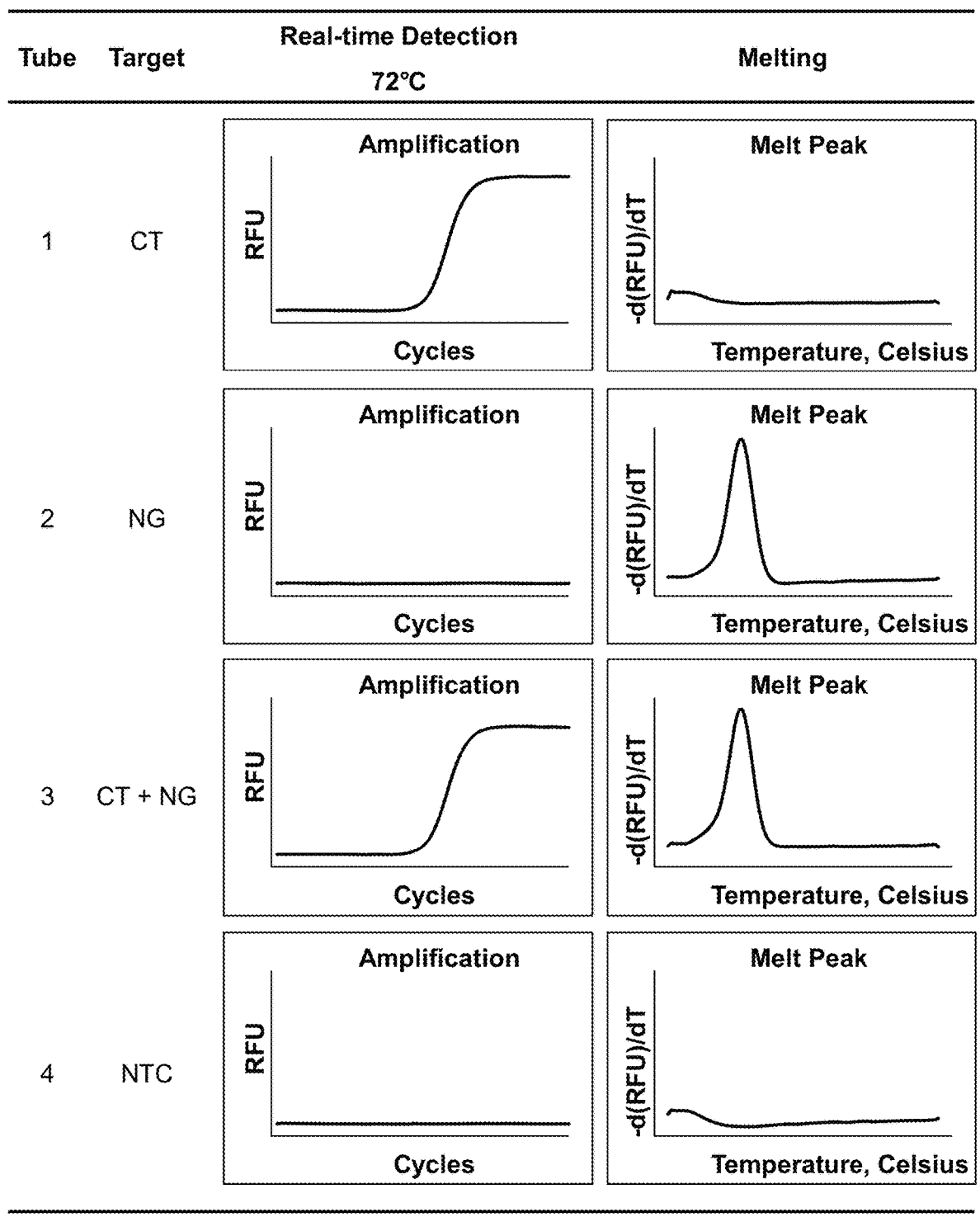
FIG. 3 represents the detection results of a target nucleic acid sequence (genome DNA of *Chlamydia trachomatis*, CT) having a relatively high detection temperature (72° C.), a target nucleic acid sequence (genome DNA of *Neisseria gonorrhoeae*, NG) having a relatively low detection temperature (60° C.) and their combination in accordance with both a real-time PCR using different detection temperatures and a melting analysis. The signal for CT was generated by TaqMan real-time PCR method, and the signal for NG was generated by PTOCE-melting method.

As shown in FIG. 3, in the presence of CT, an amplification curve was obtained during the real-time PCR, but no melting peak was observed in the melting analysis (Tube 1). In the presence of NG, an amplification curve was not obtained during the real-time PCR, but a melting peak having the expected Tm value (66° C.) of the extended duplex formed depending on the presence of NG was observed in the melting analysis (Tube 2). In the presence of CT and NG, signals were observed during both real-time PCR process and melting analysis process (Tube 3). No signal was detected in the absence of the target nucleic acids (Tube 4).

These results indicate that a plural of target nucleic acids can be detected with a single detection channel by combination of real-time PCR and melting analysis.

Example 4: SNP Genotyping by Real-Time PCR Comprising Signal Detection at Different Temperatures We examined whether a real-time PCR comprising signal detection at a different temperature can be applied to SNP genotyping in a single reaction vessel by using a single detection channel.

Taq DNA polymerase having a 5' nuclease activity was used for the extension of upstream primer and downstream primer, the cleavage of PTO, and the extension of PTO fragment. Wild (C) homozygote, mutant type (T) homozygote, and heterozygote of MTHFR (C677T) human genomic DNA were used as target nucleic acid sequences.

PTOCE real-time PCR was used to detect the wild (C) allele and mutant type (T) allele of the MTHFR (C677T) human genomic DNA. If a target allele is present, a PTO is cleaved and a PTO fragment is produced. The PTO fragment is annealed to the capturing portion of the CTO, extended on the templating portion of the CTO and forms an extended duplex with CTO (Duplexed CTO). The formation of the extended duplex provides a signal and an amplification curve can be obtained by measuring the signal at the extended duplex-forming temperature.

In this Example, "72° C." was selected as a signal detection temperature for the wild (C) allele and "55° C." was selected as a signal detection temperature for the mutant type (T) allele with consideration of the signal generating means. The extended duplex produced depending on the presence of the wild (C) allele or the mutant type (T) allele has a controllable Tm value adjusted by their sequence and length. In this Example, the sequence and length of the extended duplex for the wild (C) allele is designed to provide a signal as it forms the duplex at 72° C. Meanwhile, the sequence and length of the extended duplex for the mutant type (T) allele is designed to provide a signal as it forms the duplex at 55° C., but not to provide a signal as it is dissociated not to forms the duplex at 72° C. In the detection temperature of 72° C., the signal for the wild (C) allele will be generated and detected. In the detection temperature of 55° C., the signal for the mutant type (T) allele will be generated and detected as well as the signal for the wild (C) allele.

The PTO and CTO are blocked with a carbon spacer at their 3'-ends to prohibit their extension. The CTO is labeled with a quencher molecule (BHQ-2) and a fluorescent reporter molecule (CAL Fluor Red 610) in its templating portion (SEQ ID NOs: 13 and 15).

The sequences of upstream primer, downstream primer, PTO, and CTO used in this Example are:

```
M677-F
                                           (SEQ ID NO: 10)
5'-CCACCCCGAAGCAGGGAIIIIIGAGGCTGACC-3'

M677-R
                                           (SEQ ID NO: 11)
5'-CAAGTGATGCCCATGTCGGIIIIIGCCTICACAA-3'

M677-W-PTO
                                           (SEQ ID NO: 12)
5'-GGTCCCGACGTTAGCTCCCGCAGACACCTTCTCCTTC[C3
spacer]-3'

M677-W-CTO
                                           (SEQ ID NO: 13)
5'-[BHQ-2]CCTCGGTGCCACGCCATCGG[T(CAL Fluor
Red 610)]TCTTCTAACGTCGGGACC[C3 spacer]-3'

M677-M-PTO
                                           (SEQ ID NO: 14)
5'-ACGTCGATTCGCACTCCCGCAGACACCTTCTCCTTCAA
[C3 spacer]-3'

M677-M-CTO
                                           (SEQ ID NO: 15)
5'-[BHQ-2]TTTTTTTTTTTTTTTTTTT[T(CAL Fluor
Red 610)]ATTCTGCGAATCGACGT[C3 spacer]-3'
```

(I: Deoxyinosine)
(Underlined letters indicate the 5'-tagging portion of PTO)

The real-time PCR was conducted in the final volume of 20 µl containing a target nucleic acid (1 ng of wild (C) homozygous MTHFR (C677T) human genomic DNA, 1 ng of mutant (T) homozygous MTHFR (C677T) human genomic DNA, or 1 ng of heterozygous MTHFR (C677T) human genomic DNA), 5 pmole of upstream primer (SEQ ID NO: 10) and 5 pmole of downstream primer (SEQ ID NO: 11), 3 pmole of each PTO (SEQ ID NOs: 12 and 14), 1 pmole of each CTO (SEQ ID NOs: 13 and 15), and 10 µl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 55° C., 30 sec at 72° C. Detection of a signal was performed at 55° C. and 72° C. of each cycle.

Figure 4A:
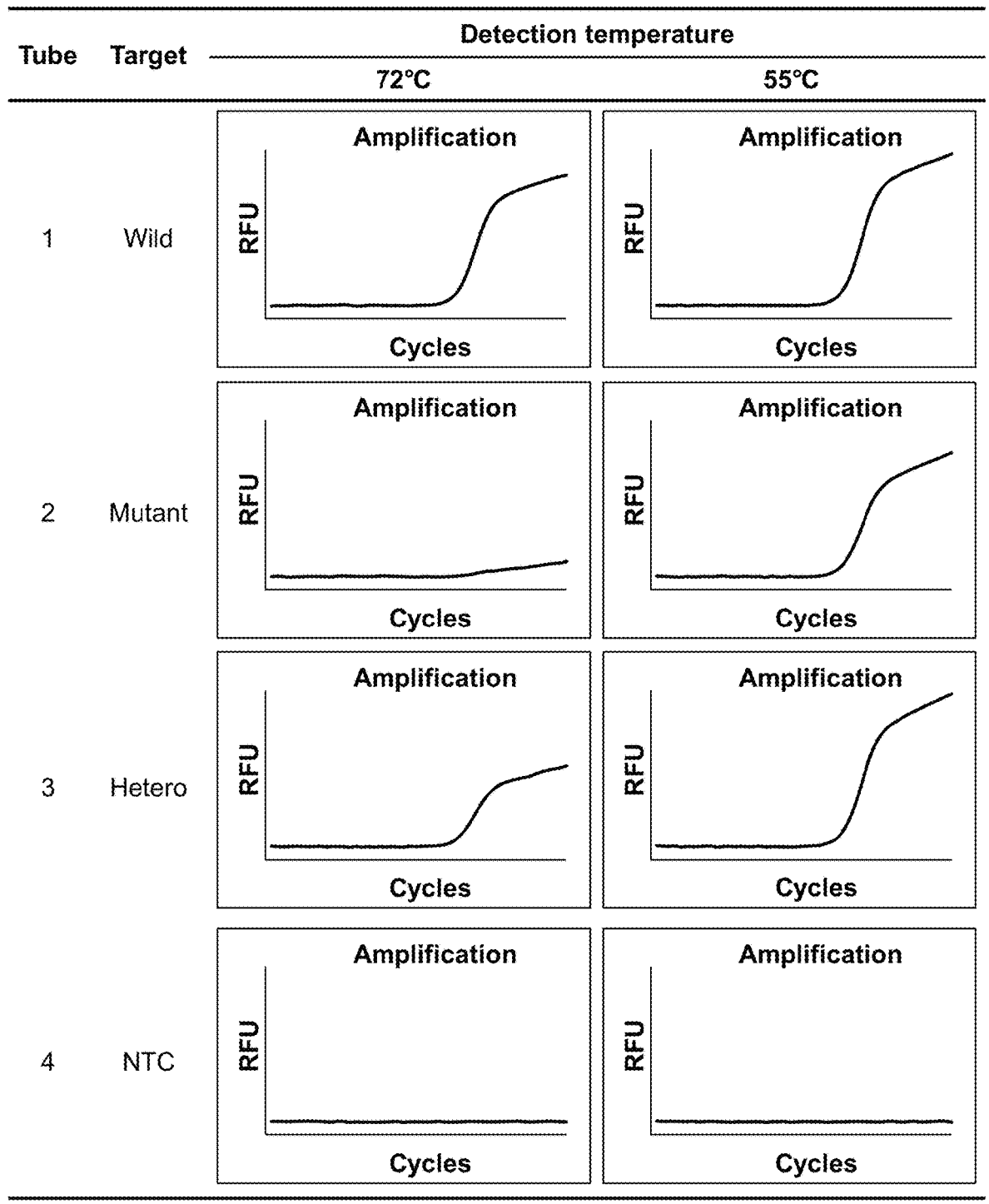
FIG. 4a represents the SNP genotyping results of the present invention using different detection temperatures in a real-time PCR manner. MTHFR(C677T) human genomic DNA was used as templates (target sequences). The wild homozygote (CC), the mutant homozygote (TT) and the heterozygote (CT) were detected. All signals were generated by PTOCE real-time PCR method.

As shown in FIG. 4A, signals were detected at 72° C. and 55° C. in the presence of the wild (C) homozygote (Tube 1) or in the presence of the heterozygote (Tube 3). In the presence of the mutant (T) homozygote, an intense signal was detected at 55° C. but a very weak signal at 72° C. (Tube 2). No signal was detected in the absence of the target nucleic acids (Tube 4).

The FIG. 4B shows the ratio of the RFU values of the end points at 72° C. and 55° C. (All RFU values were derived and exported from "Baseline subtracted curve fit" analysis data in instrumental software). The ratio in the presence of the wild (C) homozygote (Tube 1) was 1.2 but, that in the presence of the heterozygote (Tube 3) was 1.9. Such difference between the two ratios indicates that the mutant (T) allele exists with the wild (C) allele in the tube comprising the heterozygote. Meanwhile, the ratio obtained from the mutant (T) homozygote was relatively very large, as the RFU value in 72° C. was low (Tube 2). Considering the fact that a wild allele and a mutant allele are present in the ratio of 1:1 in a heterozygote, the weak signal detected at 72° C. in the presence of mutant type homozygote can be appreciated to be a false positive signal. According to the present method for SNP genotyping, the ratio value serves to determine whether the signal at the relative high detection temperature is a false signal or not.

These results indicate that a real-time PCR comprising signal detection at a different temperature can be applied to SNP genotyping with a single detection channel and that the difference obtained from signals at the relatively high detection temperature and the relatively low detection temperature can be used for SNP genotyping.

Example 5: Multiple Target Detection by TaqMan/PTOCE Real-Time PCR Comprising Signal Detection at Different Temperatures We examined whether triple target nucleic acids can be detected in a single reaction vessel by using a single detection channel and TaqMan/PTOCE real-time PCR comprising signal detection at different temperatures.

Taq DNA polymerase having a 5' nuclease activity was used for the extension of upstream primers and downstream primers, the cleavage of TaqMan probe, the cleavage of PTO, and the extension of PTO fragment. Genomic DNA of *Neisseria gonorrhoeae* (NG), genomic DNA of *Chlamydia trachomatis* (CT), and genomic DNA of *Mycoplasma genitalium* (MG) were used as target nucleic acid sequences.

TaqMan real-time PCR was employed to detect MG. PTOCE real-time PCR was used to detect CT and NG.

In this Example, "95° C." was selected as a signal detection temperature for MG, "72° C." was selected as a signal detection temperature for CT, and "60° C." was selected as a signal detection temperature for NG with consideration of the signal generating means. In this Example, the sequence and length of the extended duplex of CT or NG is designed to provide a signal as it forms the duplex at 72° C. or 60° C., respectively, but not to provide a signal as it is dissociated not to forms the duplex at 95° C. In the detection temperature of 95° C., the signal for MG will be generated and detected. In the detection temperature of 72° C., the signal for CT will be generated and detected as well as the signal for MG. Also, in the detection temperature of 60° C., the signal for NG will be generated and detected as well as the signal for MG and CT.

TaqMan probe is labeled with a fluorescent reporter molecule (CAL Fluor Red 610) at its 5'-end and a quencher molecule at its 3'-end (BHQ-2) (SEQ ID NO: 18). The PTO and CTO are blocked with a carbon spacer at their 3'-ends to prohibit their extension. CTO is labeled with a quencher molecule (BHQ-2) and a fluorescent reporter molecule (CAL Fluor Red 610) in its templating portion (SEQ ID NOs: 4 and 8).

Eight reaction tubes were prepared containing NG, CT, MG, a mixture of NG and CT, a mixture of NG and MG, a mixture of CT and MG, a mixture of NG, CT and MG, and no target control respectively.

The sequences of upstream primer, downstream primer, PTO, CTO and TaqMan probe used in this Example are:

NG-F
(SEQ ID NO: 1)
5'-TACGCCTGCTACTTTCACGCTIIIIIGTAATCAGATG-3'

NG-R
(SEQ ID NO: 2)
5'-CAATGGATCGGTATCACTCGCIIIIICGAGCAAGAAC-3'

NG-PTO
(SEQ ID NO: 3)
5'-<u>GTACGCGATACGGG</u>CCCCTCATTGGCGTGTTTCG[C3 spacer]-3'

NG-CTO
(SEQ ID NO: 4)
5'-[BHQ-2]TTTTTTTTTTTTTTTTTG[T(CAL Fluor Red 610)]ACTGCCCGTATCGCGTAC[C3 spacer]-3'

CT-F
(SEQ ID NO: 5)
5'-GAGTTTTAAAATGGGAAATTCTGGTIIIIITTTGTATAAC-3'

CT-R
(SEQ ID NO: 6)
5'-CCAATTGTAATAGAAGCATTGGTTGIIIIITTATTGGAGA-3'

CT-PTO
(SEQ ID NO: 7)
5'-<u>GATTACGCGACCGCATCAGAAG</u>CTGTCATTTTGGCTGCG[C3 spacer]-3'

CT-CTO
(SEQ ID NO: 8)
5'-[BHQ-2]GCGCTGGATACCCTGGACGA[T(CAL Fluor Red 610)]ATGTGCGGTCGCGTAATC[C3 spacer]-3'

MG-F
(SEQ ID NO: 16)
5'-AAAACCCACGGAAATGATGAGAIIIIIATTGGTTCTAC-3'

MG-R
(SEQ ID NO: 17)
5'-CTCGTTAATTTACCTATTCCATTTTGIIIIICTGATAAAAG-3'

MG-P
(SEQ ID NO: 18)
5'-[CAL Fluor Red 610]GAGTTCTTTCAAGAACAGCA AGAGGTGT[BHQ-2]-3'

(I: Deoxyinosine)
(Underlined letters indicate the 5'-tagging portion of PTO)

The real-time PCR was conducted in the final volume of 20 μl containing a target nucleic acid (10 pg of NG genomic DNA, 10 pg of CT genomic DNA, 10 pg of MG genomic DNA, a mixture of each 10 pg of NG and CT genomic DNA, a mixture of each 10 pg of NG and MG genomic DNA, a mixture of each 10 pg of CT and MG genomic DNA; or a mixture of each 10 pg of NG, CT and MG genomic DNA), 5 pmole of upstream primer (SEQ ID NO: 1) and 5 pmole of downstream primer (SEQ ID NO: 2) for NG target amplification, 3 pmole of PTO (SEQ ID NO: 3), 1 pmole of CTO (SEQ ID NO: 4), 5 pmole of upstream primer (SEQ ID NO: 5) and 5 pmole of downstream primer (SEQ ID NO: 6) for CT target amplification, 3 pmole of PTO (SEQ ID NO: 7), 1 pmole of CTO (SEQ ID NO: 8), 5 pmole of upstream primer (SEQ ID NO: 16) and 5 pmole of downstream primer (SEQ ID NO: 17) for MG target amplification, 1 pmole of TaqMan probe (SEQ ID NO: 18), and 10 μl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C., 72° C., and 95° C. of each cycle.

Figure 5A:
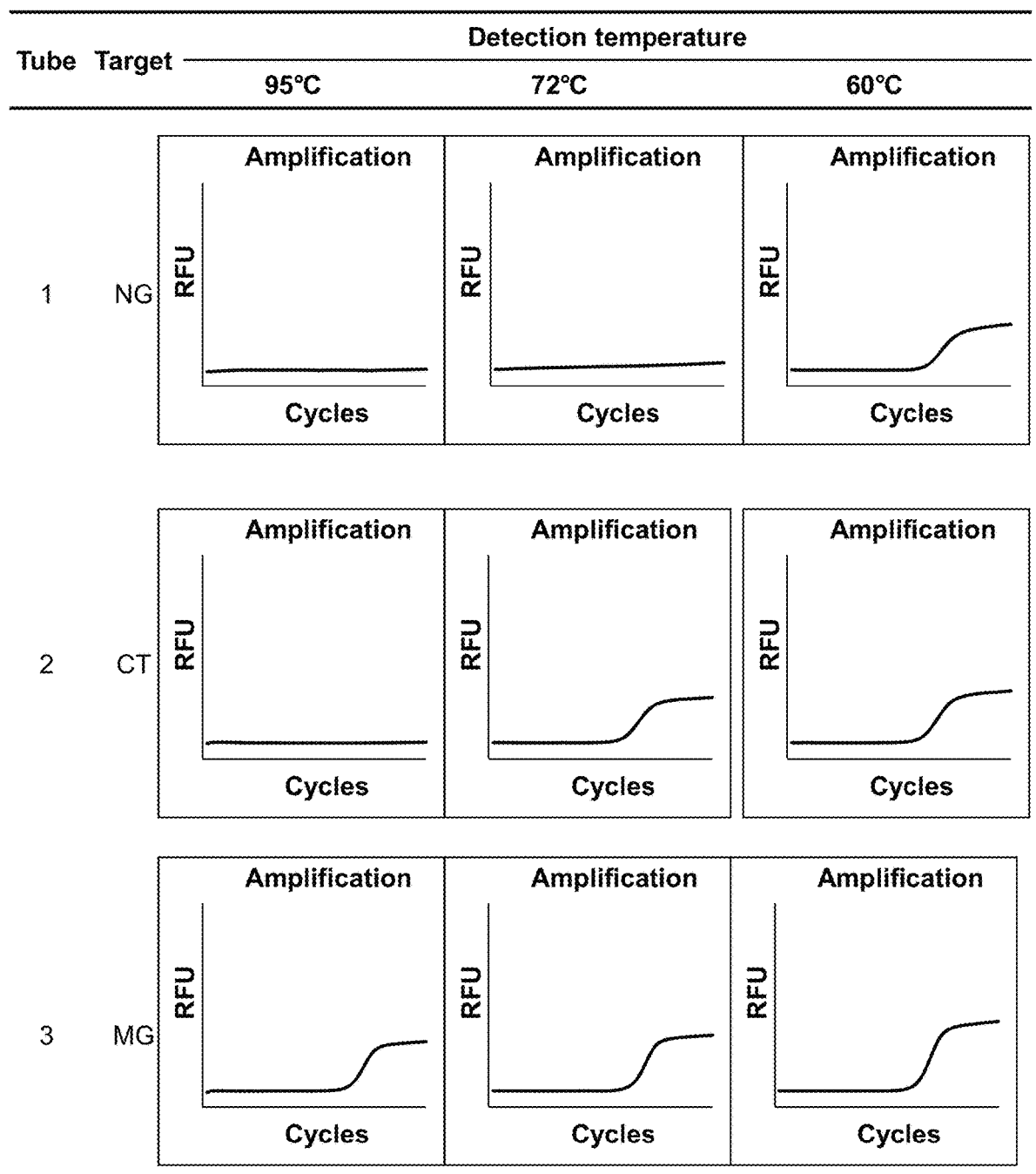
FIGS. 5a-5c represent the detection results of the present invention using different detection temperatures to detect three target sequences (genomic DNA of *Neisseria gonorrhoeae* (NG), genomic DNA of *Chlamydia trachomatis* (CT), and genomic DNA of *Mycoplasma genitalium* (MG)). The signal for MG was generated by TaqMan real-time PCR method, and the signals for CT and NG were generated by PTOCE real-time PCR method. "95° C." was selected as a signal detection temperature for MG, "72° C." was selected as a signal detection temperature for CT, and "60° C." was selected as a signal detection temperature for NG with consideration of the signal generating means.
Figure 5B:
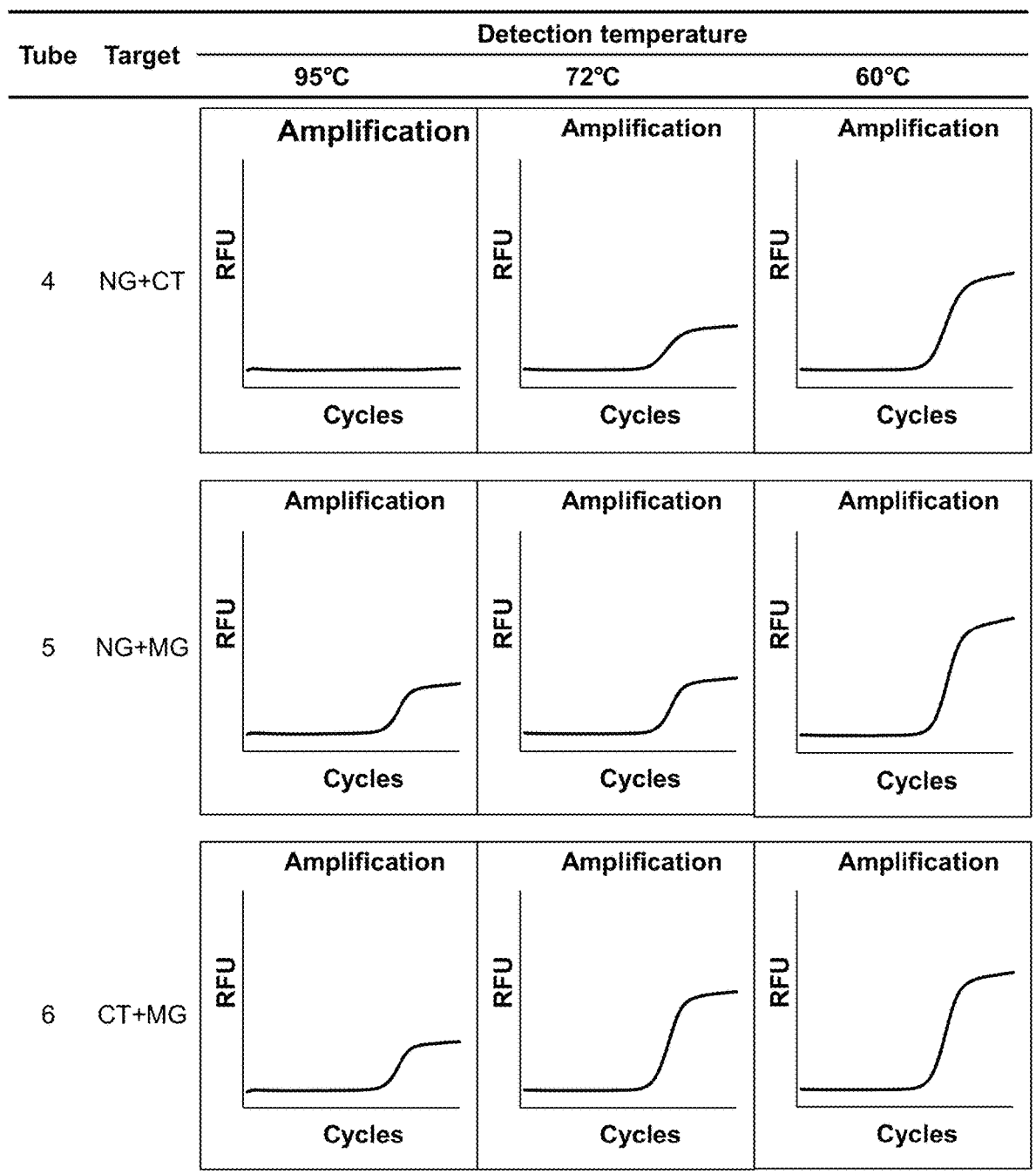
Figure 5C:
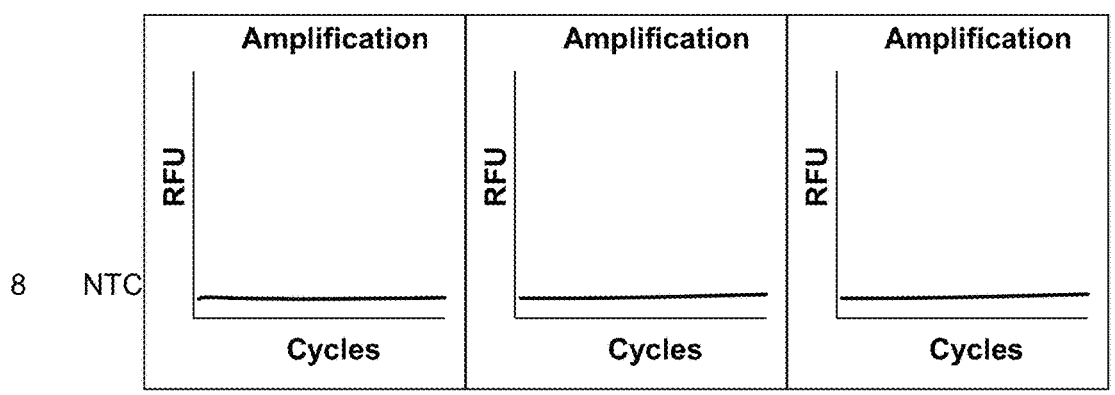

As shown in FIGS. 5A, 5B, and 5C, the signals detected at 95° C. enabled us to determine at least the presence of MG having the relatively highest detection temperature (95° C.) in Tubes 3, 5, 6, and 7.

Using the difference due to the absence of a signal at the relatively highest detection temperature (95° C.) and the presence of a signal at the relatively middle detection temperature (72° C.) enabled us determining the presence of CT having the relatively middle detection temperature (72° C.) in Tubes 2 and 4. Furthermore, Using the difference due to the absence of a signal at the relatively middle detection temperature (72° C.) and the presence of a signal at the relatively lowest detection temperature (60° C.) permitted us to determine the presence of NG having the relatively lowest detection temperature (60° C.) in Tube 1.

The difference between the signals detected at 95° C., 72° C. and 60° C. was calculated by subtraction of End-RFUs (End-ΔRFU) in order to examine whether CT or NG co-present with other targets can be identified in a single reaction vessel.

The FIG. 5D shows End-ΔRFUs calculated with the RFU values of the end points at 95° C. and 72° C. (All RFU values were derived and exported from "Baseline subtracted curve fit" analysis data in instrumental software). The threshold "300" was applied to determine the presence of CT. The threshold was determined with considering the End-ΔRFUs from the tubes containing no CT (Tubes 1, 3 and 5). In accordance with the threshold, the presence of CT was confirmed in Tubes 2, 4, 6 and 7.

The FIG. 5E shows End-ΔRFU calculated with the RFU values of the end points at 72° C. and 60° C. (All RFU values were derived and exported from "Baseline subtracted curve fit" analysis data in instrumental software). The threshold "800" was applied to determine the presence of NG. The threshold was determined with considering the End-ΔRFUs from the tubes containing no NG (Tubes 2, 3 and 6). In accordance with the threshold, the presence of NG was confirmed in Tubes 1, 4, 5 and 7.

These results indicate that in the TaqMan/PTOCE real-time method comprising signal detection at three temperatures, (i) the signal detection at the relatively highest detection temperature allows detecting the target nucleic acid sequence having the relatively highest detection temperature and (ii) the difference obtained from the signals at different detection temperatures can be used to identify the target nucleic acid sequences having the detection temperatures lower than the highest detection temperature.

Therefore, a plural of target nucleic acids can be detected in a single reaction vessel by using a single detection channel and TaqMan/PTOCE real-time PCR comprising signal detection at different temperatures.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting two target nucleic acid sequences in a sample using different detection temperatures, comprising:

(a) incubating the sample with two signal-generating means for detection of the two target nucleic acid sequences in a single first reaction vessel and detecting a generated signal by using a single type of detector; wherein the two target nucleic acid sequences are known; wherein each of the target nucleic acid sequences is detected by a corresponding signal-generating means; wherein each of the two signal-generating means comprises an oligonucleotide with a fluorescent label and when each of the two signal-generating means comprises primers and probes, the nucleotide sequences of the primers and probes are designed not to bind to each other; wherein one of the two target nucleic acid sequences has a high detection temperature and the other has a low detection temperature determined by the corresponding signal-generating means; wherein the signal-generating means for the target nucleic acid sequence having the high detection temperature generates a signal at the high detection temperature and at the low detection temperature, dependently on the presence of the target nucleic acid sequence having the high detection temperature, and the signal-generating means for the target nucleic acid sequence having the low detection temperature generates a signal at the low detection temperature, dependently on the presence of the target nucleic acid sequence having the low detection temperature; wherein the high detection temperature is a temperature at which a signal is generated from the signal-generating means for the target nucleic acid sequence having the high detection temperature, and the low detection temperature is a temperature at which a signal is generated from the two signal-generating means; wherein the wavelengths of signals to be generated by the two signal-generating means are not differentiated by the single type of detector; wherein the detection is performed only at both the high detection temperature and the low detection temperature at each cycle, selected several cycles or end-point of real-time PCR (polymerase chain reaction) and wherein the two target nucleic acid sequences are amplified; and (b) determining the presence of the two target nucleic acid sequences by the signals detected in the step (a); wherein (i) the presence of the target nucleic acid sequence having the high detection temperature is determined by the signal detected at the high detection temperature and (ii) the presence of the target nucleic acid sequence having the low detection temperature is determined by comparing a difference between the signal intensity detected at the high detection temperature and the signal intensity detected at the low detection temperature with a threshold, wherein the difference is calculated by multiplying the signal detected at the high detection temperature by a reference value and then subtracting the multiplication result from the signal detected at the low detection temperature, wherein the reference value is obtained by (i) subjecting the target nucleic acid sequence having the high detection temperature to real-time PCR using the signal-generating means for the target nucleic acid sequence having the high detection temperature in a second reaction vessel other than the first reaction vessel in the step (a), (ii) detecting signals only at the high detection temperature and the low detection temperature in each cycle, selected several cycles or end-point of real-time PCR, and (iii) then obtaining a ratio of the signal detected at the low detection temperature to the signal detected at the high detection temperature;

wherein the method does not comprise a melting curve analysis.

2. The method according to claim 1, wherein the signal-generating means for each of the target nucleic acid sequences are a signal-generating means to generate a signal in a dependent manner on the formation of a duplex.

3. The method according to claim 1, wherein the signal-generating means for each of the target nucleic acid sequences are a signal-generating means by formation of a duplex in a dependent manner on cleavage of a mediation oligonucleotide having 15-150 nucleotides specifically hybridized with the target nucleic acid sequence.

4. The method according to claim 1, wherein the signal-generating means for the target nucleic acid sequence having the high detection temperature is a signal-generating means by cleavage of a detection oligonucleotide having 5-100 nucleotides by an enzyme having 5'-nuclease activity, and the signal-generating means for the target nucleic acid sequence having the low detection temperature is a signal-generating means by the formation of a duplex.

5. The method according to claim 1, wherein the signal-generating means for the target nucleic acid sequence having the high detection temperature is a signal-generating means by cleavage of a detection oligonucleotide having 5-100 nucleotides by an enzyme having 5' nuclease activity, and the signal-generating means for the target nucleic acid sequence having the low detection temperature is a signal-generating means by formation of a duplex in a dependent manner on cleavage of a mediation oligonucleotide having 15-150 nucleotides specifically hybridized with the target nucleic acid sequence.

6. The method according to claim 1, wherein the two signal-generating means comprise an identical label and the wavelengths of signals from the label are not differentiated by the single type of detector.

7. The method according to claim 1, wherein when the signal is not detected at the high detection temperature, the determination of the presence of the target nucleic acid sequence having the low detection temperature is made by the signal detected at the low detection temperature.

8. The method according to claim 1, wherein when the target nucleic acid sequence having the high detection temperature is present, the presence of the target nucleic acid sequence having the low detection temperature is determined by calculating the difference with a reference value.

9. The method according to claim 8, wherein the reference value, is obtained by (i) incubating the target nucleic acid sequence having the high detection temperature with a signal-generating means for detection of the target nucleic acid sequence having the high detection temperature in a second reaction vessel other than the first reaction vessel in the step (a), (ii) detecting signals at both the high detection temperature and the low detection temperature, and (iii) then obtaining a difference between the signal detected at the high detection temperature and the signal detected at the low detection temperature.

10. The method according to claim 1, wherein the two target nucleic acid sequences comprise a nucleotide variation and one of the two target nucleic acid sequences comprises one type of the nucleotide variation and the other comprises the other type of the nucleotide variation.

* * * * *

SEQUENCE LISTING

<160> NUMBER OF SEQ ID NOS: 18

<210> SEQ ID NO 1
<211> LENGTH: 37
<212> TYPE: DNA
<213> ORGANISM: Artificial Sequence
<220> FEATURE:
<223> OTHER INFORMATION: NG-F
<220> FEATURE:
<221> NAME/KEY: misc_feature
<222> LOCATION: (22)..(26)
<223> OTHER INFORMATION: n denotes deoxyinosine

<400> SEQUENCE: 1
tacgcctgct actttcacgc tnnnnngtaa tcagatg				37

<210> SEQ ID NO 2
<211> LENGTH: 37
<212> TYPE: DNA
<213> ORGANISM: Artificial Sequence
<220> FEATURE:
<223> OTHER INFORMATION: NG-R
<220> FEATURE:
<221> NAME/KEY: misc_feature
<222> LOCATION: (22)..(26)
<223> OTHER INFORMATION: n denotes deoxyinosine

<400> SEQUENCE: 2

```
caatggatcg gtatcactcg cnnnnncgag caagaac                                37
```

<210> SEQ ID NO 3
<211> LENGTH: 34
<212> TYPE: DNA
<213> ORGANISM: Artificial Sequence
<220> FEATURE:
<223> OTHER INFORMATION: NG-PTO

<400> SEQUENCE: 3

```
gtacgcgata cgggcccctc attggcgtgt ttcg                                   34
```

<210> SEQ ID NO 4
<211> LENGTH: 39
<212> TYPE: DNA
<213> ORGANISM: Artificial Sequence
<220> FEATURE:
<223> OTHER INFORMATION: NG-CTO

<400> SEQUENCE: 4

```
tttttttttt tttttttttg tactgcccgt atcgcgtac                              39
```

<210> SEQ ID NO 5
<211> LENGTH: 40
<212> TYPE: DNA
<213> ORGANISM: Artificial Sequence
<220> FEATURE:
<223> OTHER INFORMATION: CT-F
<220> FEATURE:
<221> NAME/KEY: misc_feature
<222> LOCATION: (26)..(30)
<223> OTHER INFORMATION: n denotes deoxyinosine

<400> SEQUENCE: 5

```
gagttttaaa atgggaaatt ctggtnnnnn tttgtataac                             40
```

<210> SEQ ID NO 6
<211> LENGTH: 40
<212> TYPE: DNA
<213> ORGANISM: Artificial Sequence
<220> FEATURE:
<223> OTHER INFORMATION: CT-R
<220> FEATURE:
<221> NAME/KEY: misc_feature
<222> LOCATION: (26)..(30)
<223> OTHER INFORMATION: n denotes deoxyinosine

<400> SEQUENCE: 6

```
ccaattgtaa tagaagcatt ggttgnnnnn ttattggaga                             40
```

<210> SEQ ID NO 7
<211> LENGTH: 39
<212> TYPE: DNA
<213> ORGANISM: Artificial Sequence
<220> FEATURE:
<223> OTHER INFORMATION: CT-PTO

<400> SEQUENCE: 7

```
gattacgcga ccgcatcaga agctgtcatt ttggctgcg                              39
```

<210> SEQ ID NO 8
<211> LENGTH: 39
<212> TYPE: DNA
<213> ORGANISM: Artificial Sequence
<220> FEATURE:
<223> OTHER INFORMATION: CT-CTO

<400> SEQUENCE: 8

```
gcgctggata ccctggacga tatgtgcggt cgcgtaatc                    39

<210> SEQ ID NO 9
<211> LENGTH: 26
<212> TYPE: DNA
<213> ORGANISM: Artificial Sequence
<220> FEATURE:
<223> OTHER INFORMATION: CT-P

<400> SEQUENCE: 9
catcagaagc tgtcattttg gctgcg                                  26

<210> SEQ ID NO 10
<211> LENGTH: 32
<212> TYPE: DNA
<213> ORGANISM: Artificial Sequence
<220> FEATURE:
<223> OTHER INFORMATION: M677-F
<220> FEATURE:
<221> NAME/KEY: misc_feature
<222> LOCATION: (18)..(22)
<223> OTHER INFORMATION: n denotes deoxyinosine

<400> SEQUENCE: 10
ccaccccgaa gcagggannn nngaggctga cc                           32

<210> SEQ ID NO 11
<211> LENGTH: 34
<212> TYPE: DNA
<213> ORGANISM: Artificial Sequence
<220> FEATURE:
<223> OTHER INFORMATION: M677-R
<220> FEATURE:
<221> NAME/KEY: misc_feature
<222> LOCATION: (20)..(24)
<223> OTHER INFORMATION: n denotes deoxyinosine

<400> SEQUENCE: 11
caagtgatgc ccatgtcggn nnnngccttc acaa                         34

<210> SEQ ID NO 12
<211> LENGTH: 37
<212> TYPE: DNA
<213> ORGANISM: Artificial Sequence
<220> FEATURE:
<223> OTHER INFORMATION: M677-W-PTO

<400> SEQUENCE: 12
ggtcccgacg ttagctcccg cagacacctt ctccttc                      37

<210> SEQ ID NO 13
<211> LENGTH: 39
<212> TYPE: DNA
<213> ORGANISM: Artificial Sequence
<220> FEATURE:
<223> OTHER INFORMATION: M677-W-CTO

<400> SEQUENCE: 13
cctcggtgcc acgccatcgg ttcttctaac gtcgggacc                    39

<210> SEQ ID NO 14
<211> LENGTH: 38
<212> TYPE: DNA
<213> ORGANISM: Artificial Sequence
<220> FEATURE:
<223> OTHER INFORMATION: M677-M-PTO
```

-continued

```
<400> SEQUENCE: 14
acgtcgattc gcactcccgc agacaccttc tccttcaa                            38

<210> SEQ ID NO 15
<211> LENGTH: 38
<212> TYPE: DNA
<213> ORGANISM: Artificial Sequence
<220> FEATURE:
<223> OTHER INFORMATION: M677-M-CTO

<400> SEQUENCE: 15
tttttttttt tttttttttt tattctgcga atcgacgt                            38

<210> SEQ ID NO 16
<211> LENGTH: 38
<212> TYPE: DNA
<213> ORGANISM: Artificial Sequence
<220> FEATURE:
<223> OTHER INFORMATION: MG-F
<220> FEATURE:
<221> NAME/KEY: misc_feature
<222> LOCATION: (23)..(27)
<223> OTHER INFORMATION: n denotes deoxyinosine

<400> SEQUENCE: 16
aaaacccacg gaaatgatga gannnnnatt ggttctac                            38

<210> SEQ ID NO 17
<211> LENGTH: 41
<212> TYPE: DNA
<213> ORGANISM: Artificial Sequence
<220> FEATURE:
<223> OTHER INFORMATION: MG-R
<220> FEATURE:
<221> NAME/KEY: misc_feature
<222> LOCATION: (27)..(31)
<223> OTHER INFORMATION: n denotes deoxyinosine

<400> SEQUENCE: 17
ctcgttaatt tacctattcc attttgnnnn nctgataaaa g                        41

<210> SEQ ID NO 18
<211> LENGTH: 28
<212> TYPE: DNA
<213> ORGANISM: Artificial Sequence
<220> FEATURE:
<223> OTHER INFORMATION: MG-P

<400> SEQUENCE: 18
gagttctttc aagaacagca agaggtgt                                       28
```